US009060782B2

(12) United States Patent
    Daniel et al.

(10) Patent No.: US 9,060,782 B2
(45) Date of Patent: Jun. 23, 2015

(54) DEVICES AND METHODS FOR THERMAL ABLATION OF BIOLOGICAL TISSUE USING GEOMETRIC ABLATION PATTERNS

(75) Inventors: Steven A. Daniel, Fremont, CA (US); David L. Morris, Lugarno (AU); Kee Sein Lee, Newark, CA (US)

(73) Assignee: S.D.M.H. PTY. LTD., Sydney (AU)

( * ) Notice: Subject to any disclaimer, the term of this patent is extended or adjusted under 35 U.S.C. 154(b) by 1374 days.

(21) Appl. No.: 12/107,034

(22) Filed: Apr. 21, 2008

(65) Prior Publication Data

US 2008/0319436 A1    Dec. 25, 2008

Related U.S. Application Data

(63) Continuation-in-part of application No. 10/889,756, filed on Jul. 12, 2004, now Pat. No. 7,399,299, and a continuation-in-part of application No. 11/335,301, filed on Jan. 18, 2006, now Pat. No. 8,845,635.

(60) Provisional application No. 60/925,326, filed on Apr. 19, 2007, provisional application No. 60/937,670, filed on Jun. 28, 2007, provisional application No. 60/975,461, filed on Sep. 26, 2007, provisional application No. 61/035,928, filed on Mar. 12, 2008.

(51) Int. Cl.
    *A61B 18/18* (2006.01)
    *A61B 18/14* (2006.01)
    *A61B 18/00* (2006.01)

(52) U.S. Cl.
    CPC ........... *A61B 18/148* (2013.01); *A61B 18/1477* (2013.01); *A61B 18/1487* (2013.01); *A61B 2018/00267* (2013.01)

(58) Field of Classification Search
    CPC .... A61B 18/12; A61B 18/1206; A61B 18/14; A61B 18/1402; A61B 18/148; A61B 18/1482; A61B 18/1487; A61B 18/1492; A61B 2018/0016; A61B 2018/00166; A61B 2018/00214; A61B 2018/00267; A61B 2018/00333; A61B 2018/00345; A61B 2018/00505; A61B 2108/00529; A61B 2018/00577; A61B 2018/0091; A61B 2018/0142; A61B 2018/1467; A61B 2018/1475
    USPC ....................................... 606/27–52
    See application file for complete search history.

(56) References Cited

U.S. PATENT DOCUMENTS

| 5,313,943 | A | * | 5/1994 | Houser et al. | 600/374 |
|---|---|---|---|---|---|
| 5,672,174 | A | * | 9/1997 | Gough et al. | 606/41 |
| 5,683,384 | A | * | 11/1997 | Gough et al. | 606/41 |
| 5,728,143 | A | * | 3/1998 | Gough et al. | 607/101 |

(Continued)

*Primary Examiner* — Joseph Stoklosa
*Assistant Examiner* — Amanda Scott
(74) *Attorney, Agent, or Firm* — IPR Law Group, PC

(57) ABSTRACT

A tissue ablation system including numerous components and methods is described herein for encircling target tissue and generating tissue ablation volumes in various biological tissues. The biological tissue includes tissue of a variety of organs of the human body including the liver, spleen, kidney, lung, breast and other organs, but is not so limited. The tissue ablation device comprises an energy source and at least one trocar coupled to the energy source, the trocar having a body, a proximal end, and a distal end. The trocar carries an electrode array that comprises a plurality of electrodes, each electrode of the plurality of electrodes is configured to extend from the trocar when moved from a retracted state to a deployed state, and to have at least one radius of curvature in the deployed state so that the electrode array forms a series of shaped electrodes in the deployed state.

49 Claims, 56 Drawing Sheets

(56) References Cited

U.S. PATENT DOCUMENTS

| | | | |
|---|---|---|---|
| 5,904,680 A * | 5/1999 | Kordis et al. | 606/41 |
| 6,006,755 A * | 12/1999 | Edwards | 128/898 |
| 6,009,877 A * | 1/2000 | Edwards | 128/898 |
| 6,090,105 A * | 7/2000 | Zepeda et al. | 606/41 |
| 6,221,039 B1 * | 4/2001 | Durgin et al. | 604/22 |
| 6,622,731 B2 * | 9/2003 | Daniel et al. | 128/898 |
| 6,679,269 B2 * | 1/2004 | Swanson | 128/898 |
| 6,881,213 B2 * | 4/2005 | Ryan et al. | 606/41 |
| 6,979,330 B2 * | 12/2005 | Kelly et al. | 606/41 |
| 7,615,049 B2 * | 11/2009 | West et al. | 606/41 |

* cited by examiner

| ABLATION SIZE (cm) | TIMER (min:sec) | POWER SETTING (Watts) |
|---|---|---|
| 3.5 | 3:00 | 60 - 80 |
| 5 | 5:00 | 100 - 135 |
| 7 | 12:00 | 135 - 150 |

1300

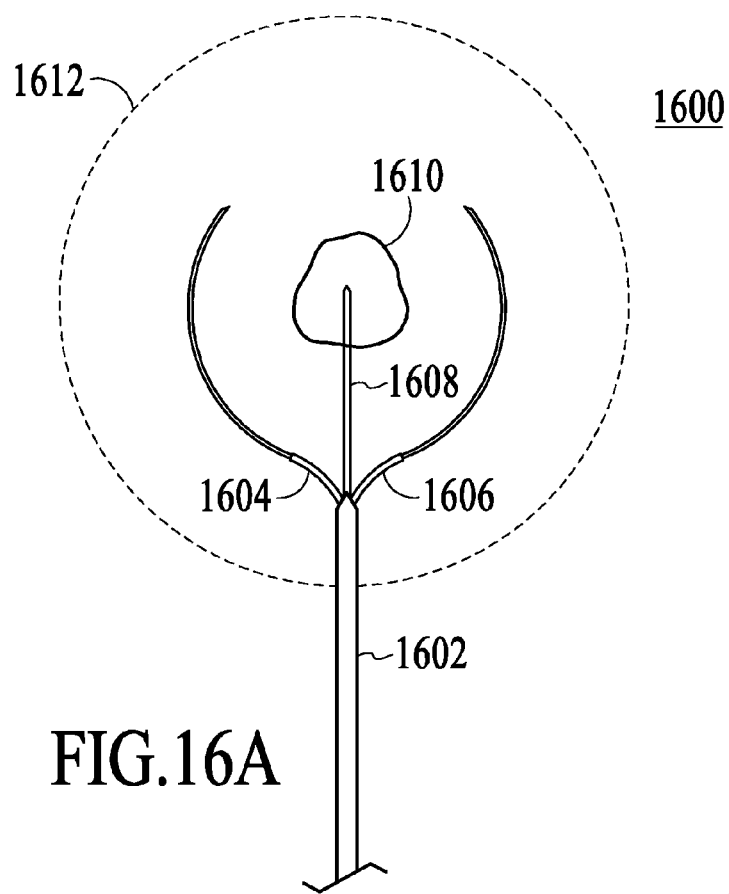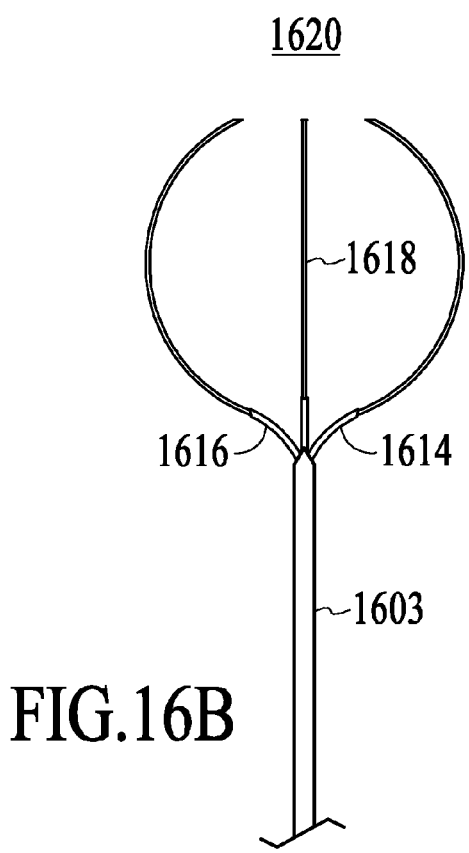
FIG.16A
FIG.16B

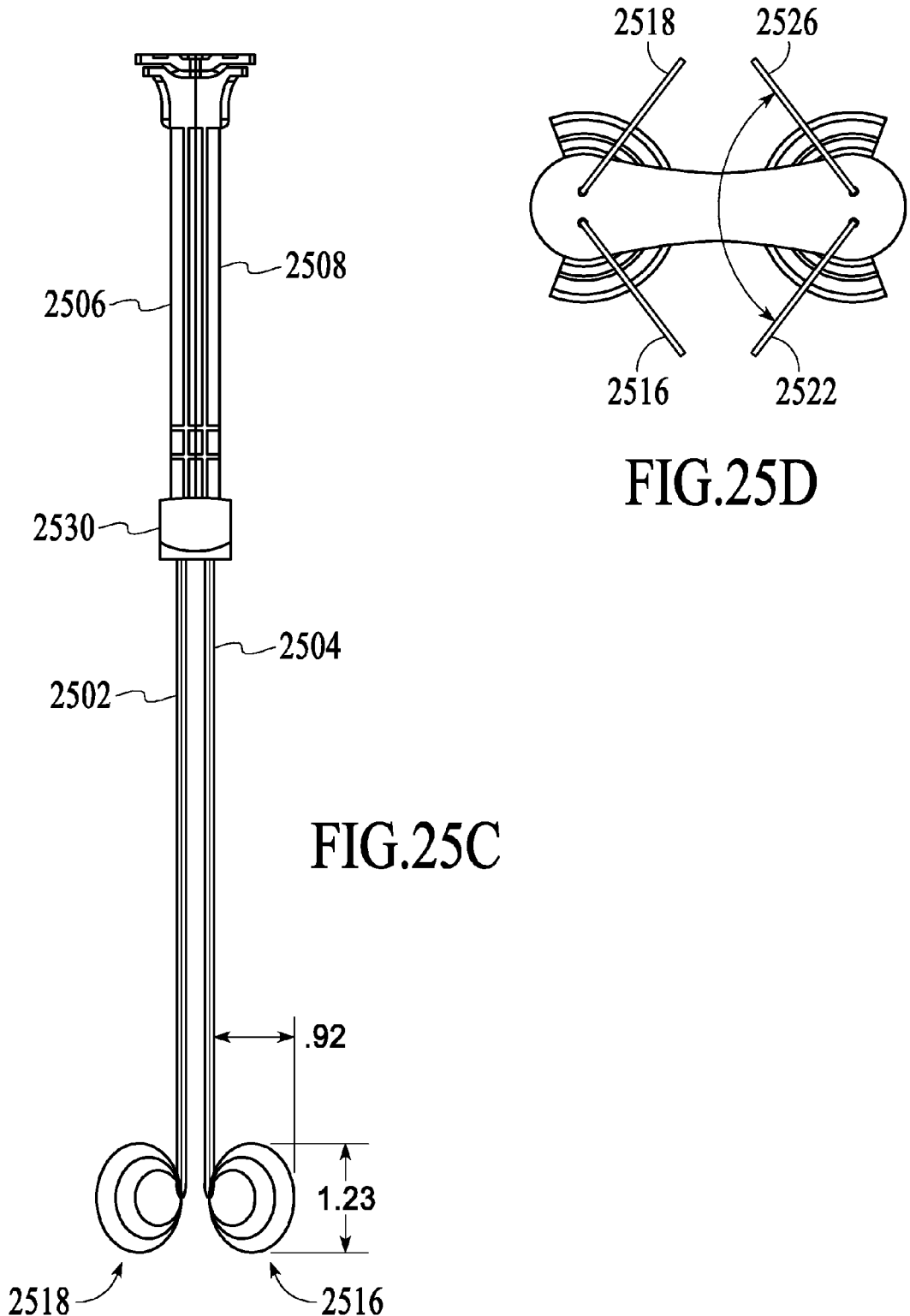

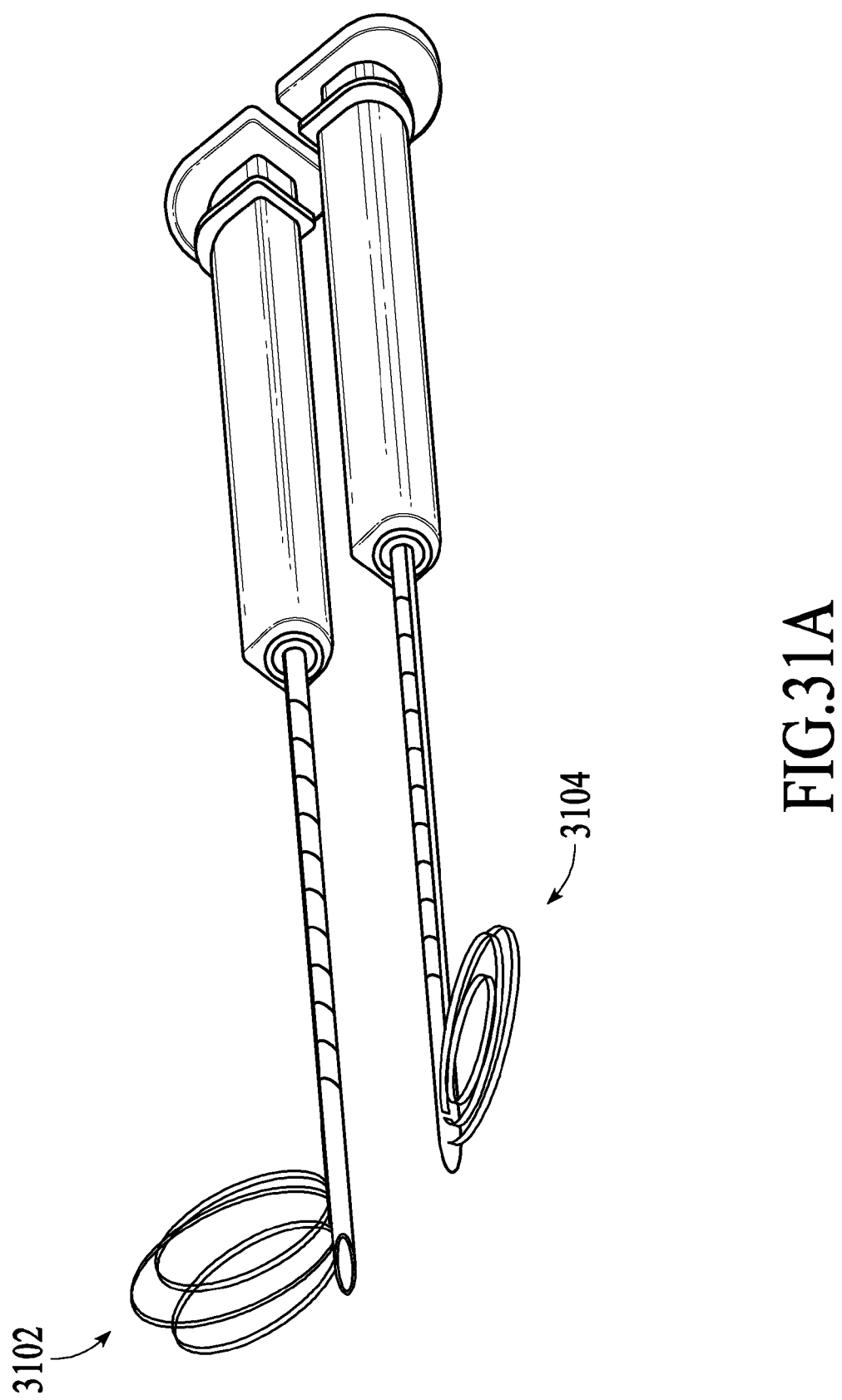

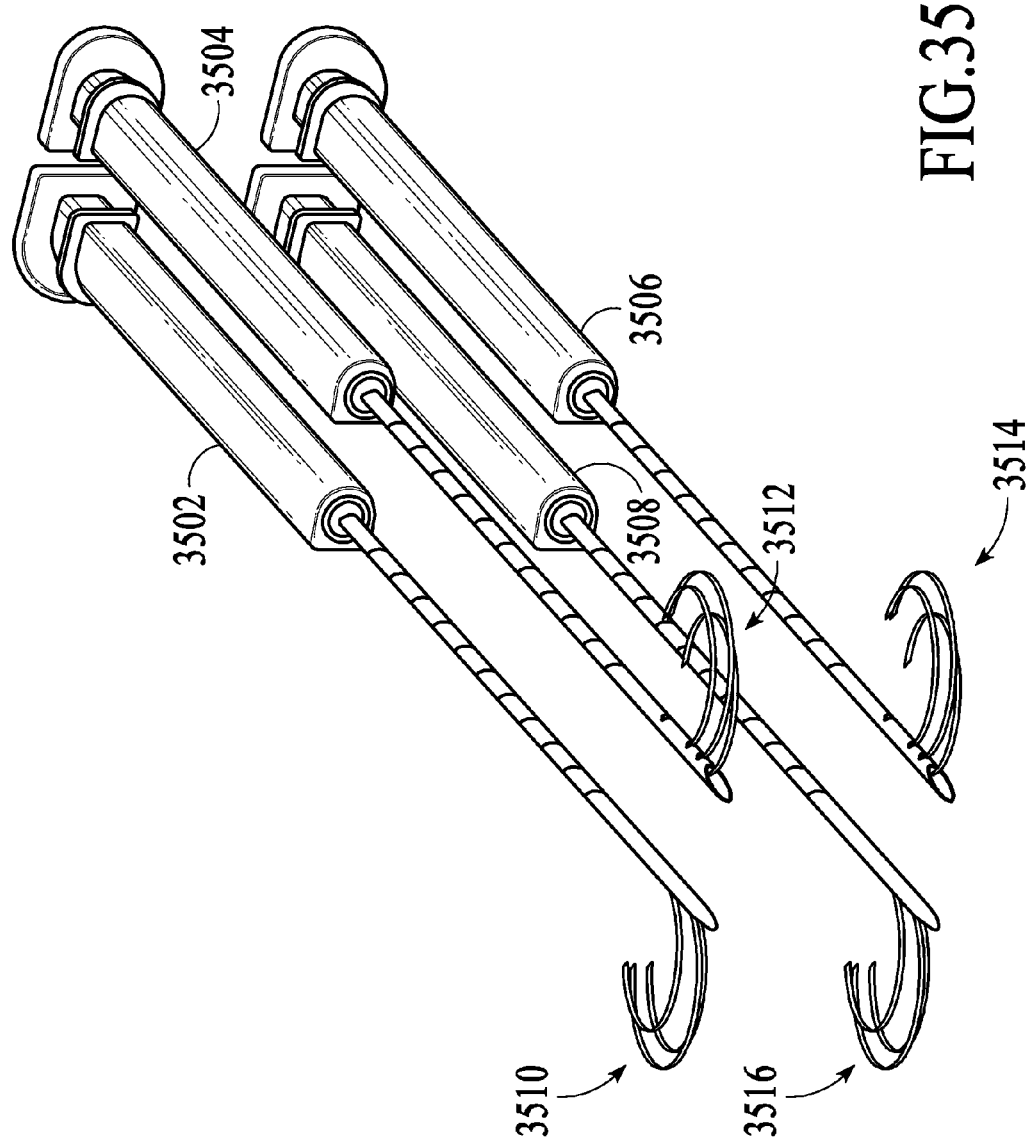

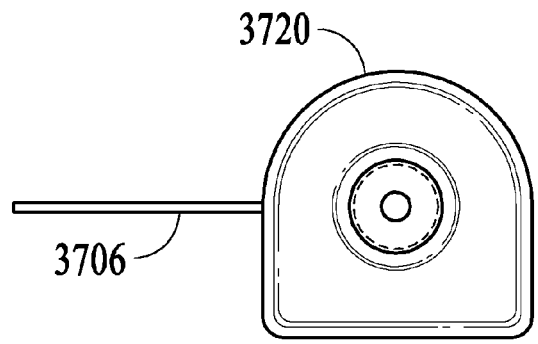
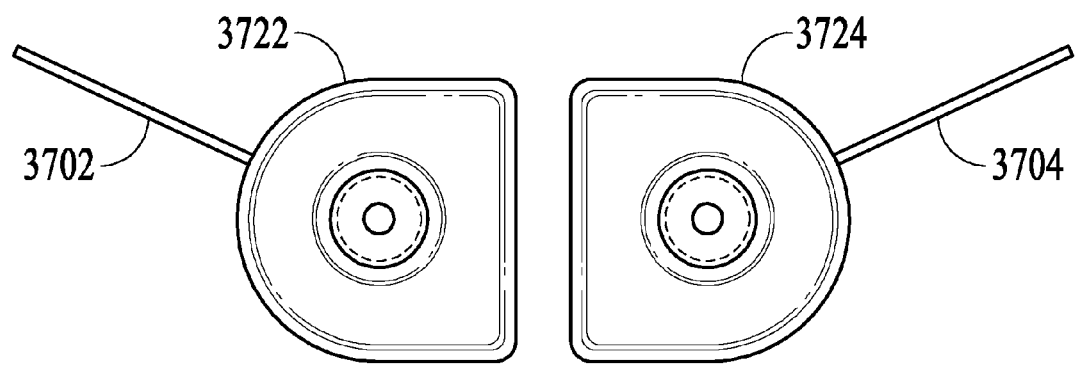
FIG.37C

FIG. 40

Trocar Dimensions

| Item | Nominal(s) | Min | Max |
|---|---|---|---|
| 7cm inCircle Electrode Diameters | 3.2 cm (2ea)/2.5 cm (2ea) | N/A | N/A |
| 7cm inCircle Classic Electrode Spacing | 1 cm | N/A | N/A |
| 7cm inCircle Classic Electrode Dimensions | 0.012in x 0.032in | N/A | N/A |
| 5cm inCircle Classic Electrode Diameters | 2.6 cm (1ea)/2.2 cm (2ea) | N/A | N/A |
| 5cm inCircle Classic Electrode Spacing | 0.8 cm | N/A | N/A |
| 5cm inCircle Classic Electrode Dimensions | 0.012in x 0.032in / 0.010 x 0.032 | N/A | N/A |
| 3.5cm inCircle Classic Electrode Diameters | 1.8 cm (2ea) | N/A | N/A |
| 3.5cm inCircle Classic Electrode Spacing | 0.8 cm | N/A | N/A |
| 3.5cm inCircle Classic Electrode Dimensions | 0.010in x 0.032in | N/A | N/A |
| 5cm inCircle Monarch Electrode Diameters | 2 cm (3ea) | N/A | N/A |
| 5cm inCircle Monarch Electrode Spacing | 0.8 cm | N/A | N/A |
| 5cm inCircle Monarch Electrode Dimensions | 0.010 x 0.031 | N/A | N/A |
| 4cm inCircle Monarch Electrode Diameters | 1.5 cm (3ea) | N/A | N/A |
| 4cm inCircle Monarch Electrode Spacing | 0.8 cm | N/A | N/A |
| 4cm inCircle Monarch Electrode Dimensions | 0.008 x 0.031 | N/A | N/A |
| 3cm inCircle Monarch Electrode Diameters | 1.2 cm (3ea) | N/A | N/A |
| 3cm inCircle Monarch Electrode Spacing | 0.8 cm | N/A | N/A |
| 3cm inCircle Monarch Electrode Dimensions | 0.006in x 0.025in | N/A | N/A |
| Ablation Size - InCircle Classic | 3.5/5/7 cm | 1.5 cm | 15 cm |
| Ablation Size - InCircle Monarch | 3/4/5 cm | 1.5 cm | 15 cm |
| Electrode Sizes | N/A | 0.004in x 0.010in | 0.025in x 0.075in |
| Electrode Diameter | N/A | 0.6cm | 7cm |
| Electrode Spacing | N/A | 2mm | 2cm |
| Electrode Angles | 110 / 180 degrees | 30 degrees | 180 degrees |

DEVICES AND METHODS FOR THERMAL ABLATION OF BIOLOGICAL TISSUE USING GEOMETRIC ABLATION PATTERNS

RELATED APPLICATIONS

The present application is a continuation in part application of U.S. patent application Ser. No. 10/889,756, filed Jul. 12, 2004.

The present application is a continuation in part application of U.S. patent application Ser. No. 11/335,301, filed Jan. 18, 2006.

The present application claims the benefit of U.S. Patent Application No. 60/925,326, filed Apr. 19, 2007.

The present application claims the benefit of U.S. Patent Application No. 60/937,670, filed Jun. 28, 2007.

The present application claims the benefit of U.S. Patent Application No. 60/975,461, filed Sep. 26, 2007.

The present application claims the benefit of U.S. patent application Ser. No. 61/035,928, filed Mar. 12, 2008.

TECHNICAL FIELD

This invention relates generally to devices and methods for tissue ablation, and more particularly to devices for encircling target biological tissue.

BACKGROUND

Standard surgical procedures such as tissue resection for use in treatment of benign and malignant tumors of the liver and other organs have several key shortcomings affecting efficacy, morbidity and mortality. A fundamental issue in these shortcomings is the inability of the resection to be performed in a variety of cases. To help overcome this limitation a series of mono-polar radio frequency (RF) devices were designed for use in tissue ablation and resection. These mono-polar devices however have limited usefulness in typical clinical settings because they are overly complex and difficult to use, and result in time consuming procedures that can lead to auxiliary injury to patients through grounding pad burns. Further, these mono-polar tissue ablation devices are limited in the scope and size of the ablation that can be created, and exhibit poor consistency of ablative results along with an overall low efficiency. Typical known ablation devices are designed to pierce into that target tissue and ablate the tissue from the inside out. This method can result in uneven heating of the target tissue and result in tumor seeding due to repeated penetration and retraction from malignant tissue. Consequently, there is a need for a tissue ablation system that overcomes the shortcomings of these mono-polar tissue ablation devices.

Although certain multiple electrode RF ablation systems have been developed, such conventional systems generally suffer from significant drawbacks related to inadequate RF heating. RF heating results from electrical current flow through the ionic fluid that permeates biological tissue, typically between an electrode and ground pad. High temperatures, however result in decreased electrical conductivity resulting in an impedance spike or rolloff that precedes the end of active heating. Present multi-electrode RF ablation systems require current to be switched between electrodes so each electrode is active less than 100% of the procedure time. This can lead to rehydration of target tissue, and adds to the time required to complete a procedure. These systems are also vulnerable to the heat-sink effect of critical heat from the electrodes being drawn away by flowing blood, thus decreasing the temperature of ablation. These problems can result in high local recurrence rates in perivascular regions due to the inability to generate a sufficient amount of sustained heat necessary to fully ablate the target tissue.

INCORPORATION BY REFERENCE

Each patent, patent application, and/or publication mentioned in this specification is herein incorporated by reference in its entirety to the same extent as if each individual patent, patent application, and/or publication was specifically and individually indicated to be incorporated by reference.

BRIEF DESCRIPTION OF THE DRAWINGS

FIG. 16A illustrates an ablation device containing both surrounding electrodes and a penetrating electrode, according to an embodiment.

FIG. 16B illustrates an ablation device containing surrounding electrodes and a fluid delivery element, according to an embodiment.

FIG. 25C is a side view of a dual-trocar ablation device, under the embodiment of FIG. 25A.

FIG. 25D is an end view of a dual-trocar ablation device, under the embodiment of FIG. 25A.

FIG. 31A shows a front perspective view of a dual-trocar ablation system formed from the simultaneous use of two single-trocar ablation devices, each single-trocar ablation device using one or more spiral electrodes in an array protruding fully or nearly fully from the distal end of the corresponding trocar, under an embodiment.

FIG. 35 illustrates a quad-trocar ablation system in which the electrode arrays are deployed from their respective trocars at less than full extension length, under an embodiment.

FIG. 37C shows a rear view of the tri-trocar ablation system of FIG. 37A, under an embodiment.

FIG. 40 is a table of dimensions corresponding to the tissue ablation system, under various embodiments described herein.

Figure 1:
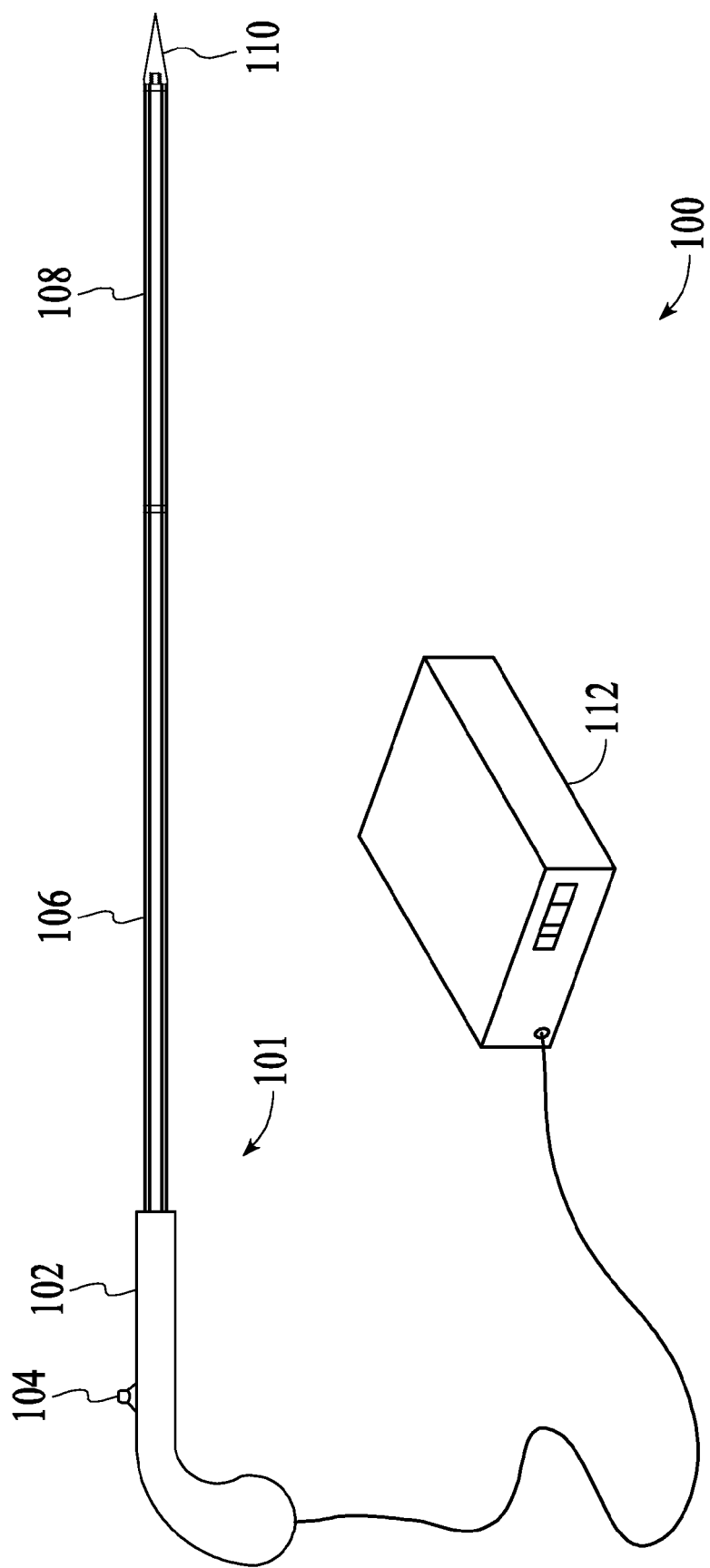
FIG. 1 is a tissue ablation device including a hand piece, a deployment slider, a delivery member/tube, and a plurality of energy conduits in a retracted state coupled among an energy source and a distal tip, under an embodiment.

In the drawings, the same reference numbers identify identical or substantially similar elements or acts. To easily identify the discussion of any particular element or act, the most significant digit or digits in a reference number refer to the Figure number in which that element is first introduced (e.g., element 108 is first introduced and discussed with respect to FIG. 1).

DETAILED DESCRIPTION

A tissue ablation system including numerous components and methods is described herein for encircling target tissue and generating tissue ablation volumes in various biological tissues. The biological tissue includes tissue of a variety of organs of the human body including the liver, spleen, kidney, lung, breast and other organs, but is not so limited. The tissue ablation device comprises an energy source and at least one trocar coupled to the energy source, the trocar having a body, a proximal end, and a distal end. The trocar carries an electrode array that comprises a plurality of electrodes, each electrode of the plurality of electrodes is configured to extend from the trocar when moved from a retracted state to a deployed state, and to have at least one radius of curvature in the deployed state so that the electrode array forms a series of shaped electrodes in the deployed state.

In the following description, numerous specific details are introduced to provide a thorough understanding of, and enabling description for, embodiments of the tissue ablation system. One skilled in the relevant art, however, will recognize that the tissue ablation system can be practiced without one or more of the specific details, or with other components, systems, etc. In other instances, well-known structures or operations are not shown, or are not described in detail, to avoid obscuring aspects of the tissue ablation system.

The devices of an embodiment are components of ablation systems primarily for use in unresectable cases. As such, the devices are indicated for the thermal coagulation and ablation of soft tissue including coagulative necrosis in solid organs and partial or complete ablation of nonresectable liver lesions. The devices use high speed radiofrequency (RF) ablation (HS-RFA) technology to achieve ablations in a fraction of the time of conventional RF systems, as described herein. The devices generate ablations by generating or creating an energy field that actually implodes into the treatment area. In a recent clinical trial, for example, the devices of an embodiment demonstrated the creation of a series of ablation zones as follows: a 3.5 cm diameter ablation was generated in approximately 3 minutes; a 5 cm diameter ablation was generated in approximately 5 minutes; a 7 cm diameter ablation was generated in approximately 12 minutes. Further, the bipolar tumor ablation devices of an embodiment are capable of creating up to 7 cm diameter ablation areas without the need for complicated fluid delivery systems or risky return electrodes.

During operation, accurate device placement is facilitated with an ultrasound guidance tool that allows the use of ultrasound to directly visualize, center and lock on the target area to produce optimal or near-optimal ablations. Unlike conventional ablation systems, the devices of an embodiment minimize or avoid tumor contact at all stages in the procedure, thereby minimizing or avoiding the risk of tumor seeding. Furthermore, the devices use standard radiofrequency generators without the need for complicated pumps, tubes, and/or fluids. Furthermore, embodiments of the devices described herein, as a result of their bipolar configuration, do not use return electrodes or grounding pads and have more efficient energy distribution at the tumor site so lower power settings can be used in comparison with conventional monopolar RF systems. This allows for safer procedures with lower power settings, no skin pads and no skin pad burns.

In contrast to conventional multiple-electrode RFA systems and to overcome drawbacks of such systems, the tissue ablation system of an embodiment comprises a trocar and an electrode array. The trocar of an embodiment includes a distal end and a lumen extending along a longitudinal axis of the trocar. Additionally, the trocar includes one or more orifices positioned along the longitudinal axis. The electrode array of an embodiment comprises multiple electrodes. The electrodes, when in a retracted state, are positioned in the trocar lumen. The electrodes are deployed to a deployed state through a set of orifices of the orifices in the trocar. Each electrode has at least one radius of curvature in the deployed state so that the electrode array forms a series of shaped electrodes in the deployed state, as described in detail herein.

The tissue ablation device of an alternative embodiment comprises a trocar and an electrode array. The trocar of an embodiment includes a distal end and a lumen extending along a longitudinal axis of the trocar. Additionally, the trocar includes a number of orifice sets positioned along the longitudinal axis and in communication with the trocar lumen. The electrode array of an embodiment comprises a number of electrode sets. The electrode sets include a plurality of electrodes. The electrode sets are deployed to a deployed state through the orifice sets, and electrodes of the electrode sets have at least one radius of curvature in the deployed state so that the electrode array in the deployed state forms at least one set of shaped electrodes.

The tissue ablation device of another alternative embodiment comprises more than one ablation device. Each ablation device of an embodiment comprises a trocar and an electrode array. The trocar of an embodiment includes a distal end and a lumen extending along a longitudinal axis of the trocar. Additionally, the trocar includes one or more orifices positioned along the longitudinal axis. The electrode array of an embodiment comprises multiple electrodes. The electrodes, when in a retracted state, are positioned in the trocar lumen. The electrodes are deployed to a deployed state through a set of orifices of the orifices in the trocar. Each electrode has at least one radius of curvature in the deployed state so that the electrode array forms a series of shaped electrodes in the deployed state, as described in detail herein.

The tissue ablation device of yet another alternative embodiment comprises more than one ablation device and a bridge. Each ablation device of an embodiment comprises a trocar and an electrode array. The trocar of an embodiment includes a distal end and a lumen extending along a longitudinal axis of the trocar. Additionally, the trocar includes one or more orifices positioned along the longitudinal axis. The electrode array of an embodiment comprises multiple electrodes. The electrodes, when in a retracted state, are positioned in the trocar lumen. The electrodes are deployed to a deployed state through a set of orifices of the orifices in the trocar. Each electrode has at least one radius of curvature in the deployed state so that the electrode array forms a series of shaped electrodes in the deployed state, as described in detail herein.

The bridge of an embodiment includes a number of receptacles that receive the ablation devices. The bridge holds or secures each of the ablation devices in a fixed position relative to every other ablation device being used with the bridge.

The device configurations of an embodiment define the outer surface of the target tissue area. The direct current flow produced by the device through the region between the outside boundaries of the target tissue area causes heating in the target tissue as a result of the current flow instead of from thermal conduction. Conduction in the target tissue rounds out the corners outside of the electrodes (current path). Thus, the device configuration of an embodiment defines the outer boundary of the target tissue directly with the electrodes and then creates a direct path through the target tissue (between the electrodes) by which current flows and heats the target tissue.

Consequently, the device of an embodiment produces complete ablations because the ablations are not subject to quick roll off of the energy density. This result is due to the electrode configuration, as described herein. The electrode configuration includes an electrode surface area that is maximized through the use of large flat wire, in an embodiment, which increases the surface area relative to much smaller wires flat or round. The electrode spacing of the individual electrodes is achieved within the same polarity so that larger amounts of tissue can be engage. The electrode configuration or geometry also makes use of electrode "rings" (also referred to herein as a "shape", "ellipse", and/or "circle"), which have the effect of "long" electrodes having a large surface area and therefore large tissue engagement area. Thus, the result of the combination of electrode surface area, individual electrode spacing, and overall device configuration or geometry is complete ablations.

The interface between the electrode surface and the tissue in RFA is analogous to a fuse, or "fusible link". The electrodes of the device of an embodiment are configured to enclose the target tissue area so that the ablation procedure progresses from the outside to the inside of the target tissue area. This electrode configuration increases the amount of tissue surface area that can be engaged by the device because a larger amount of tissue is "enclosed" by the electrodes when compared to a conventional device which places the electrodes at or near the center of the target tissue area. This configuration, in effect, provides a larger "fuse" for receiving the energy, thus allowing for the delivery of more energy (current), along with a relatively slower time constant or ramp of the increase in impedance as the procedure progresses. The device of an embodiment therefore functions to maximize the current rating on this fuse without making the physical size unmanageable.

The device of an embodiment generally minimizes or prevents the situation in which the tissue near a first electrode ablates faster than the tissue near a second electrode (e.g., this can happen when a vessel is close to the second electrode, thereby creating a larger heat sink effect in the vicinity of the second electrode). This is because the bipolar electrode configurations of an embodiment become self-directing as ablation progresses and the target tissue desiccates. In considering this self-directing effect, the same amount of current flows everywhere in the target tissue when the tissue density throughout the target tissue is the same. As target tissue heats and subsequently desiccates, the impedance of the target tissue increases and the amount of current flowing is reduced as a result of the increased impedance or resistance. The appearance of desiccated tissue and corresponding impedance increase causes the current flow to begin to redistribute and increase in other less desiccated regions of the target tissue. This process continues until either all tissue has been desiccated or the amount of current is too high for the remaining electrode area and the system impedes out locally. By having a larger "fuse: the electrodes are then capable of delivering the larger amount of energy without prematurely charring the tissue around the electrodes and halting the ablation.

As described in detail herein, the device configuration of an embodiment defines the outer surface of the target tissue area which results in a larger tissue area through which current can be delivered. This minimizes or eliminates the reliance on conduction at the outer surface to desiccate tissue as the device configuration causes all tissue bounded by the electrodes (inside the defined area) to receive full power from the device. This results in an improvement in the device effectiveness because the most difficult heat sinks are those at the outer edge of the target tissue area because conventional devices heat from inside to outside the target tissue area, thereby relying on conduction at the outer surface. Additionally, the outer surface is where the malignancy or malignant tissue (e.g., cancer) is most active and growing. Thus, the device of an embodiment improves effectiveness, desiccates tissue of the target tissue in less time than conventional ablation devices, and is less susceptible to heat sink effect than conventional devices.

This outside-to-inside current flow and heating effect is in contrast to conventional ablation devices that use inside-to-outside heating. The inside-to-outside heating of conventional devices generally delivers energy to the core or center of the target tissue using one or more electrodes (antennas) placed in the center region of the target tissue. Consequently, the inside-to-outside heating relies on thermal conduction to heat tissue away from the center region. However, thermal conduction is adversely affected by rapid energy dispersion (according to the inverse square law). Furthermore, thermal conduction directly relates to tissue density of the target tissue, and tissue density is typically very non-uniform and unable to be ascertained in advance of the procedure. This variation in tissue density is further complicated since these devices are placed into the center of the target area directly contacting the tumor, and since tumors vary greatly from one to another, these variations dramatically alter and limit both the physical and electrical contact between the tissue and the electrode(s). Moreover, the energy field strength is difficult to control in the target tissue when radiating energy from one or more antennas located at the center of the region. These adverse factors make ablation size and shape very difficult to control relative to the ablation size and shape produced by the device of an embodiment. Thus, the inside-to-outside heating provided by conventional devices is often ineffective and results unpredictable.

The inside-to-outside heating of the conventional devices attempts to create a core of hot tissue which, through thermal conduction, will radiate or disperse the heat to the outer portion of the target tissue volume. However, only in the best of conditions is the energy delivered via thermal conduction sufficient to create a complete and nominal sized ablation. When any increase in thermal losses (heat sinks) occurs, either in general (such as high central venous pressure), or localized (blood vessels), the resulting ablations are undersized, misshaped, and/or malformed. This can result in viable cancer cells remaining undetected after their treatment. This has been demonstrated by several published studies noting a wide range of viable cancer cells remaining after the completion of an inside-to-outside ablation.

Another deficiency with the inside-to-outside heating is the dramatic loss of energy density as the distance from the electrodes increases. Absent sufficient energy per cubic centimeter of tissue, heating of the tissue cannot occur. As the desired ablation size increases the volume and surface area of the ablation increases geometrically. For example the surface area of a 3.5 cm ablation is 38 square cm and the volume is 22 cubic cm. When doubling the ablation diameter to 7 cm, the surface area increases by a factor of four becoming 154 square cm and the volume increases by a factor of eight becoming 179 cubic cm. With a fixed maximum amount of energy that can be delivered, the density of energy will decrease as the area and volume increase. For a sphere the increase in area and volume occurs at the outer portion of the target ablation. In this area the other devices have the least amount of energy density and lowest ability to create any heat. This is particularly an issue since it is known that the core of larger tumors is often dead and the blood supply (heat sink) is feeding the outer edge where the viable tumor continues to grow and expand. This means that the area containing the viable tumor is also the area where conventional inside to outside devices are the least effective and unable to respond to additional heat loss.

For these reasons, a conventional device using inside-to-outside heating is unable to overcome the heat sink of larger ablations because it cannot deliver enough energy from the electrodes to generate the heat needed to overcome any large amount of heat loss from either the heat loss due to a larger surface area or due to the heat loss from heat sinks such as vascular structures. Some conventional devices, in an attempt to overcome the ineffective energy density they produce, use a staged deployment of the device electrodes. These devices rely on thermal conduction and thermal momentum from the heated tissue at the core to desiccate tissue. These devices operate by using an initial partial deployment to engage only a small amount of tissue, thereby making the tissue easy to heat. The theory is that if the electrodes are deployed in stages, then the heating of tissue during each stage will be easier to effect and will provide a more constant heat profile at the core. Thermal momentum of the heated core tissue is then relied upon to produce heating of tissue peripheral to the core in the target tissue volume. The device remains deficient, however, because as the electrodes of this device are expanded, the amount of tissue and heat sink becomes too large for the small amount of energy the device can deliver. Even if the conventional inside-to-outside devices had the ability to deliver a large amount of energy to better overcome their poor energy density, they would then produce unpredictable ablation sizes and shapes varying with the ever changing thermal conditions of each patient. A review of the United States Food and Drug Administration (USFDA) database demonstrates that the patient deaths associated with the use of conventional RFA were the result of the unintentional ablation of other non-targeted tissue.

The device configuration of an embodiment overcomes numerous issues associated with conventional RFA devices through the use of the outside to inside heating configuration and, consequently, high energy transfer to the target tissue. The high energy transfer allows the device to overcome larger heat sinks, while defined energy envelope controls potential runaway by keeping the energy confined to the targeted area. This allows all of the delivered energy to go into the target area and instead of radiating outward. The device configuration of an embodiment also provides a more uniform energy density with the energy being delivered to the critical area first with a high energy density. The energy produced by the electrodes passes through the target tissue as it passes between electrodes, and this produces and maintains a more uniform energy density relative to conventional devices. End point measurements of impedance are also more reliable since virtually everything being measured is the targeted tissue itself. This combination of high energy delivery to overcome heat sinks, energy delivery at the surface of the target tissue volume, energy focused only into the target area, as well as a high and more uniform energy density helps the devices of an embodiment to produce faster, more uniform, and more repeatable ablations.

The device and methods of an embodiment use impedance in the target tissue to determine an endpoint of the procedure. Impedance is used by controlling the procedure according to the impedance "roll off" of the target tissue. The use of impedance allows the ablation to continue until everything within the scope of the lesion is coagulated, regardless of time or temperature.

A number of factors, including temperature, impedance, and time, are to a degree interrelated but interdependent during the procedure of an embodiment. The actual goal with all of these devices is to achieve cell death, and more specifically cell death of the tumor plus some margin around the tumor. Since RFA uses heat, this cell death is achieved by increasing the tissue temperature to a lethal level for the required amount of time. Time is required because cell death occurs when an elevated temperature is maintained for a minimum amount of time. If cell death is plotted as a function of temperature and time, it can be seen that cell death occurs almost instantaneously at higher temperatures. At a slightly lower temperature it requires a few seconds, lower still it takes several seconds, still lower and seconds turn into minutes, until finally the tissue will never die regardless of length of exposure.

Impedance, which is the resistance to the flow of electricity in the target tissue at a particular frequency, is not a direct measure of cell death. However, after heating tissue to an appropriate temperature for a period of time sufficient to cause the moisture to be driven out of the tissue, the impedance increases to a point that indicates cell death has occurred. Electricity or electrical energy can be applied to tissue, resulting in high impedance, using four general types of application. The first application is a lighting bolt discharge that vaporizes (removes) tissue and leaves a thin charred region in the resulting crater. This is typical of electrocautery at very high power (voltage) levels and is not typical of RFA. A second application is superficial char around an electrode which causes a very high impedance in the charred tissue (and cell death) while normal tissue remains beyond the charred tissue around the electrode. A third application involves the complete desiccation of tissue in a region resulting in the tissue death in the entire region. A fourth application involves a combination of the second and third applications.

Some conventional devices make a few temperature measurements at the very tip of the device electrodes. The operational theory associated with these devices is to raise the temperature at the electrodes high enough and long enough to imply that the temperature between the electrodes, which is not heated or measured, would get hot enough for a long enough period of time to create cell death. For very small ablations this can provide acceptable results, but the procedure is time consuming when only smaller amounts of power can be delivered without causing superficial tissue charring. Another weakness of this approach is that the clinician has no information about the temperature in the tissue anywhere other than at the very tip of the electrodes that include thermocouples. Since the number of electrodes with thermocouples is very limited, the reliability of the measurement through the ablation is also poor. In addition, thermocouples themselves are typically only accurate to a few degrees centigrade and can have a large amount of additional error when used with RF.

A "cool down" theory was also derived for use with conventional device in order to address the weaknesses of this procedure. Using the cool down theory, a clinician turns off the power at the end of the ablation and measures the temperature in the tissue after waiting approximately 30 seconds, and this wait period allows the temperature measured in the tissue to equalize to an equilibrium temperature. It was then implied that the entire target tissue area had reached the equilibrium temperature and that cell death had resulted. The problem with this theory is that the time-temperature history of a majority of the tissue remains unknown. Also, the presence of any heat sinks (e.g., vessels, etc.) in or near the target tissue regions that may have altered the final temperature is unknown, as is the period of time during which the target tissue was at the equilibrium temperature (the time-temperature profile). The accuracy of these methods decreases further as the ablations become larger since the distance between thermocouples increases. As the volume of tissue increases the amount of tissue in which the temperature is unknown increases.

As a further refinement to the above procedure, thermocouples were placed in conventional electrodes having a non-electrically conductive coating (referred to as passive electrodes). The coating, however, also introduces additional error into the temperature measurements. These passive electrodes were arranged to be in the middle of the active electrodes of conventional devices in an attempt to read the assumed point of lowest temperature. Again everything is based on assumptions and implications. In this case the assumption was that the target region is completely homogenous and thermally the same everywhere, which is seldom true. As soon as this assumption is violated the center between active electrodes is no longer the point of lowest temperature. Once again the ablation relies on faulty data in an effort to imply a desired result of cell death.

Attempts have been made with conventional devices to use impedance to determine a procedural endpoint. These conventional attempts to use impedance required a bulk impedance measurement, and implied tissue death in the target tissue volume from the bulk tissue measurement. This method was somewhat independent of ablation time in that an appropriate initial power was selected and applied, and power delivery continued until full tissue desiccation occurred. This initial power level must be low enough to stay within the energy delivery limits of the device (electrode charring), but high enough to eventually overcome the thermal heat sinks and desiccate the tissue. A complex control algorithm is followed by the clinician-user, and the procedure includes repeated ablation cycles to ensure that the impedance measurement represents the full volume of desiccated tissue and not superficial char around the electrodes. To help with this, the generators used in these procedures lower the delivered power when the impedance begins to increase to help fully saturate the target tissue. Although these systems attempt to make bulk impedance measurements, with a mono-polar device the only measurement that can be made is one that includes the target tissue plus the impedance of all the tissue between the target volume and the volume of tissue to return electrodes (e.g., all tissue between the device electrodes located in the torso, for example, and return electrodes on the patient's legs). Thus, this method also suffers from large uncertainty in the impedance measurements, resulting in small localized areas of viable tissue which have not been ablated and are unable to be detected.

The desired result of an ablation procedure using the device of an embodiment is bulk desiccation of target tissue. The desiccation is confirmed in an embodiment by observing the slow and steady increase in impedance (loss of electrical conduction, loss of moister, dead tissue). Point temperature measurements are not, however, effective in confirming desiccation because they provide no information about what is happening at any other location in the target tissue other than the point of the temperature measurement. It is very easy to create desiccated tissue around a pin-point and not kill tissue outside of the immediate area. Furthermore, cool-down temperatures are also not useful in confirming tissue desiccation because they are particularly unreliable as the ablation volume becomes large.

In contrast to impedance values provided by conventional devices, the impedance measurements taken in the target tissue defined by the device of an embodiment have a relatively higher accuracy. The electrode configuration of the device of an embodiment defines the target tissue area in which desiccation is desired and, therefore, defines the impedance measurement area of interest. The bipolar configuration of the device of an embodiment results in the electrodes being positioned closer to each other when compared to a monopolar device (e.g., large distance between device electrodes and ground pads on patient's legs provides poor results because of the uncertainty involved with the large volume of intervening tissue). Further, the larger ratio of electrode surface area to volume of target tissue provided by the device of an embodiment provides for more accurate impedance measurements.

Figure 2:
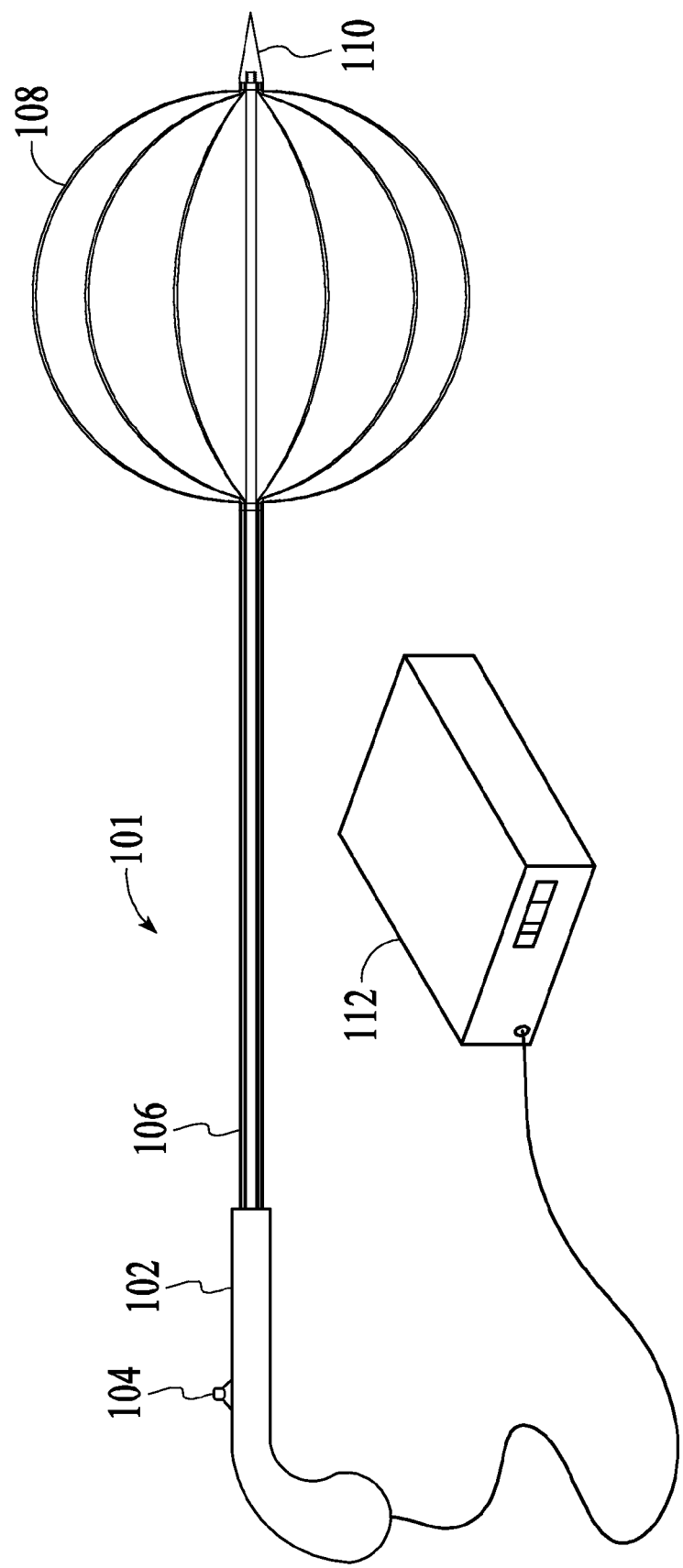
FIG. 2 is a tissue ablation device including a hand piece, a deployment slider, a delivery member/tube, and a plurality of energy conduits in a deployed state coupled among an energy source and a distal tip, under the embodiment of FIG. 1.

FIG. 1 is a tissue ablation system 100, under an embodiment. The tissue ablation system 100 includes a tissue ablation device 101 coupled to at least one energy source 112. The tissue ablation device 101 includes a hand piece 102, a deployment slider 104, a delivery member/tube 106, a plurality of energy conduits 108, and a distal tip 110, under an embodiment. The energy conduits 108, also referred to herein as electrodes 108, are in a retracted state, but are not so limited. FIG. 2 is a tissue ablation device with the energy conduits 108 in a deployed state, under an embodiment. The tissue ablation device 101 can also include other components as known in the art and as appropriate to procedures including the tissue ablation device 101.

The components of the tissue ablation system 100 are described in turn with reference to FIG. 1 and FIG. 2. The hand piece 102 of the tissue ablation device 101 includes a handle by which the user grips the tissue ablation device 101. The hand piece 102 provides a coupling between the energy source 112 and one or more of the energy conduits 108 which may or may not be coupled to at least one of the hand piece 102 and the energy source 112. The deployment slider 104 or advancement mechanism 104, which in an embodiment is integral to the hand piece 102, deploys or retracts the energy conduits 108 upon actuation.

The tissue ablation device 101 also includes a delivery member/tube 106 that supports placement of the energy conduits 108 in the target tissue, but is not so limited. The delivery member/tube 106 is formed using material that is at least one of electrically conductive, conditioned, and coated to allow for electrical conductivity via the electrodes. As an example, the delivery member/tube 106 is formed using at least one of stainless steel, nickel titanium, alloys, and plastics including Ultem, Polycarbonate, and Liquid crystal polymer, but is not so limited. The delivery member/tube 106 has a diameter approximately in a range of 0.05 to 0.5 inches, and has a length approximately in a range of 0.1 to twenty (20) inches as appropriate for extension into a body region appropriate to the treatment procedure. As one example, the delivery member/tube 106 of an embodiment has a diameter of between approximately 0.08 and 0.3 inches and a length between approximately two (2) and twelve (12) inches.

The energy conduits 108 while configured appropriately for insertion into particular tissue types, are formed from one or more materials and have a shape, size, and pattern that supports coupling to the target tissue and allows the energy conduits 108 to deliver sufficient energy to ablate the target tissue. The energy conduits 108 include materials selected from among conductive or plated metals and/or plastics, super alloys including shape memory alloys, and stainless steel, to name a few. The energy conduits 108 comprise nickel titanium alloy, for example, but can be formed from any number/combination of materials including stainless steel, nickel titanium, and various alloys.

The energy conduits 108 of an embodiment, which collectively may be referred to as an electrode array 108, can have many different sizes (including lengths and diameters) depending upon the energy delivery parameters (current, impedance, etc.) of the corresponding system. The use of energy conduits 108 having different diameters allows for balancing of energy/energy density in the target tissue. Therefore, the use of energy conduits 108 having different diameters provides a means of control over energy balancing in the target tissue in addition to the spacing between the energy conduits 108. An outside diameter of one or more of the energy conduits 108 of an embodiment is approximately in the range of 0.005 to 0.093 inches, but is not so limited. Further, the energy conduits 108 of an embodiment have lengths sufficient to generate or create an ablation diameter approximately in the range of one (1) to fifteen (15) centimeters (cm), but are not so limited. As one example, the energy conduits 108 of an embodiment have an outside diameter between approximately 0.01 and 0.025 inches and lengths sufficient to generate or create an ablation diameter approximately in the range of three (3) to nine (9) centimeters (cm).

The energy conduits 108 of various alternative embodiments can include materials that support bending and/or shaping of the energy conduits 108. Further, the energy conduits 108 of alternative embodiments can include non-conducting materials, coatings, and/or coverings in various segments and/or proportions along the shaft of the energy conduits 108 as appropriate to the energy delivery requirements of the corresponding procedure and/or the type of target tissue The energy source 112 of an embodiment (also referred to as a generator 112 or electrical generator 112) delivers pre-specified amounts of energy at selectable frequencies in order to ablate tissue, but is not so limited. The energy source 112 includes at least one of a variety of energy sources including electrical generators operating within the radio frequency (RF) range. More specifically, the energy source 112 includes an RF generator operating in a frequency range of approximately 375 to 650 kHz and at a current of approximately 0.1 to 5 Amps and an impedance of approximately 5 to 100 ohms, but is not so limited. As an example, the energy source 112 of an embodiment operates at a frequency approximately in the range of 400 kHz to 550 kHz and at a current of approximately 0.5 to four (4) Amps, but is not so limited. Variations in the choice of electrical output parameters from the energy source 112 to monitor or control the tissue ablation process may vary widely depending on tissue type, operator experience, technique, and/or preference.

The tissue ablation system 100 can include any number of additional components like, for example, a controller (not shown) to semi-automatically or automatically control delivery of energy from the energy source 112. The controller can, for example, increase the power output to the energy conduits 108, control temperature when the energy conduits 108 include temperature sensors or when receiving temperature information from remote sensors, and/or monitor or control impedance, power, current, voltage, and/or other output parameters. The functions of the controller can be integrated with those of the energy source 112, can be integrated with other components of the tissue ablation system 100, or can be in the form of stand-alone units coupled among components of the tissue ablation system 100, but are not so limited.

Moreover, the tissue ablation system 100 can include an operator display (not shown) that provides a display of heating parameters such as temperature for one or more of the energy conduits 108, impedance, power, current, timing information, and/or voltage of the energy source 112 output. The functions of the display can be integrated with those of the energy source 112, can be integrated with other components of the tissue ablation system 100, or can be in the form of stand-alone units coupled among components of the tissue ablation system 100, but are not so limited.

In operation, a user advances the deployment slider 104, and in response the energy conduits 108 are forced, or in the case of a pre-shaped energy conduits, released from the retracted state to the deployed state. The shape of the deployed energy conduits can, as shown in FIG. 2, form a series of approximately semi-spherical segments that, when taken together, form the outline of a sphere. The tissue ablation device generates a spherical volume of ablated tissue upon application of energy to the deployed electrodes.

Figure 3:
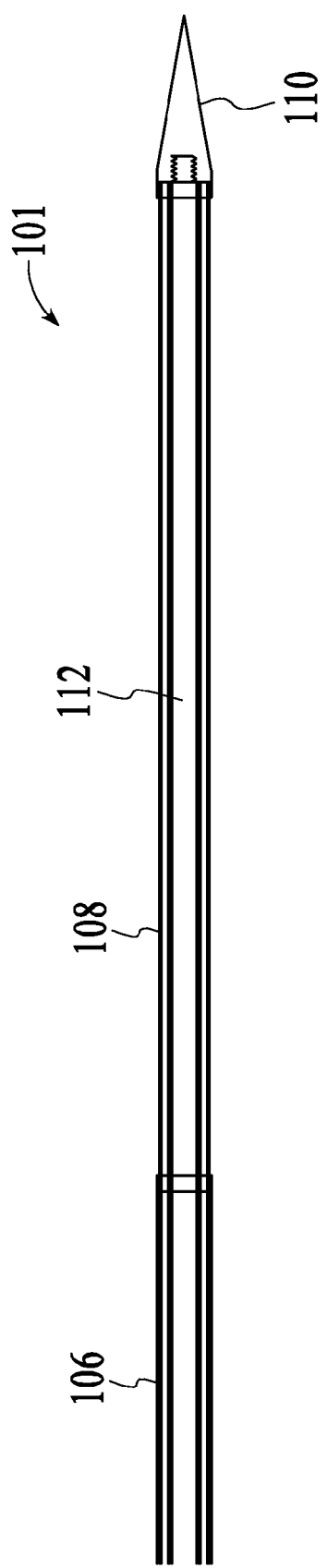
FIG. 3 is a distal portion of a tissue ablation device including a delivery member/tube and a plurality of energy conduits in a retracted state, under the embodiment of FIG. 1.

FIG. 3 is the distal portion of a tissue ablation device 101 including a delivery member/tube 106, a deployment member or rod 112, a plurality of energy conduits 108 in a retracted state (two energy conduits are shown for simplicity, but the embodiment is not so limited), and a distal tip 110, under the embodiment of FIG. 1. The energy conduits 108 are coupled, either individually or collectively, to an energy source or generator (not shown). When the energy conduits 108 are in the retracted state, the distal portion of the tissue ablation device presents a very streamline profile well suited to piercing tissue and advancement/placement in/near an area which might contain a malignant or non-malignant tumor. By piercing the tumor the distal tip can be placed just beyond the tumor.

Figure 4:
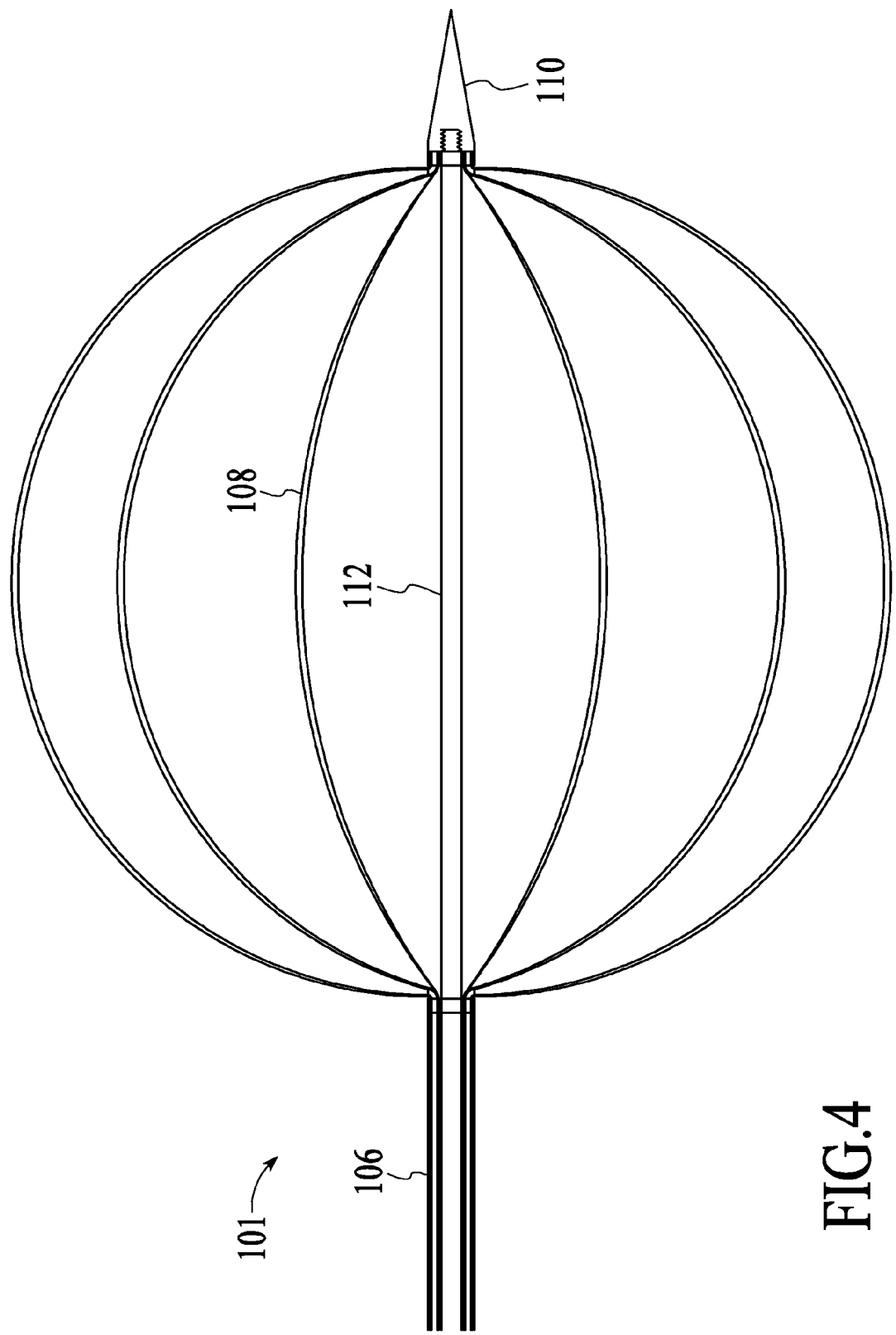
FIG. 4 is a distal portion of a tissue ablation device including a delivery member/tube and a plurality of energy conduits in a deployed state, under the embodiment of FIG. 1.

FIG. 4 is the distal portion of a tissue ablation device 101 including a delivery member/tube 106, a deployment member or rod 112, a plurality of energy conduits 108 in a deployed state, and a distal tip 110, under the embodiment of FIG. 1. The energy conduits 108 are coupled, either individually or collectively, to an energy source or generator (not shown). Following placement of the distal portion of the tissue ablation device in the target tissue as appropriate to the corresponding medical procedure, the user advances the deployment slider (not shown) to deploy the energy conduits 108, thus fully encompassing the volume of tissue desired to be ablated.

Regarding deploying of the energy conduits 108, some or all of the energy conduits 108 can be deployed in response to advancement of the deployment slider. For example, all energy conduits 108 of an embodiment are deployed simultaneously in response to advancement of the deployment slider. As another example, one set of energy conduits 108 can be deployed to form a sphere having a first diameter while another set of energy conduits 108 can be deployed to form a sphere having a second diameter. Other alternative embodiments can use additional deployment schemes known in the art.

The energy conduits 108 of an embodiment deliver radio frequency (RF) current to the target tissue and, as such, can be of alternating electrical polarity. The alternating polarity series of energy conduits includes various series combinations of alternating polarities. For example, in an embodiment using ten (10) energy conduits, the alternating polarity is: positive polarity (+), negative polarity (−), +, −, +, −, +, −, +, −. An alternative polarity series is: +, +, −, −, +, +, −, −, +, +. Another alternative polarity series is: −, −, +, +, −, −, +, +, −, −. Yet another alternative polarity series is: +, +, +, +, +, −, −, −, −, −. These examples are only illustrative of possible polarity configurations, and the tissue ablation system 100 described herein is not limited to ten (10) electrodes or to these alternating polarity configurations.

The energy conduits of an alternative embodiment conduct electricity of a single electrical polarity, while the deployment rod 112 conducts electricity having an opposite polarity to that of the energy conduits. In still another alternative embodiment, the deployable energy conduits are switched between the same electrical polarity with the deployment rod being the other and alternating polarity between the deployable energy conduits. In yet another alternative embodiment, the deployment rod and deployable energy conduits are of a single electrical polarity and one or more secondary grounding pads are used therewith to provide an opposite polarity member.

Various alternative embodiments can simultaneously use any number of energy conduits in a procedure in order to form volumes of ablated tissue having shapes and sizes appropriate to the treatment procedure. Numerous alternatives would be recognized by those skilled in the art in view of the tissue ablation device described herein.

Figure 5:
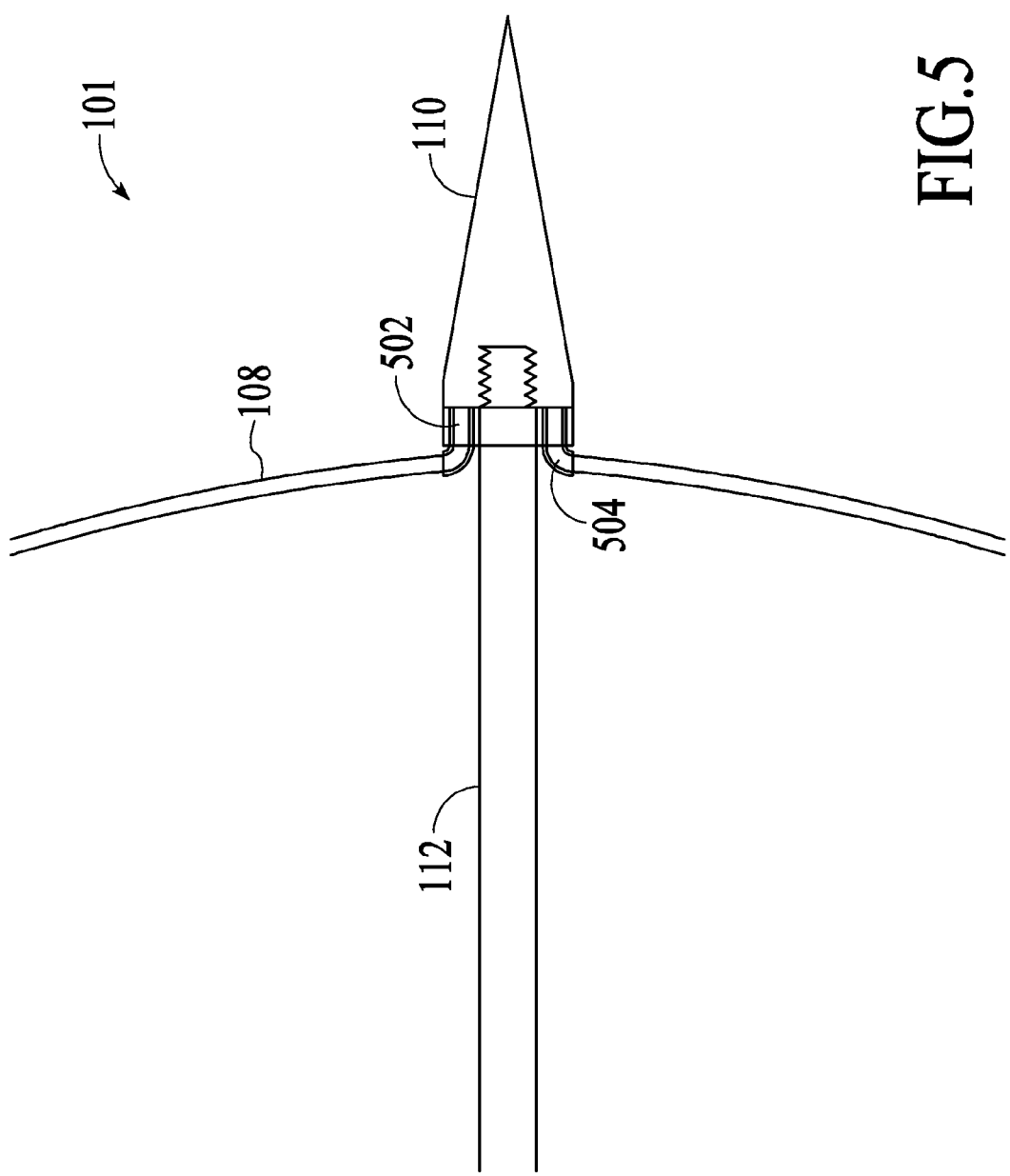
FIG. 5 shows an enlarged view of the distal portion of a tissue ablation device including a center deployment rod and a plurality of energy conduits in a deployed state, under the embodiment of FIG. 1.

FIG. 5 shows a distal region or portion of a tissue ablation device 101 including a center deployment rod 112, a plurality of energy conduits 108 in a deployed state (two energy conduits are shown for simplicity, but the embodiment is not so limited), conduit insulators 504, and a distal tip 110, under the embodiment of FIG. 1. In support of delivering electrical energy of alternating polarity via the energy conduits 108, the conduit insulators 504 mechanically couple the distal ends of the energy conduits 108 while maintaining electrical insulation between each of the energy conduits 108. In this tissue ablation device the deployable energy conduits 108 are coupled to the conduit insulators 504. The combination of the energy conduits 108 and the conduit insulators 504 is coupled to a non-electrically conductive retaining disk 502 that is coupled to an electrically conductive deployment member 112. Also connected to the deployment member 112 is the electrically conductive distal tip 110 that, in this embodiment, is suitable for piercing tissue. Advancing the deployment slider causes the deployable energy conduits or electrodes 108 to experience a compressive load. As this force increases beyond the column strength of the deployable energy conduits 108, the energy conduits 108 buckle and deploy outward in a controlled fashion.

Alternatively, the energy conduits 108 can be pre-formed to a desirable shape when fabricated of a suitable material such as a nickel titanium (NiTi) alloy. Using the pre-formed electrodes, advancement of the deployment slider permits the deployable electrodes to return to their preformed shape. The application of a small amount of energy such as RF current can help to facilitate the deployment of the electrodes through the tissue.

Figure 6:
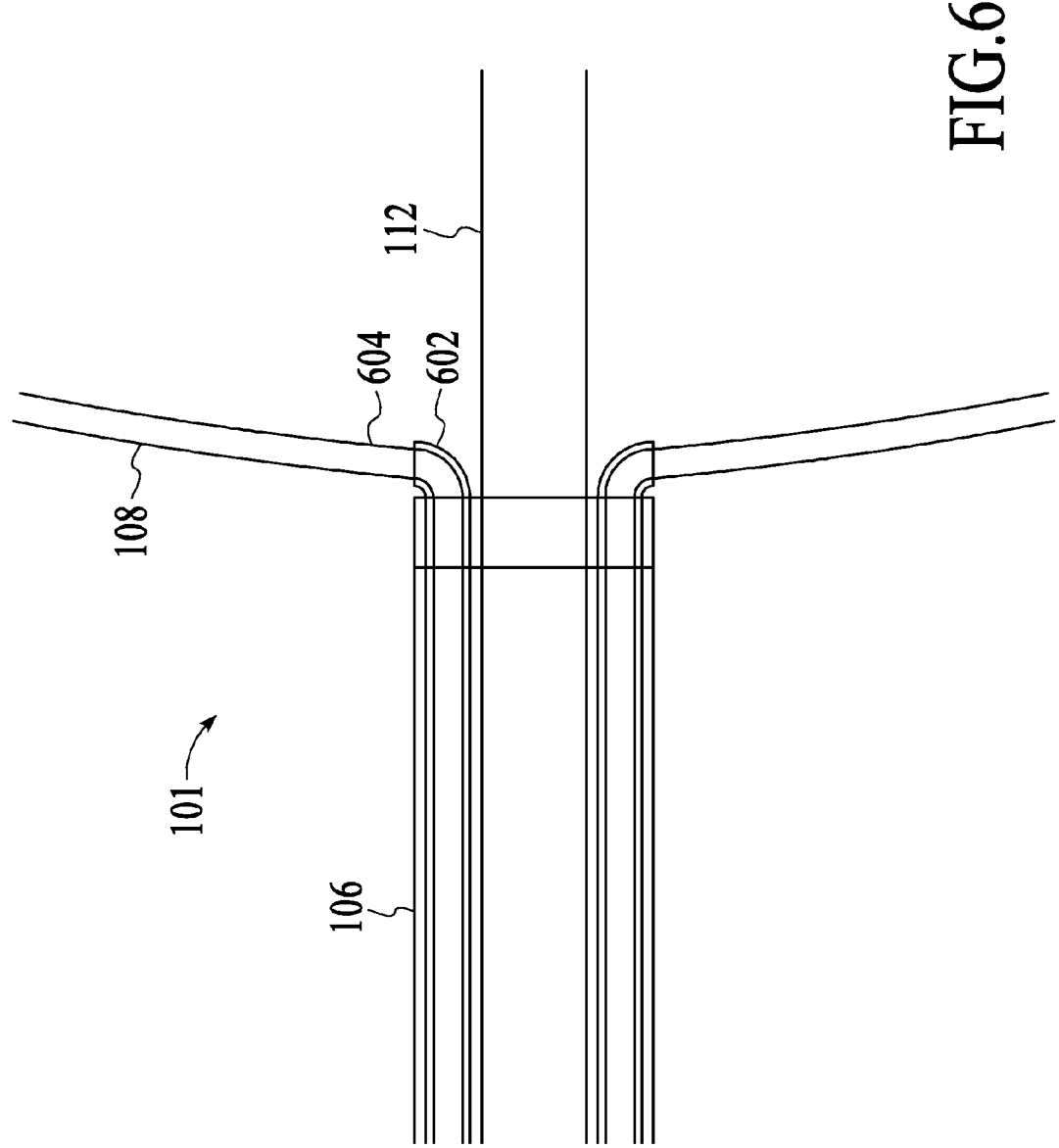
FIG. 6 shows an enlarged view of the mid-section of a tissue ablation device including a center deployment rod and a plurality of energy conduits in a deployed state, under the embodiment of FIG. 1.

FIG. 6 shows a mid-section of a tissue ablation device 101 including a delivery member/tube 106, a deployment member 112, and a plurality of energy conduits 108 in a deployed state (two energy conduits are shown for simplicity, but the embodiment is not so limited), under the embodiment of FIG. 1. The proximal end 604 of the energy conduits 108 couples to an electrical insulator 602 or insulating material 602, but is not so limited.

Figure 7:
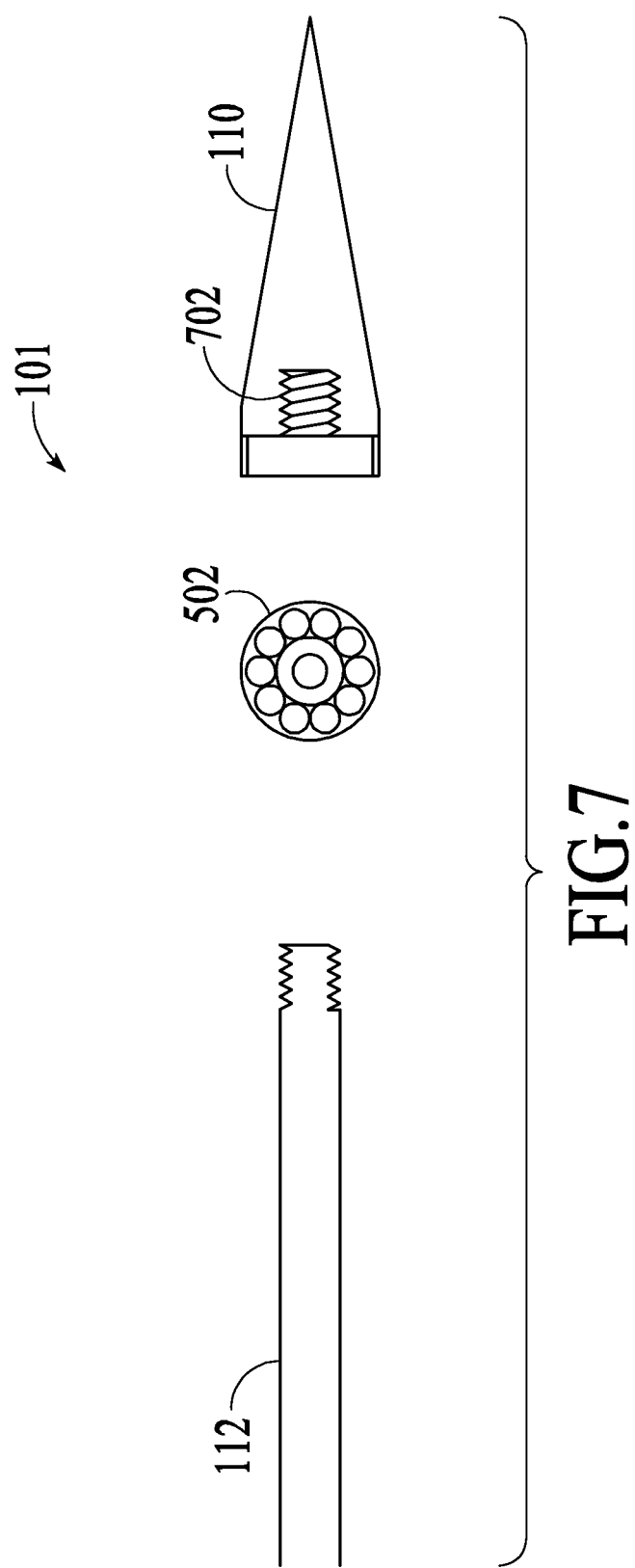
FIG. 7 shows an exploded view of the distal end of a tissue ablation device including a center deployment rod along with a rotated side view of the delivery member/tube including a plurality of energy conduits and deployment rod, and a distal tip, under the embodiment of FIG. 1.

FIG. 7 shows an exploded view of a distal region of a tissue ablation device 101 including a deployment member 112, a distal tip 110, and a rotated side view of an energy conduit retaining disk 502, under the embodiment of FIG. 1. Although a variety of methods exists to couple the components of the tissue ablation device 101 at the distal end, one such method is a simple screw thread 702 configured to accept a distal end of the deployment member 112. Alternatively, a press or interference fit between mating parts or the use of various adhesives can also be used. The retaining disk 502, as described above with reference to FIG. 5, is configured couple to the deployment member 112 and the distal tip 110.

Figure 8:
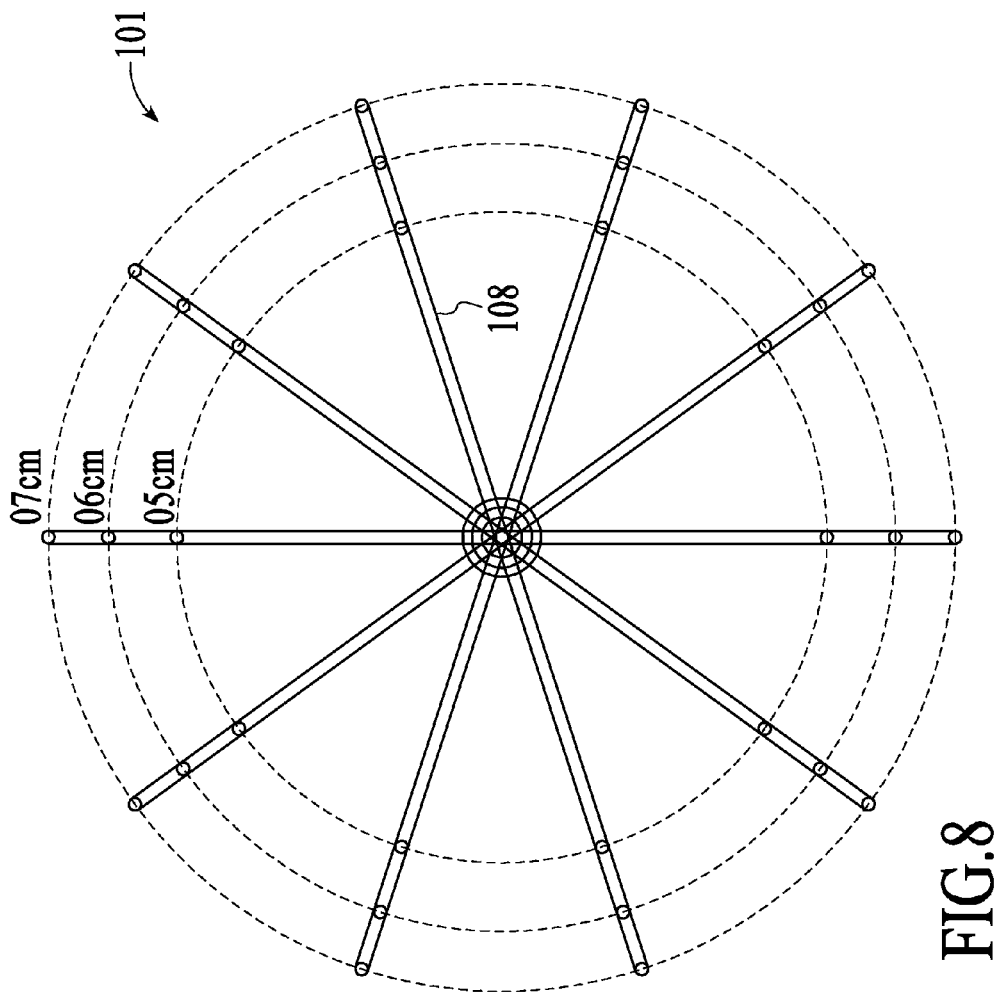
FIG. 8 is an end view of a plurality of deployed energy conduits having diameters of 5, 6, and 7 centimeters (cm), under the embodiment of FIG. 1.

FIG. 8 is an end view of a tissue ablation device 101 with deployed energy conduits 108 forming spheres having diameters of approximately 5, 6, and 7 centimeters (cm), under the embodiment of FIG. 1. The tissue ablation device 101 of an embodiment provides approximately uniform spacing among the energy conduits 108, but alternative embodiments may support any number/combination of energy conduit 108 configurations. The tissue ablation device 101 of an embodiment supports a variety of spherical deployment sizes by providing control over the extent to which the deployable energy conduits are deployed via the deployment slider, but is not so limited.

Figure 9:
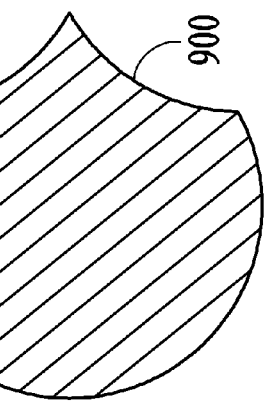
FIG. 9 is a cross-section of an energy conduit configured for at least one of cutting, separating, and parting tissue as it is pressed or forced against the tissue, under an embodiment.

FIG. 9 is a cross-section of an energy conduit 900 configured for at least one of cutting, separating, and parting tissue as it is pressed or forced against the tissue, under an embodiment. The energy conduit 900 is used to form the energy conduits 108 described above with reference to FIG. 1. As the energy conduits 900 are advanced from the retracted state (FIG. 3) to the deployed or expanded state (FIG. 4), the energy conduits 900 penetrate or separate the surrounding tissue. This penetration is accomplished in one embodiment using energy conduits that have a geometry suited for separating or cutting the surrounding tissue. The penetration of tissue by the energy conduits 900 in an alternative embodiment is accomplished with the application of energy, for example RF energy, to the energy conduit 900 in order to facilitate cutting through the tissue during advancement of the energy conduits. Another alternative embodiment includes the use of both an energy conduit 900 having a cutting geometry along with the application of a suitable electrical energy to the energy conduit 900.

Figure 10:
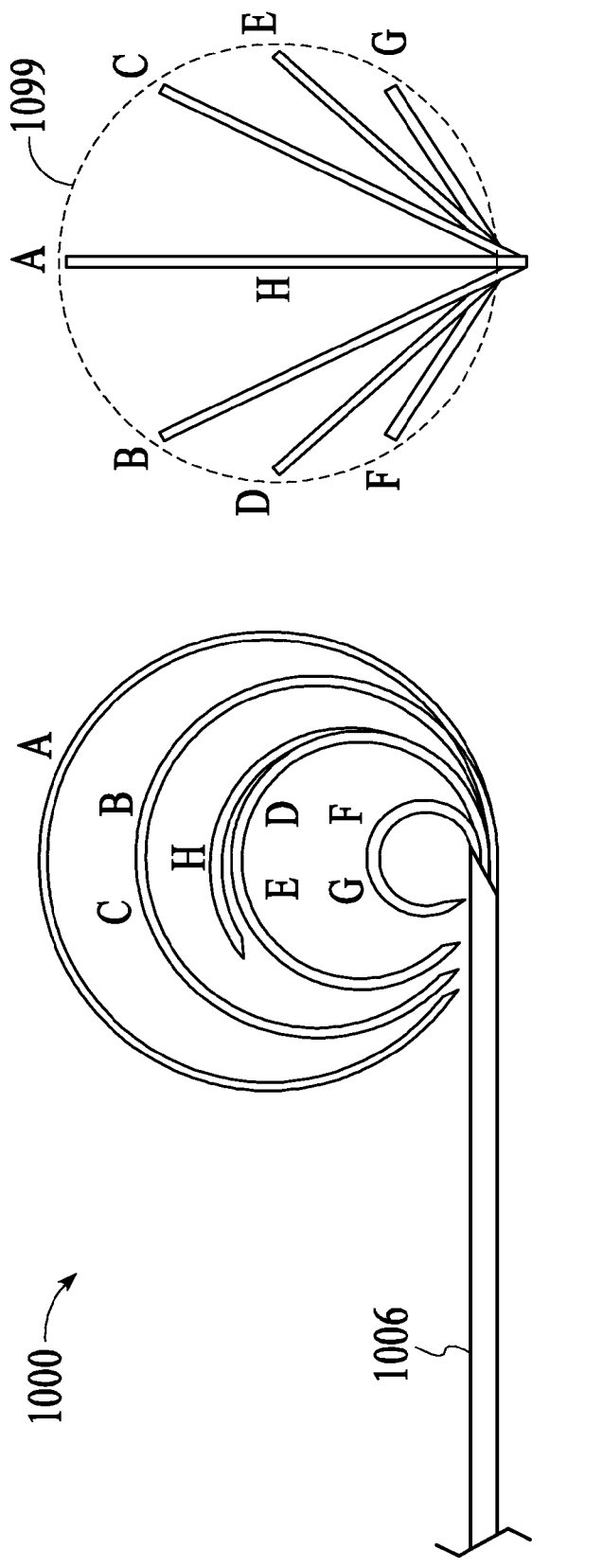
FIG. 10 is a distal portion of a tissue ablation device including a delivery member/tube and a plurality of energy conduits in a deployed state, under an alternative embodiment.

FIG. 10 is a distal portion 1000 of a tissue ablation device including a delivery member/tube and a plurality of energy conduits A, B, C, D, E, F, and G (collectively referred to as A-G) in a deployed state, under an alternative embodiment. The energy conduits A-G comprise nickel titanium alloy, for example, but can be formed from any number/combination of materials. Further, the outside diameter of the energy conduits A-G of an embodiment is approximately in the range of 0.010 to 0.040 inches, but is not so limited.

As described above, the delivery member/tube 1006 provides sufficient support for placement of the energy conduits A-G. Advancement of a deployment slider (not shown) advances and deploys the energy conduits A-G to a deployed shape. The shape of these energy conduits A-G can form a series of approximately semi-spherical segments which in this embodiment when taken together form the outline of a sphere 1099 that fully encompasses a volume of tissue targeted for ablation. The application of RF energy to the energy conduits A-G generates or produces a spherical volume of ablated tissue.

The energy conduits A-G of an embodiment are configured to each have an alternating electrical polarity. The energy conduits of an alternative embodiment are of a single electrical polarity, with the delivery member/tube 1006 conducting an opposite polarity. In still another alternative embodiment, the energy conduits A-G are individually switched between the same electrical polarity and the delivery member/tube 1006 conducts an opposite/alternating polarity to that of the energy conduits A-G. In yet another alternative embodiment, the delivery member/tube 1006 and energy conduits A-G are of a single electrical polarity and one or more secondary grounding pads are used therewith to provide an opposite polarity member.

In operation, the tissue ablation system of an embodiment delivers energy to target tissue via the energy conduits A-G. The energy includes, for example, radio frequency (RF) energy, but is not so limited. The energy is delivered via any of a number of techniques. The energy can be applied via pulsed waveforms and/or continuous waveforms, but is not so limited.

In an example procedure that includes use of the tissue ablation system, energy can be applied to energy conduits A-G during deployment of the energy conduits A-G into the target tissue. The energy can be applied automatically or, alternatively, manually as a procedure progresses and as appropriate to the procedure. Also, the energy delivered to the target tissue can be adjusted during the procedure by adjusting any of the power level, the waveforms, and a combination of the power level and the waveform.

In another example procedure that includes use of the tissue ablation system, energy can be applied to energy conduits A-G following deployment of the energy conduits A-G into the target tissue. The energy can be applied automatically or, alternatively, manually as appropriate to the procedure. Also, the energy delivered to the target tissue can be adjusted manually and/or automatically during the procedure by adjusting any of the power level, the waveforms, and a combination of the power level and the waveform.

In addition to the components of the tissue ablation device 1000, various sensing techniques can be used to guide or control the progress of the tissue ablation. For example temperature sensors can be embedded or attached to at least one of the energy conduits A-G and the delivery member/tube 1006 to provide feedback to a user and/or an energy controller. Additionally, a variety of sensors can be deployed from the tissue ablation device 1000 into tissue of the target tissue.

In addition to the components of the tissue ablation systems described above, various sensing techniques can be used with and/or coupled to the tissue ablation system to guide or control the progress of the tissue ablation. For example temperature sensors can be embedded or attached to the deployable energy conduits and provide feedback to a user or an energy controller. A variety of sensors can also be deployed from the device into tissue within the targeted tissue, in this case a sphere.

Figure 11:
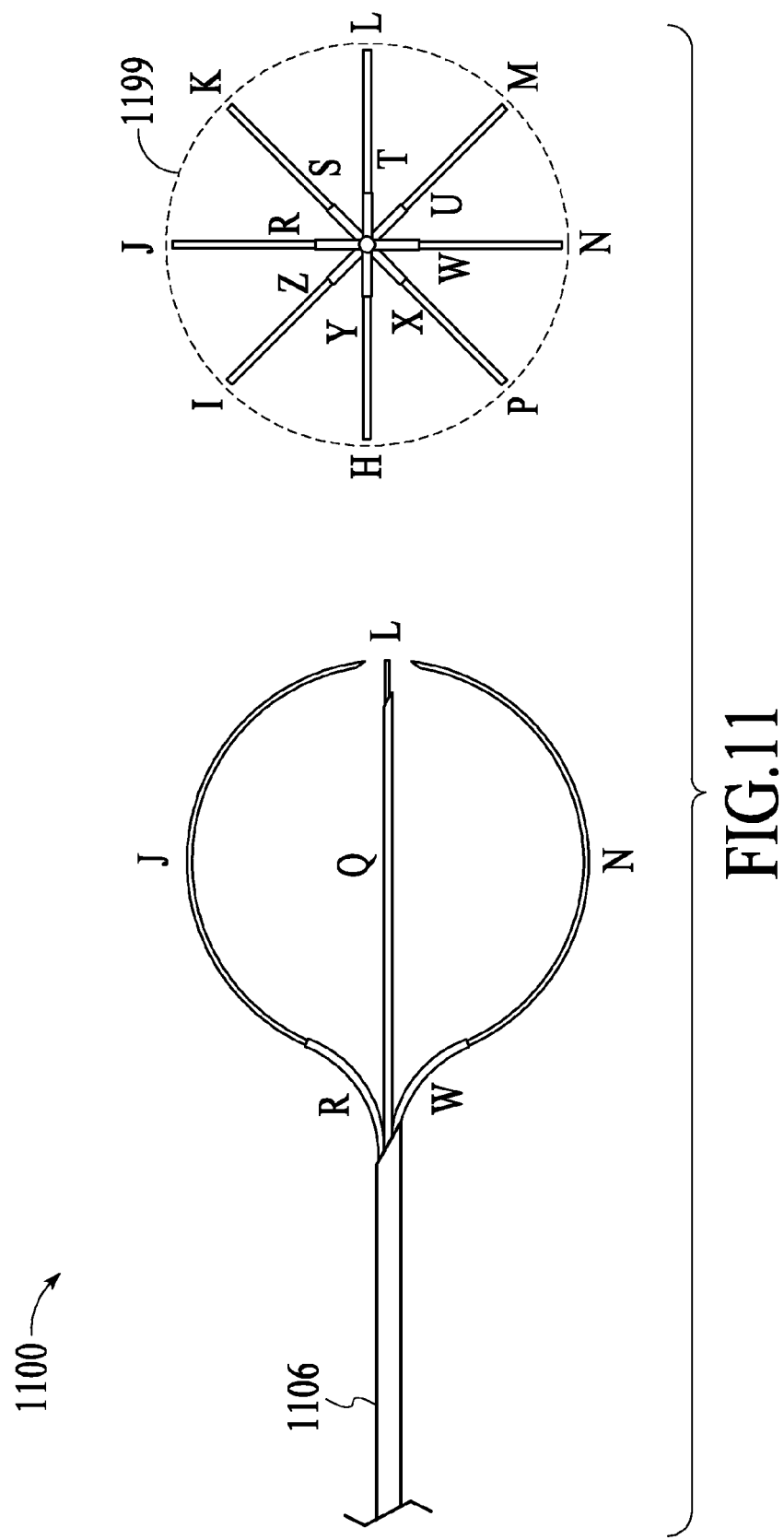
FIG. 11 is a distal portion of a tissue ablation device including a delivery member/tube and a plurality of energy conduits in a deployed state, under yet another alternative embodiment.

FIG. 11 is a distal portion 1100 of a tissue ablation device including a delivery member/tube 1106, a plurality of primary energy conduits R, S, T, U, W, X, Y, Z (collectively referred to as R-Z), and a plurality of secondary energy conduits H, I, J, K, L, M, N, and P (collectively referred to as H-P) and Q in a deployed state, under yet another alternative embodiment. For clarity electrodes H, I, K, M, P, S, T, U, X, Y, and Z have been omitted in the side view of the device shown in FIG. 11. The primary R-Z and secondary H-P energy conduits comprise nickel titanium alloy, for example, but can be formed from any number/combination of materials some of which are described above. Further, the outside diameter of the primary R-Z and secondary H-P energy conduits of an embodiment is approximately in the range of 0.010 to 0.080 inches, but is not so limited.

As described above, the delivery member/tube 1106 provides sufficient support for placement of the primary energy conduits R-Z. Likewise the primary energy conduits R-Z provide sufficient support for placement of the secondary energy conduits H-P. While the tissue ablation device of an embodiment deploys one secondary energy conduit from one or more distal and/or lateral ports in a distal region of each primary energy conduit, alternative embodiments of the tissue ablation device can deploy more than one secondary energy conduit from one or more distal and/or lateral ports of each primary energy conduit. Advancement of a deployment slider (not shown) as described above advances and deploys the energy conduits R-Z, H-P, and Q to a deployed state or shape in target tissue. The energy conduits R-Z, H-P in a deployed state form a series of approximately semi-spherical segments which when taken together in this embodiment form the outline of a sphere 1199 that fully encompasses a volume of tissue targeted for ablation. The application of RF energy to the energy conduits R-Z, H-P, and Q generates or produces a spherical volume of ablated tissue.

The energy conduits R-Z, H-P, and Q of an embodiment are configured to each have an alternating electrical polarity. The energy conduits of an alternative embodiment conduct electrical energy of a single electrical polarity, with the delivery member/tube 1106 conducting electrical energy having an opposite polarity. In still another alternative embodiment, the energy conduits H-P and R-Z are individually switched between the same electrical polarity and electrode Q is coupled to conduct electrical energy of an opposite/alternating polarity to that of the energy conduits H-P and R-Z. In yet another alternative embodiment, all energy conduits R-Z, H-P, and Q are of a single electrical polarity and one or more secondary grounding pads are used therewith to provide an opposite polarity member. In still another embodiment, electrode Q is not present and energy passes within the remaining electrodes.

In operation, the tissue ablation system of an embodiment delivers energy to target tissue via the energy conduits R-Z, H-P, and Q. The energy includes, for example, radio frequency (RF) energy, but is not so limited. The energy is delivered via any of a number of techniques, some of which are described herein. The energy can be applied via pulsed waveforms and/or continuous waveforms, but is not so limited.

In an example procedure that includes use of the tissue ablation system, energy can be applied to energy conduits R-Z, H-P, and Q during deployment of the energy conduits R-Z, H-P, and Q into the target tissue. The energy can be applied automatically or, alternatively, manually as a procedure progresses and as appropriate to the procedure. Also, the energy delivered to the target tissue can be adjusted during the procedure by adjusting any of the power level, the waveforms, and a combination of the power level and the waveform.

In another example procedure that includes use of the tissue ablation system, energy can be applied to energy conduits R-Z, H-P, and Q following deployment of the energy conduits R-Z, H-P, and Q into the target tissue. The energy can be applied automatically or, alternatively, manually as appropriate to the procedure. Also, the energy delivered to the target tissue can be adjusted manually and/or automatically during the procedure by adjusting any of the power level, the waveforms, and a combination of the power level and the waveform.

In addition to the components of the tissue ablation device 1100, various sensing techniques can be used to guide or control the progress of the tissue ablation. For example temperature sensors can be embedded or attached to at least one of the energy conduits R-Z, H-P, and Q and the delivery member/tube 1106 to provide feedback to a user and/or an energy controller. Additionally, a variety of sensors can be deployed from the tissue ablation device 1100 into tissue of the target tissue.

In addition to the components of the tissue ablation systems described above, various sensing techniques can be used with and/or coupled to the tissue ablation system to guide or control the progress of the tissue ablation. For example temperature sensors can be embedded or attached to the deployable energy conduits and provide feedback to a user or an energy controller. A variety of sensors can also be deployed from the device into tissue within the targeted tissue, in this case a sphere.

Figure 12:
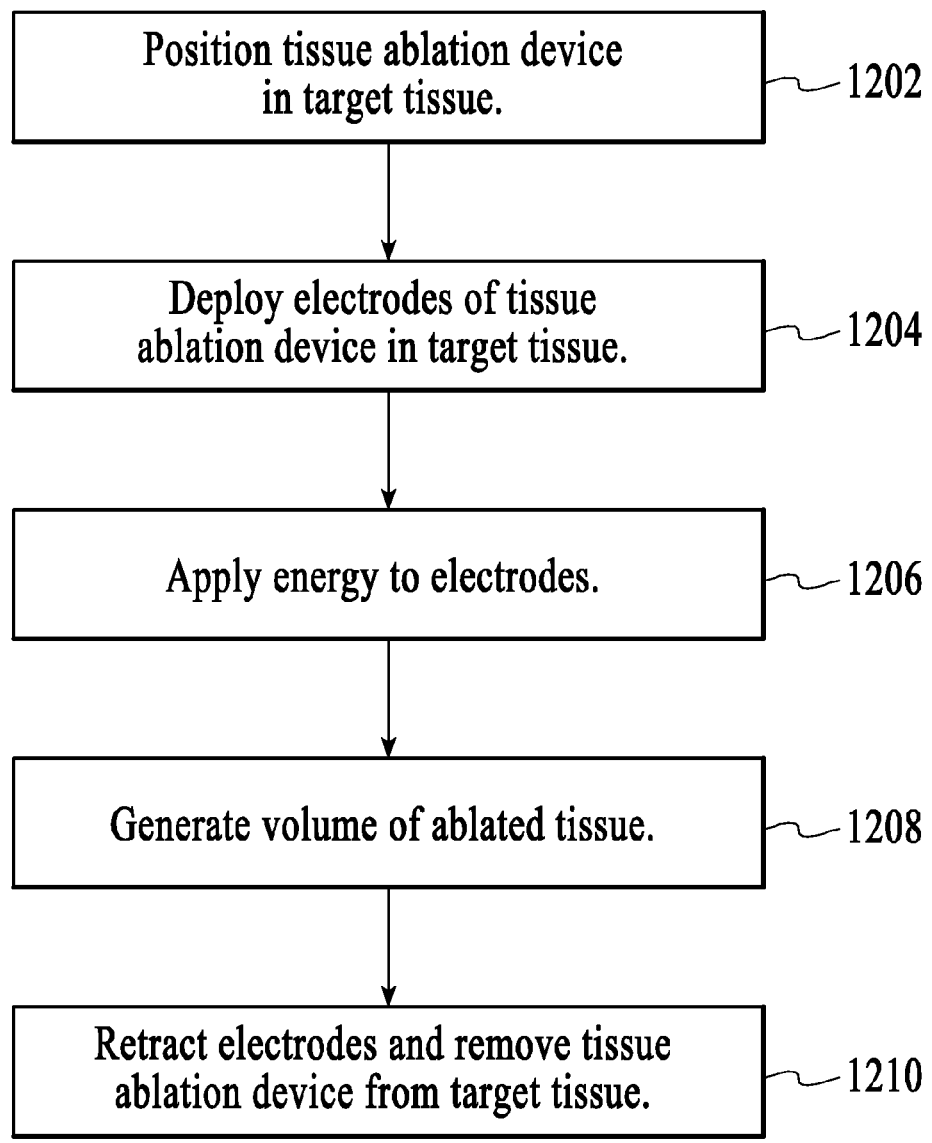
FIG. 12 is a flow diagram of tissue ablation procedure using the tissue ablation device, under an embodiment.

FIG. 12 is a flow diagram of tissue ablation procedure using the tissue ablation device, under an embodiment. In operation, generally a user positions the tissue ablation device in the target biological tissue as appropriate to a medical procedure, at block 1202. Placement of the tissue ablation device in the target tissue can include the use of various visualization methods such as ultrasound stenography, Computerized Tomography (CT), and Magnetic Resonance Imaging (MRI), but is not so limited.

Following placement of the device in the target tissue the user deploys the electrodes in the target tissue, at block 1204. Power or energy is applied to the target tissue via the electrodes, at block 1206. The energy generates a volume of ablated tissue having a shape and size appropriate to the configuration of the deployed electrodes, at block 1208. The user retracts the electrodes and removes the device from the target tissue, at block 1210.

In one or more additional embodiments, the electrodes of the ablation device can be configured to at least partially encircle the target tissue depending upon the location and distribution of the target tissue to be ablated. For these embodiment, one or more mono-polar or bipolar electrodes can be configured to totally surround or partially encircle the target tissue, e.g., a tumor, and application of energy through the electrodes is directed to create a spherical or relatively spherical area of ablation around and including the target tissue. Such a relatively spherical area could comprise an elongated spherical area (e.g., lozenge-shaped). The ablation area could also comprise an enclosed compound curved surface. One or more ablation devices, each containing an array of one or more electrodes is used to surround at least a portion of the target tissue or ablation volume and thereby ablate that portion upon deployment of the electrodes and application of energy from the energy source. Each such device thus creates an ablation pattern along one or more planes of the target tissue or ablation volume, and may be referred to as a "planar" device or electrode assembly.

Figures 13, 14:
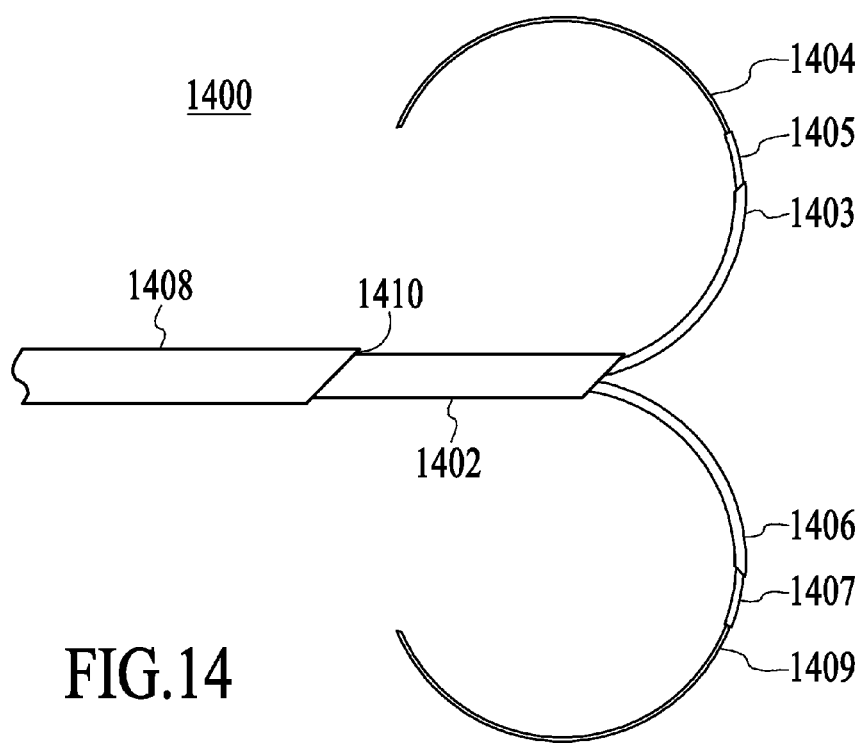
FIG. 13 is a table showing different example power supply settings for corresponding ablation sizes, under an embodiment.
FIG. 14 illustrates a compound electrode ablation device including a fluid path, according to an embodiment.

As illustrated in block 1206 of FIG. 12, energy is applied to the electrodes of the tissue ablation device in order to form a volume of ablated tissue. Such energy can be provided by an energy source 112, as shown in FIG. 1, or any similar energy source (RF generator or other type of generator) coupled directly or indirectly to the tissue ablation device. In general, the volume of ablated tissue depends upon one or more parameters related to the energy applied to the electrodes, such as power level, ablation time, energy density at the electrodes, and other similar factors. In one embodiment, the energy source includes one or more controls that allows the user to select certain operating parameters of the device. Typically these include at least output power levels (e.g., high-medium-low, or specific wattage settings), and a timer that controls the amount of time that energy is output from the generator. FIG. 13 is a table showing different example power supply settings for corresponding ablation sizes, under an embodiment. As shown in table 1300, the ablation size can vary from 3.5 cm to 7 cm based on the timer setting and power setting of the generator. In general, a longer time period of energy delivery and/or higher power setting results in a larger ablation size. FIG. 13 provides an example of typical ablation sizes for various generator settings for one type of RF generator. It should be noted that many other generator settings and resulting ablation sizes are possible, depending upon the type of generator used and other operating conditions. Moreover, other important parameters for use, such as duration of insertion, positional placement of the electrodes, movement of the electrodes during ablation, use of more than one device at a time and relative positioning of multiple devices, which are all controlled by the user at the time of ablation, will also have an important impact on the size and quality of the ablation area.

The tissue ablation systems described herein are unique in both their speed and ability to use a variety of existing radio frequency ablation generators available in many hospitals around the world as the energy source. For example, the devices described herein can be used with generators such as the Radio Therapeutics Corporation—Boston Scientific Generator (Models RF 2000® or RF 3000®), Celon LabPower (Celon-Olympus, Teltow-Berlin Germany), the Radionics® (Tyco Healthcare) Cool-tip™ RF Generator, and the RITA® System RF Generator (Model 1500 or 1500x) (Rita Medical Systems, Fremont, Calif.). Thus, various different types of energy sources 112 can be used in conjunction with the tissue ablation device, and may be radio frequency (RF) sources, or any similar and suitable energy source. Some of these may be commercially available devices made by one or more different manufacturers, and which have different generator output configurations. In this case an adapter may be needed to couple the tissue ablation device to the output jacks of the energy source.

Figure 17A:
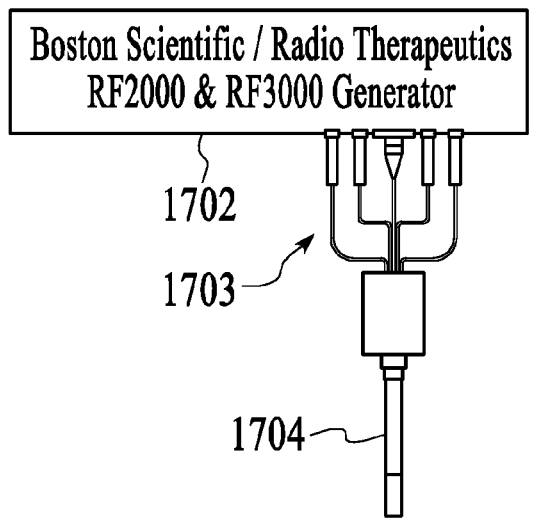
FIG. 17A illustrates an RF generator adapter for use with a tissue ablation device, under an embodiment.
Figure 17B:
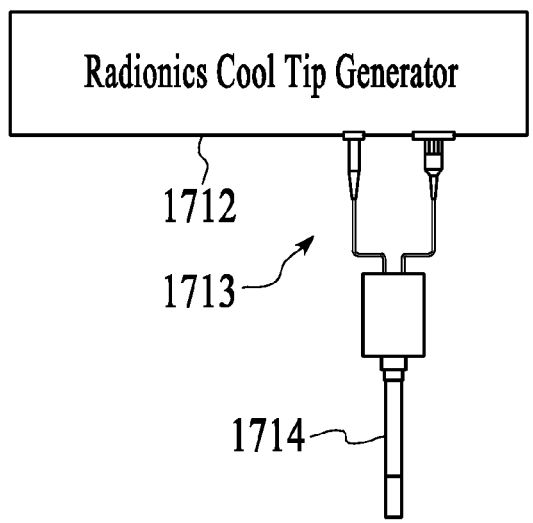
FIG. 17B illustrates an RF generator adapter for use with a tissue ablation device, under a first alternative embodiment.
Figure 17C:
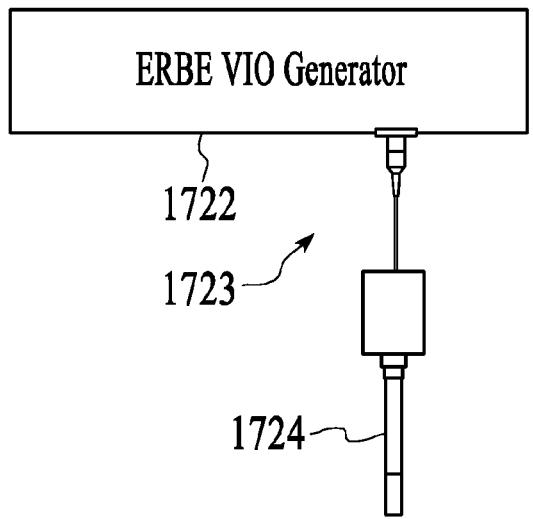
FIG. 17C illustrates an RF generator adapter for use with a tissue ablation device, under a second alternative embodiment.

FIG. 17A illustrates an RF generator adapter for use with a tissue ablation device under an embodiment. For the embodiment of FIG. 17, RF generator 1702 from Radio Therapeutics Corporation—Boston Scientific® Generator is coupled to ablation device 1704 through adapter 1703. FIG. 17B illustrates an RF generator adapter for use with a tissue ablation device under a first alternative embodiment. For this embodiment, RF generator 1712 is a Radionics® generator, which couples to ablation device 1714 through adapter 1713. FIG. 17C illustrates an RF generator adapter for use with a tissue ablation device under a second alternative embodiment. For this embodiment, RF generator 1722 is an Erbe® generator, which couples to ablation device 1724 through adapter 1723. As stated above, several other different types and makes of generator can also be used.

Figure 18A:
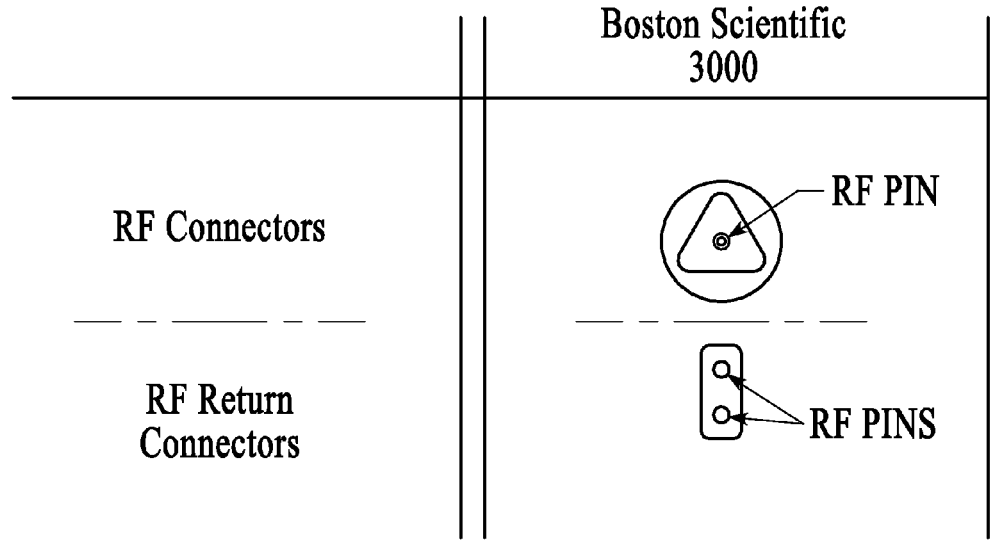
FIG. 18A illustrates an output panel for a first example RF generator for use with a tissue ablation device, under an embodiment.
Figure 18B:
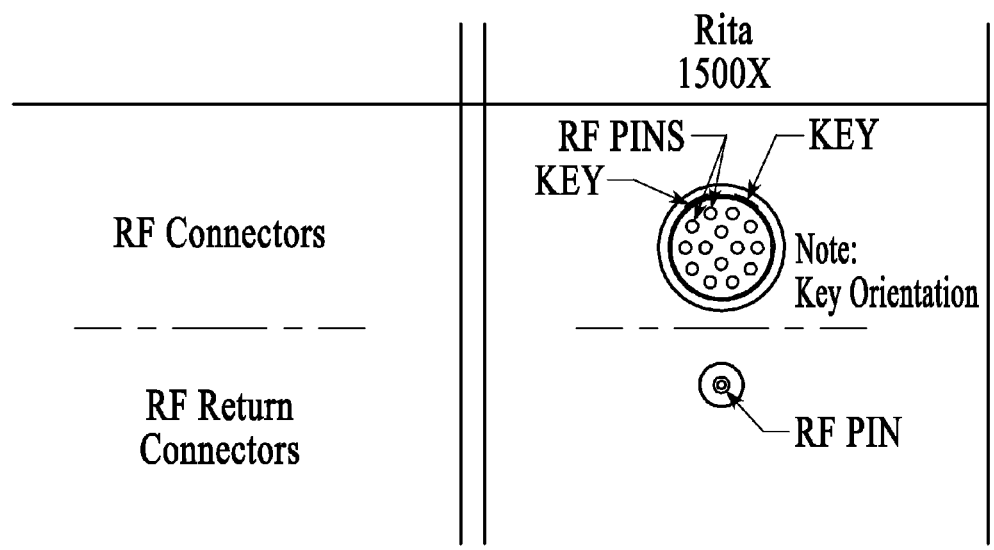
FIG. 18B illustrates an output panel for a second example RF generator for use with a tissue ablation device, under an embodiment.

The adapter that couples the ablation device to the generator should be configured to plug into the appropriate generator output jacks on the generator. Each generator that may be used may have different output jack configurations. FIG. 18A illustrates an output panel for a first example RF generator for use with a tissue ablation device, under an embodiment. This example output jack is for a Boston Scientific® model 300 generator, and shows the configuration of the RF output connector and the RF return connectors. FIG. 18B illustrates an output panel for a second example RF generator for use with a tissue ablation device under an embodiment. This example output jack if for a Rita® model 1500x generator, and shows the configuration of the RF output connector and the RF return connector for this model. As can be seen, the configuration of the RF jacks can vary significantly among different available devices.

The configuration and composition of an ablation device that is configured to encircle or at least partially encircle the target area can be implemented through various embodiments. FIG. 14 illustrates a compound electrode ablation device including a fluid path, according to an embodiment. For device 1400, two or more separate electrodes are deployed out of the distal end of trocar 1402. Each electrode comprises a compound electrode that has a positively charged portion and a negatively charged portion coupled together through an insulative member. Thus, FIG. 14 illustrates a device in which a first electrode includes a first portion 1403 and a second portion 1404 with an insulation member 1405, and a second electrode includes a first portion 1406 and a second portion 1409 with an insulation member 1407. The first portions 1403 and 1406 can be energized to a first polarity (e.g., negative), while the second portion of the electrodes can be energized to the opposite polarity (e.g., positive). The second portion of the electrode (e.g., 1404) can be installed and deployed through a lumen in the first portion of the electrode (e.g., 1403) around which an insulative sleeve (e.g., 1405) is inserted to maintain electrical isolation yet allow physical support of the second electrode portion within the first electrode portion.

Although two bipolar electrodes are illustrated in FIG. 14, it should be noted that a plurality of such compound electrodes can be deployed from trocar 1402, or they can be substituted by multiple single polarity electrodes. Furthermore, an additional electrode can be coupled to the body of the trocar itself. For the embodiment illustrated in FIG. 14, electrode 1408 is coupled to the body of trocar 1402 and electrically separated from electrodes 1404 and 1406 and 1402. A fluid path 1410 is formed between trocar 1402 and electrode 1408 to deliver fluid such as conductive saline. A dispersive electrode can be included in the device 1400 to create a mono-polar device, or a mono-polar/bi-polar device.

In one embodiment, an ablation device can formed by defining one of the electrodes as part of the trocar body and energizing this electrode with a polarity opposite that to one or more electrodes that are configured to protrude from an end or a portion of the trocar body. This creates an ablation pattern in a tissue field around the trocar when the protruding electrodes are deployed and energized relative to the electrode formed in the trocar body. Thus, with reference to the embodiment of FIG. 14, if electrode 1408 has a negative polarity and one or both of electrodes 1404 and 1406 and 1402 has a positive polarity, the deployment and energizing of the electrodes will cause ablation in a field surrounding the electrodes. The shape and size of the field can be defined by altering the number, length or size, and configuration of the electrodes, as well as the type and power of the energy source. For the embodiment illustrated in FIG. 14, in which the electrodes 1403/1404 and 1406/1409 are themselves compound electrodes, a separate electrode (e.g., electrode 1408) of a specific polarity may not necessarily need to be provided to form a bi-polar device. Furthermore, the coupling between the electrode 1408 may be through conductive fluid 1410, as shown, or it may be through an integrally-formed or adhesive-based coupling utilizing a second insulative member (not shown) to maintain electrical isolation between this electrode and the trocar body 1402.

To produce an electrode that is capable of having two or more polarities in a single element, the protruding electrodes shown in FIG. 14 can be made out of a flat base material, such as a spring/sheet metal. A conductive coating can be applied to the base material through an insulative layer so that a single electrode can be configured to have two different polarities when energized.

In certain embodiments, such as shown in FIG. 14, the electrodes may be relatively straight strips of metal deployed from the side or end of a trocar to surround a target tissue area. In some instances, more comprehensive encirclement of the target tissue can be accomplished through the use of curved or spiral-shaped electrodes.

Figure 15A:
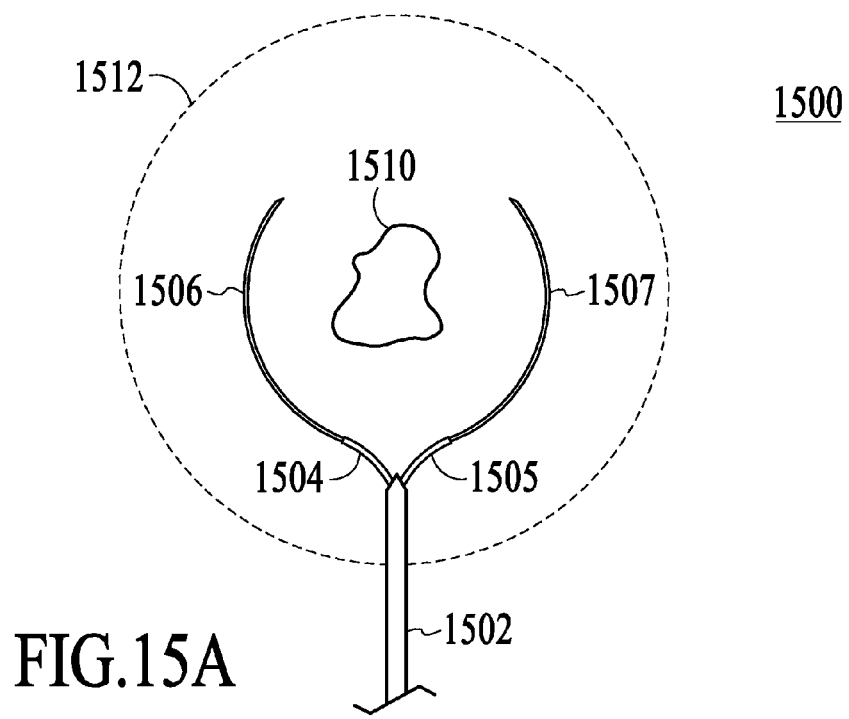
FIG. 15A illustrates a two stage ablation device for surrounding a target site, under an embodiment.

FIG. 15A illustrates a two-stage ablation device for surrounding a target site, under an embodiment. Device 1500 includes a set of electrode arrays that are deployed out of the end of trocar 1502 to at least partially encircle a target tissue 1510 upon deployment. The first set of electrodes 1504 and 1505 comprise stage 1 of the array, and the second set of electrodes 1506 and 1507 comprise stage 2 of the array. The stage 2 electrodes are mechanically coupled within the stage 1 electrodes and extend out of the stage 1 electrodes in a telescoping manner when deployed. The stage 1 electrodes 1504 and 1505 can be made out of round or elliptic tubing which can be formed to an appropriate shape and size to accommodate the inner, stage 2 electrodes. The stage 2 electrodes 1506 and 1507 can be made of round or flat wire to correspond with the inner dimensions and shape of the stage 1 electrodes.

Figure 15B:
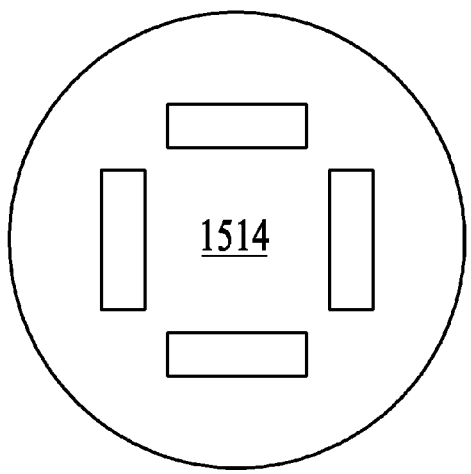
FIG. 15B illustrates an end view of the ablation device of FIG. 15A, under an embodiment.
Figure 15C:
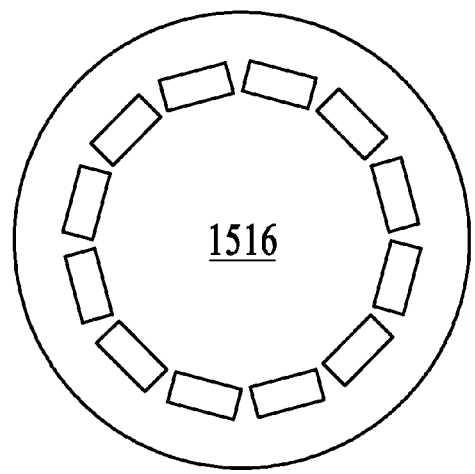
FIG. 15C illustrates an end view of the ablation device of FIG. 15A, under an alternative embodiment.

Any number of stage 1 and stage 2 electrodes can be configured to deploy out of the end of trocar 1502 to encircle the target tissue 1510 and produce an appropriate ablation pattern 1512. FIG. 15B illustrates an end view of the ablation device of FIG. 15A, under an embodiment in which four flat-wire electrodes 1514 in a square pattern deploy from the end of trocar 1502. FIG. 15C illustrates an end view of the ablation device of FIG. 15A, under an alternative embodiment in which twelve electrodes 1516 in a relatively circular pattern deploy from the end of trocar 1502. As can be seen from FIGS. 15B and 15C, as more electrodes are deployed, a more circular a pattern is produced around the end of the trocar, thus resulting in a more nearly spherical ablation pattern 1512 around the target tissue 1510.

FIG. 15A illustrates an embodiment in which the electrodes are configured to at least partially surround the target tissue. In an alternative embodiment, one or more electrodes may be configured to penetrate the target tissue, while other electrodes surround the tissue to produce the ablation pattern 1512. FIG. 16A illustrates an ablation device containing both surrounding electrodes and a penetrating electrode, according to an embodiment. In device 1600, electrodes 1604 and 1606 are configured to surround the target tissue 1610 upon deployment from trocar 1602 to form an ablation pattern 1612. A penetrating electrode 1608 deploys out of the distal end of trocar 1602 and includes a penetrating member for piercing target tissue 1610. The electrodes 1604, 1606 and 1608 can be configured as mono-polar or bi-polar electrodes to create a mono-polar or bi-polar device. One or more electrodes can also include a fluid delivery element for delivering fluid directly into target tissue. This is illustrated in FIG. 16B, in which trocar 1603 includes a fluid delivery element 1618. Element 1618 may be a delivery tube that is electrically neutral with respect to the other electrodes 1616 and 1619, it may be an electrode with a lumen, that is energized to a certain polarity relative to the other electrodes 1616 and 1619 and/or the body of the trocar 1603.

Deployment of the electrodes for the embodiments illustrated in any of FIGS. 13-15C can be performed by an activation device in a handle coupled to an end of the trocar, such hand piece 102 illustrated in FIG. 1. The electrode or electrodes in the device are coupled to a guide wire or other transport mechanism. The electrodes are deployed by advancing the guide wire outward and retracted by pulling the guide wire back into the trocar. A gear mechanism couples the activation unit such as a slider or knob (e.g., activator 104 in FIG. 1) to the guide wire, or similar push/pull rods that extend or retract the electrodes.

The devices shown in the embodiments of FIGS. 13-15C generally illustrate a single trocar device. In one embodiment, an ablation device containing multiple electrodes configured to surround a target tissue or ablate a tissue volume can comprise more than one trocar, with each trocar containing one or more electrodes that surround the target tissue or a portion of the target tissue. The two or more trocars can be coupled to a single handle and activation device, or they can each be connected to their own handle and activation device. In general, a user manipulates both or all of the trocar bodies comprising a multi-trocar device to place the electrodes around the target tissue or within the tissue volume to create the intended ablation pattern. The electrode arrays for each trocar can extend from the end of the device or from the side of the device, or a combination of both. Furthermore, the electrodes in each array may be a single unit of a single polarity or a compound unit with one portion of a first polarity and a second portion of the opposite polarity.

Figure 19A:
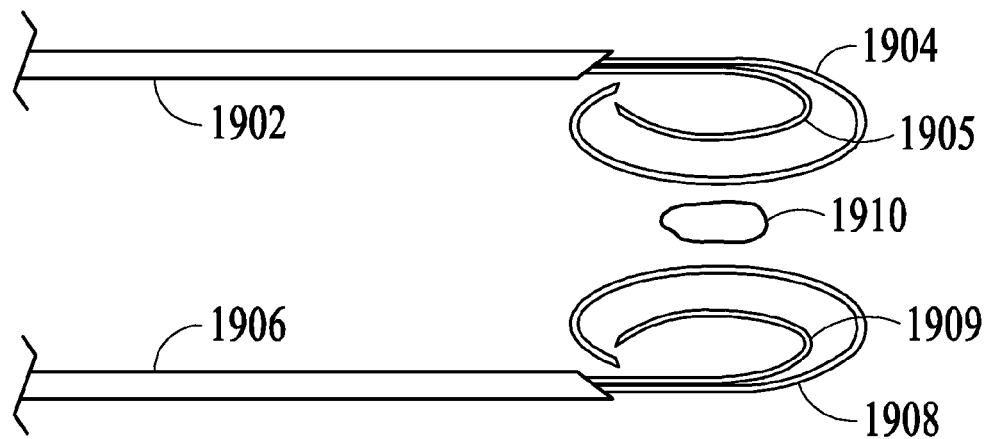
FIG. 19A is a side-view illustration of a compound ablation device with two separate trocars for encircling a target tissue, under an alternative embodiment.
Figure 19B:
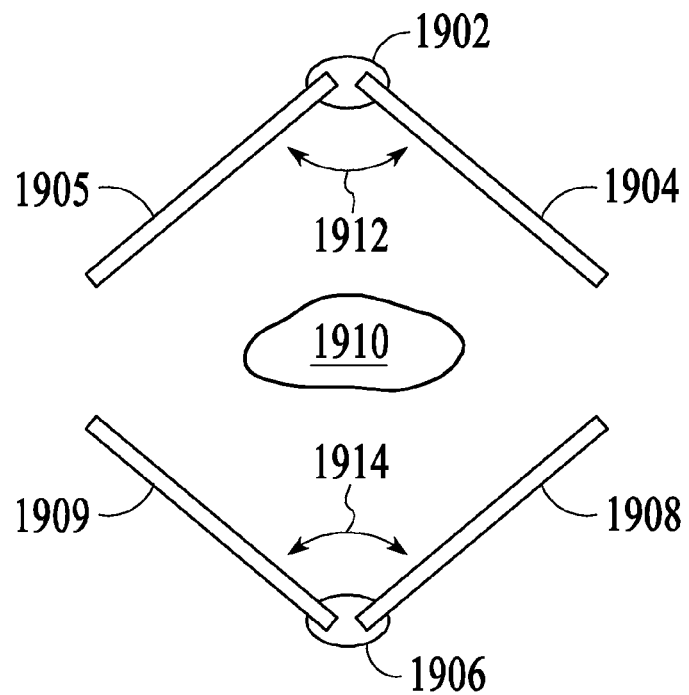
FIG. 19B is an end view of the alternative embodiment of FIG. 23A.

FIG. 19A illustrates a multi-trocar ablation device that utilizes one or more spiral electrodes in an array protruding from the distal end of each trocar. The device shown comprises a first trocar 1902 with two or more spiral electrodes 1904 and 1905 that extend from the end of the trocar at specific angles relative to the longitudinal axis of the trocar. A second trocar 1906 has two or more spiral electrodes 1908 and 1909 that likewise extend from the end of the trocar at specific angles relative to the longitudinal axis of the trocar. The angles of extension, as well as the electrode arrays are themselves shaped and configured so as to encircle target tissue 1910 and create a spherical or near-spherical ablation pattern in a tissue volume around the target tissue 1910. FIG. 19B is an end view of the multi-trocar ablation device of FIG. 19A. As shown in FIG. 19B, the electrodes 1904 and 1905 extend from the body of trocar 1902 at an angle 1912 relative to one another as defined by the longitudinal axis of the trocar, and the electrodes 1908 and 1909 extend from the body of trocar 1906 at an angle 1914 relative to one another as defined by the longitudinal axis of the trocar. The angle at which the electrode pairs are deployed relative to one another, as well as the electrode length, and tightness of spiral can be changed depending upon the actual application and characteristics of the target tissue 1910. The electrodes may each be of a single polarity with alternating polarity electrodes utilized in each pair or array of electrodes for each trocar, or they may be compound electrodes with sections of different polarities within each electrode. Thus, for example, for the embodiment illustrated in FIG. 19B, electrodes 1905 and 1909 can be both positively charged, with electrodes 1904 and 1908 both negatively charges, or electrodes 1905 and 1908 can be both positively charged, with electrodes 1904 and 1909 both negatively charged.

Although the embodiments of FIGS. 19A and 19B illustrate ablation systems comprising two separate trocar devices, it should be noted that greater than two trocars (e.g., three or four) may be used depending upon the application and characteristics of the target tissue. Furthermore, each of the trocars in a multi-trocar ablation device may use electrode arrays of different configurations to access and encircle difficult to reach target tissue areas or encircle target tissues of different sizes and configurations.

Planar Tissue Ablation

In one or more additional embodiments, the electrodes of the ablation device can be configured to at least partially encircle the target tissue depending upon the location and distribution of the target tissue to be ablated, as described in detail above. For these embodiments, one or more monopolar or bipolar electrodes can be configured to totally surround or partially encircle the target tissue, e.g., a tumor, and application of energy through the electrodes is directed to create a spherical or relatively spherical area of ablation around and including the target tissue. Such a relatively spherical area could comprise an elongated spherical area (e.g., lozenge-shaped). The ablation area could also comprise an enclosed compound curved surface. One or more ablation devices, each containing an array of one or more electrodes is used to surround at least a portion of the target tissue or ablation volume and thereby ablate that portion upon deployment of the electrodes and application of energy from the energy source. Each such device thus creates an ablation pattern along one or more planes of the target tissue or ablation volume, and may be referred to as a "planar" device or electrode assembly. The embodiments that follow are provided as additional example embodiments and do not limit the ablation device described herein to only these embodiments.

In all of the embodiments described below, the polarity of any electrode can be positive or negative. Also, the polarity of any set of electrodes can be positive or negative (e.g., a trocar can include a first set of electrodes, all of which are positive, and a second set of electrodes, all of which are negative; a trocar can include a first set of electrodes, all of which are positive, and a second set of electrodes, all of which are positive, etc.). Further, in multi-trocar embodiments, the polarity of any electrode or any set of electrodes of a single trocar can be positive or negative (e.g., a first trocar can include a first set of electrodes, all of which are positive, and a second trocar can include a first set of electrodes, all of which are negative; a first trocar can include a first set of electrodes, all of which are positive, and a second trocar can include a first set of electrodes, all of which are positive; a first trocar can include a first set of electrodes, all of which are positive, and a second set of electrodes, all of which are negative, and a second trocar can include a first set of electrodes, all of which are positive, and a second set of electrodes, all of which are negative, etc.).

Figure 20A:
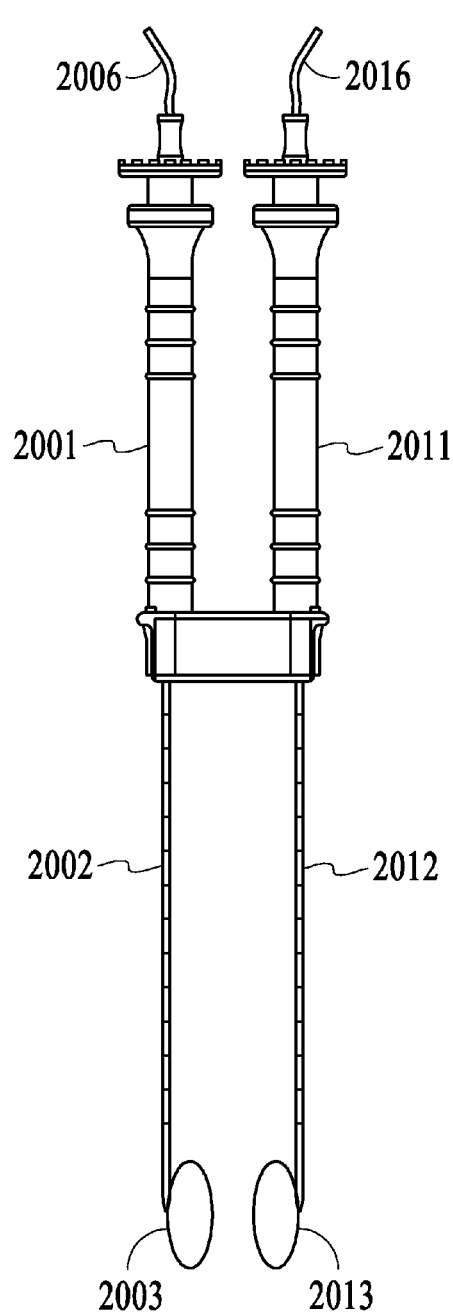
FIG. 20A is a front view of a dual-trocar ablation device that uses one or more spiral electrodes in an array protruding from the distal end of each trocar, under an embodiment.

In one embodiment, a planar tissue ablation device utilizes two or more trocars (multi-trocar) each deploying one or more electrodes to partially or entirely surround the target tissue. FIG. 20A is a front view of a dual-trocar ablation device that uses one or more spiral electrodes in an array protruding from the distal end of each trocar, under an embodiment. As shown in FIG. 20A, the dual-trocar device comprises a first handle assembly (or main shaft) 2001 from which trocar 2002 protrudes, and a second handle assembly (or main shaft) 2011 from which trocar 2012 protrudes. A dual spiral electrode array 2003 extends from the distal end of trocar 2002, and a dual spiral electrode array 2013 extends from the distal end of trocar 2012. For the embodiment of FIG. 20A, each electrode array 2003 and 2013 comprises two separate spiral electrodes that form an approximately circular shape of a certain diameter when deployed out of their respective trocar. In one embodiment, the electrodes are deployed and retracted through a plunger-style deployment device which is activated by pushing or pushing plunger handle 2007 or 2017 in the appropriate handle assembly. One or more wires 2006 and 2016 are coupled to the proximal end of respective handle assemblies 2001 and 2002 for connection to an external energy source, such as RF generator 1702 in FIG. 17. A mechanical coupling device or bridge 2010 is affixed to both handle assemblies 2001 and 2002 to fix their position relative to one another during use. The bridge 2010 may be attached as a sleeve unit that is friction fit over the ends of both handle assemblies, or it may be a clip on unit that clips on to both assemblies anywhere along the shaft length of the handles.

In general, the electrodes of each electrode array, when in a retracted state, are positioned in the trocar lumen. The electrodes themselves generally comprise conductive wire elements. The electrode can be round, or they can an electrode surface area that is maximized through the use of large flat wire. Each electrode has at least one radius of curvature in the deployed state so that the electrode array forms a series of shaped electrodes in the deployed state. The shape of a deployed electrode refers to the two-dimensional outline or path that the electrode wire traces as it moves out of the trocar during deployment. In a fully or partially deployed state, the electrode is in a static position, which has a certain shape. In the deployed state then, the electrode configuration or geometry makes use of a generally circular shape, which has the effect of "long" electrodes having a large surface area and therefore large tissue engagement area. In one embodiment, the deployment shape of the electrodes in each array is elliptical. An ellipse is generally defined as a locus of points in a plane such that the sum of the distances to two fixed points is constant. This typically represents a shape that is ovaloid, such as obtained when intersecting a cone with a plane. Alternatively, the deployment shape of the electrodes in each array is circular. A circle is generally defined as the locus of all points in a plane at a constant radius from a fixed point, and is a specific type of ellipse. The combination of electrode surface area, individual electrode spacing, and overall device configuration or geometry result in relatively complete ablations compared to present conventional RF ablation systems.

Figure 20B:
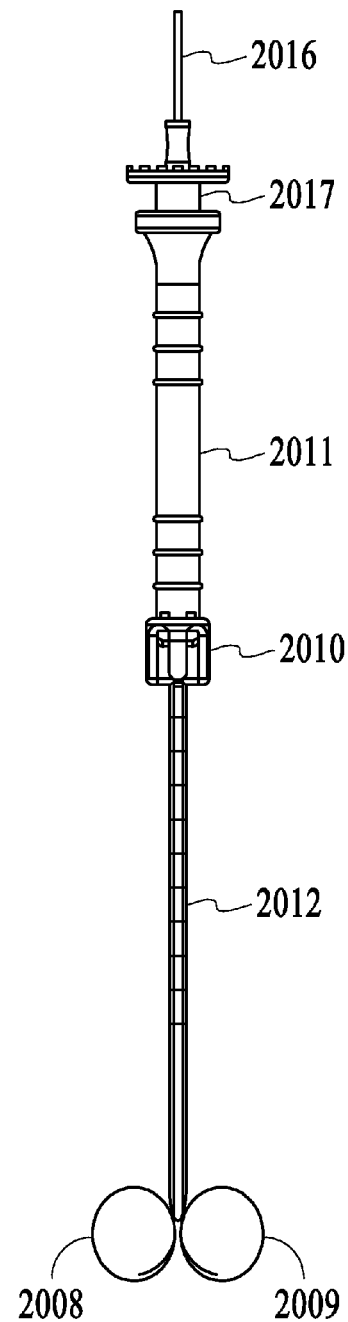
FIG. 20B is a side view of a dual-trocar ablation device, under the embodiment of FIG. 20A.

FIG. 20B is a side view of a dual-trocar ablation device of FIG. 20A. This view shows the independent electrodes 2008 and 2009, which make up electrode set 2013 which is deployed from trocar 2012. The individual electrodes within each electrode set are deployed at a defined angle relative to one another. This angle may be varied to change the coverage of the electrodes and the size and shape of the ablated area. FIG. 20C is a perspective view of a dual-trocar ablation device of FIG. 20A. This view shows the angle of deployment of the electrodes within each electrode set relative to one another, as well as the approximate volume defined by the deployed electrodes.

Figure 20D:
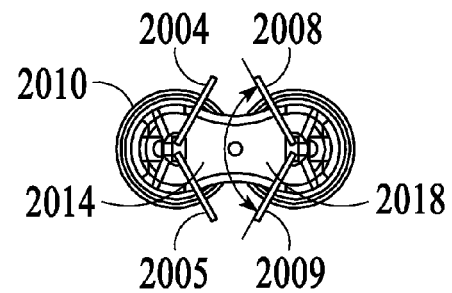
FIG. 20D is an end view of a dual-trocar ablation device, under the embodiment of FIG. 20A.
Figure 20C:
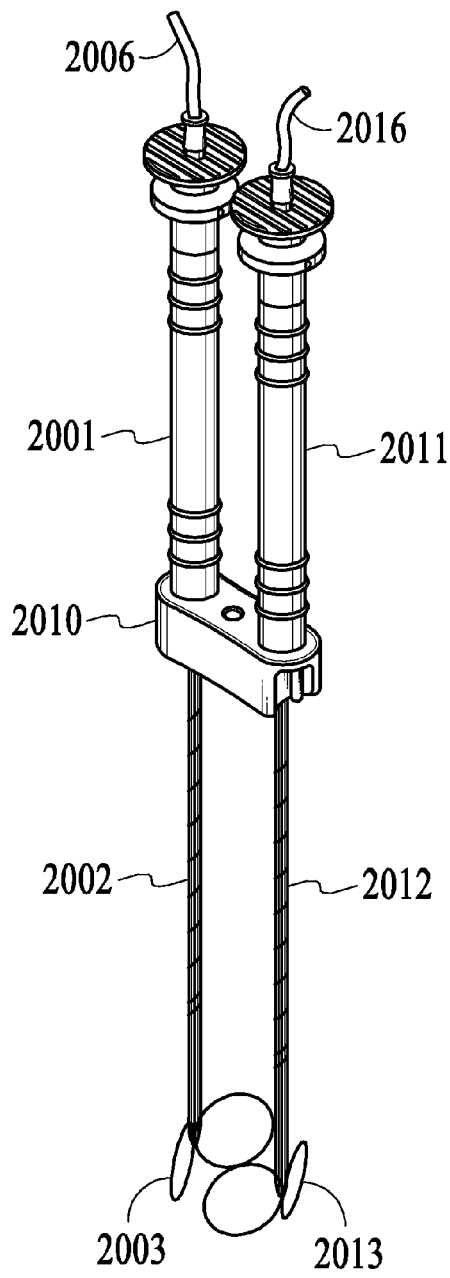
FIG. 20C is a perspective view of a dual-trocar ablation device, under the embodiment of FIG. 20A.

FIG. 20D is an end view of a dual-trocar ablation device of FIG. 20A, and shows the electrodes 2004 and 2005 comprising electrode set 2003 extending from the body of trocar 2002 at an angle 2014 relative to one another as defined by the longitudinal axis of the trocar 2002, and the electrodes 2008 and 2009 comprising electrode set 2013 extend from the body of trocar 2012 at an angle 2018 relative to one another as defined by the longitudinal axis of the trocar 2012. The angle at which the electrode pairs are deployed relative to one another, as well as the electrode length, and tightness of spiral can be changed depending upon the actual application and characteristics of the target tissue.

The example device illustrated in FIGS. 20A-D is generally configured to create an ablation area on the order of 3.5 cm in diameter. This area results from a number of factors, such as the angle between electrodes within each electrode, and the distance between the electrode sets. For the embodiment shown in FIG. 20D, the angle between electrodes in each set as illustrated is 110° and the electrode spacing is on the order of 0.33", although it should be understood that many other angles and electrode spacings are possible. In one embodiment, the electrode spacing is defined by the width of bridge 2010. It can also be altered by bending the electrode sets toward or away from one another. For embodiments in which a bridge is not used, the electrode spacing can be controlled by the user who can manipulate each trocar 2002 and 2012 independently of one another.

Figure 20E:
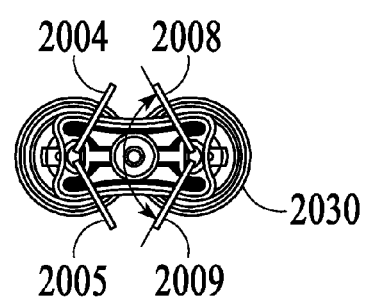
FIG. 20E is an end view of a dual-trocar ablation device of FIG. 20A, with a molded bridge assembly, under an embodiment.

In one embodiment, the bridge that couples the trocars of the bi-trocar device in a fixed position relative to one another is a removable device so that the electrodes can be deployed independently if desired. In an alternative embodiment, the bridge may be molded so that the trocars are effectively permanently coupled to one another. This prevents any slipping of the trocars relative to one another during use, especially during deployment of one or both of the electrode sets. FIG. 20E is an end view of a dual-trocar ablation device of FIG. 20A, with a molded bridge assembly, under an embodiment. As shown in FIG. 20E, bridge 2030 includes a molded inner portion that is integrally molded to the handle assemblies 2001 and 2011 to fix the trocars firmly in positions relative to one another.

Figures 21A, 21B:
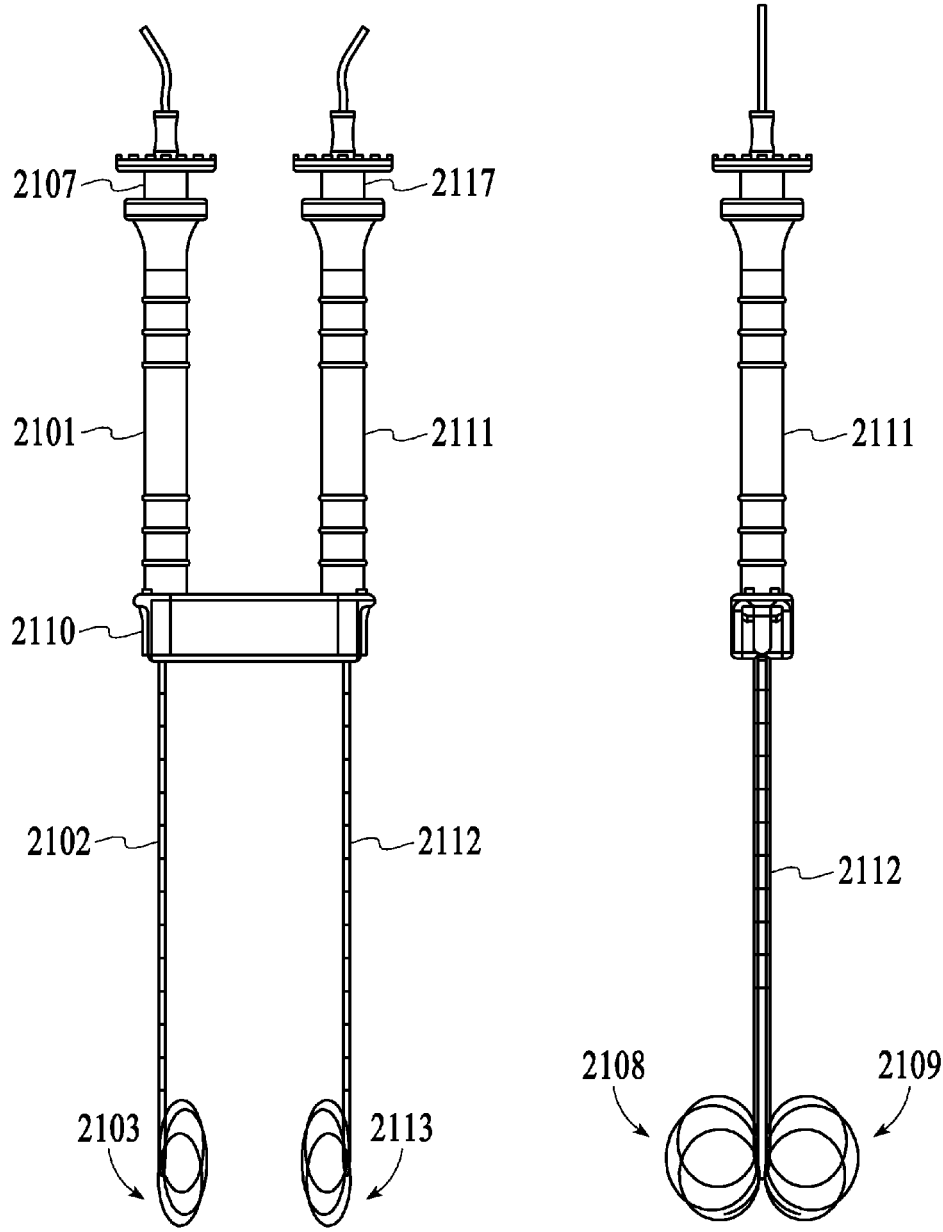
FIG. 21A is a front view of a dual-trocar ablation device that uses one or more spiral electrodes in an array protruding from the distal end of each trocar, under an alternative embodiment.
FIG. 21B is a side view of a dual-trocar ablation device, under the embodiment of FIG. 21A.

As described above with respect to FIGS. 20A-E, the ablation area is defined by a number of factors related to the configuration of the electrodes and their angles and distances relative to one another. FIG. 21A is a front view of a dual-trocar ablation device that uses one or more spiral electrodes in an array protruding from the distal end of each trocar, under an alternative embodiment. The basic components and arrangement of components for the device of FIG. 21A is similar to the device of FIG. 20A, except for one or more specific elements. As shown in FIG. 21A, the bridge 2110 separating handle assemblies 2101 and 2111 produces a different electrode distance between the electrode arrays 2103 and 2113. The electrode array 2103 that extends from the distal end of trocar 2102 comprises a plurality of electrode wires, each protruding from a separate orifice or lumen in trocar 2102. Likewise, the electrode array 2113 that extends from the distal end of trocar 2112 comprises a plurality of electrode wires, each protruding from a separate orifice or lumen in trocar 2112. For the embodiment of FIG. 21A, electrode array 2103 consists of two sets of three electrodes that each form a circular shape of a certain diameter when deployed out of trocar 2012, and electrode array 2113 consists of two sets of three electrodes that each form a circular shape of a certain diameter when deployed out trocar 2112. In one embodiment, the electrodes of each set are deployed and retracted together through a plunger-style deployment device which is activated by pushing or pushing plunger handle 2107 or 2117 in the appropriate handle assembly.

Figure 21C:
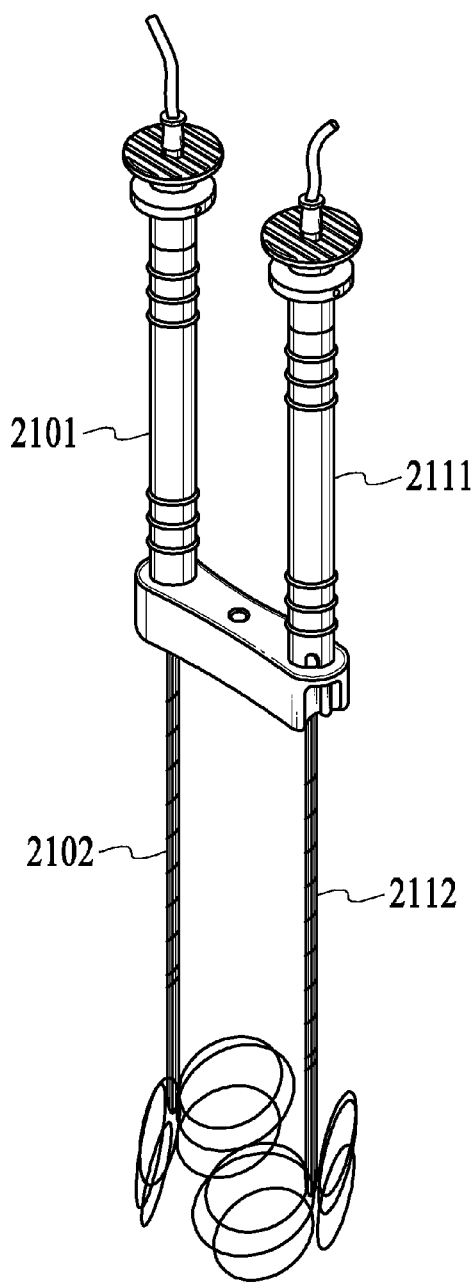
FIG. 21C is a perspective view of a dual-trocar ablation device, under the embodiment of FIG. 21A.

FIG. 21B is a side view of a dual-trocar ablation device of FIG. 21A. This view shows the two sets 2108 and 2109 of three individual electrodes, which make up electrode set 2113 when it is deployed from trocar 2112. FIG. 21C is a perspective view of a dual-trocar ablation device of FIG. 21A. This view shows the angle of deployment of the electrodes within each electrode set relative to one another, as well as the approximate volume defined by the deployed electrodes.

Figure 21D:
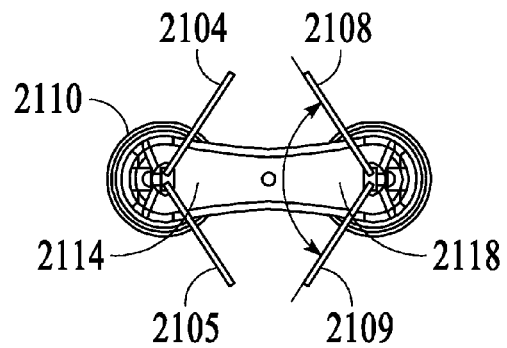
FIG. 21D is an end view of a dual-trocar ablation device, under the embodiment of FIG. 21A.
Figure 21E:
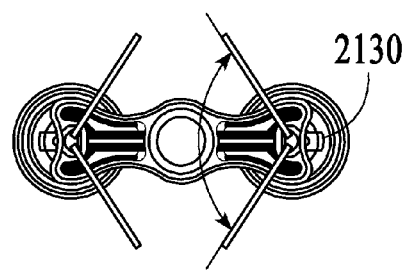
FIG. 21E is an end view of a dual-trocar ablation device of FIG. 21A, with a molded bridge assembly, under an embodiment.

FIG. 21D is an end view of a dual-trocar ablation device of FIG. 21A, and shows the electrodes 2104 and 2105 comprising electrode set 2103 extend from the body of trocar 2102 at an angle 2114 relative to one another as defined by the longitudinal axis of the trocar 2102, and the electrodes 2108 and 2109 comprising electrode set 2113 extend from the body of trocar 2112 at an angle 2118 relative to one another as defined by the longitudinal axis of the trocar 2112. The example device illustrated in FIGS. 21A-D is generally configured to create an ablation area on the order of 5.0 cm in diameter. This area results from a number of factors, such as the angle between electrodes within each electrode, and the distance between the electrode sets. For the embodiment shown in FIG. 21D, the angle between electrodes in each set as illustrated is 110° and the electrode spacing is on the order of 0.60", although it should be understood that many other angles and electrode spacings are possible. In one embodiment, the electrode spacing is defined by the width of bridge 2110. FIG. 21E is an end view of a dual-trocar ablation device of FIG. 21A, with a molded bridge assembly, under an embodiment. As shown in FIG. 21E, bridge 2130 includes a molded inner portion that is integrally molded to the handle assemblies 2101 and 2111 to fix the trocars firmly in positions relative to one another.

Figures 22A, 22B:
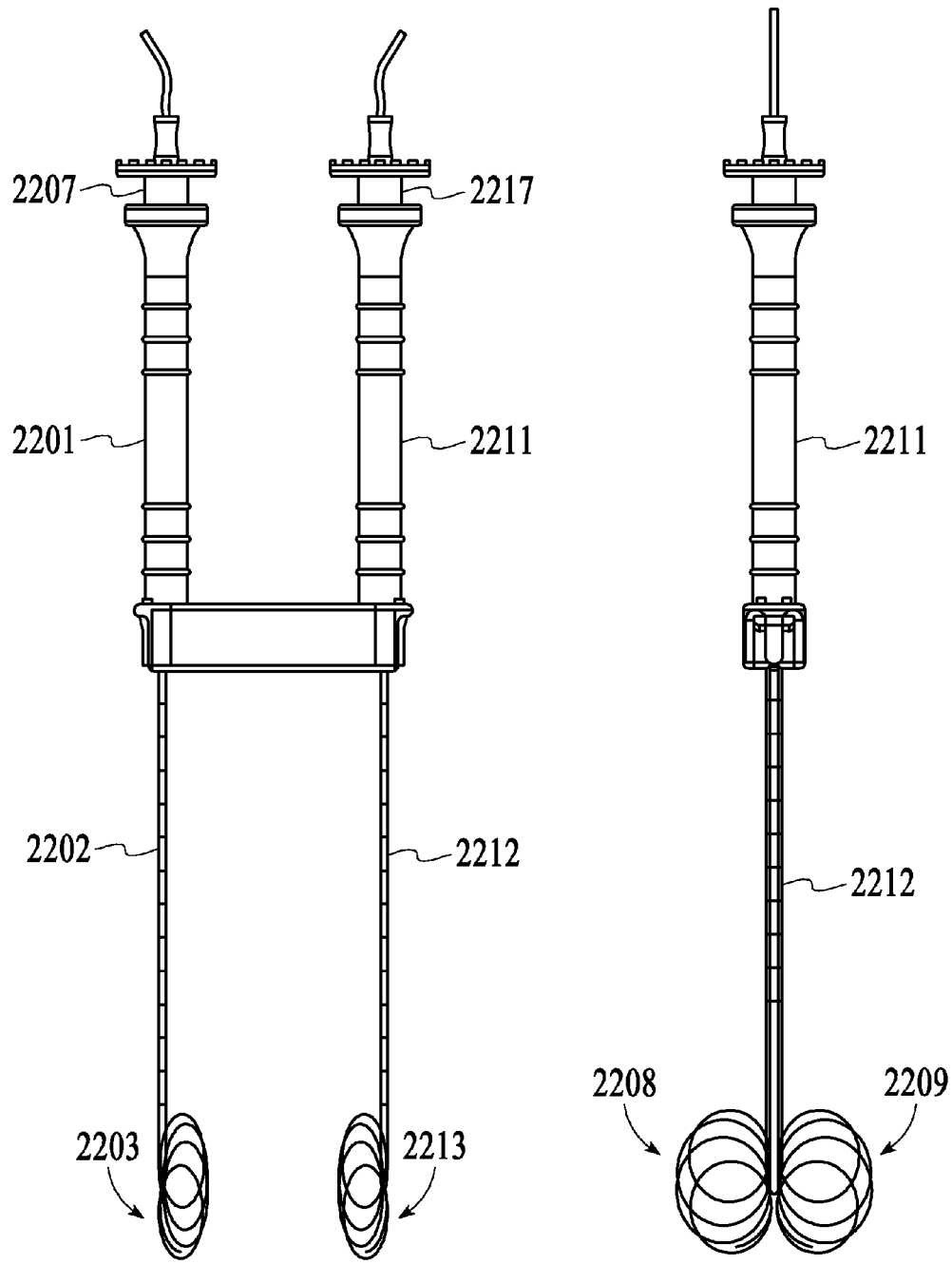
FIG. 22A is a front view of a dual-trocar ablation device that uses one or more spiral electrodes in an array protruding from the distal end of each trocar, under a further alternative embodiment.
FIG. 22B is a side view of a dual-trocar ablation device, under the embodiment of FIG. 22A.

Larger ablation diameters than produced by the devices of FIGS. 20 and 21 can be produced by altering the electrode configuration and spacing of the dual trocar device. FIG. 22A is a front view of a dual-trocar ablation device that uses one or more spiral electrodes in an array protruding from the distal end of each trocar, under a further alternative embodiment. The basic components and arrangement of components for the device of FIG. 22A is similar to the device of FIG. 20A, except for one or more specific elements. As shown in FIG. 22A, the bridge 2210 separating handle assemblies 2201 and 2211 produces a different electrode distance between the electrode arrays 2203 and 2213. The electrode array 2203 that extends from the distal end of trocar 2202 comprises a plurality of electrode wires, each protruding from a separate lumen in trocar 2202. Likewise, the electrode array 2213 that extends from the distal end of trocar 2212 comprises a plurality of electrode wires, each protruding from a separate lumen in trocar 2212. For the embodiment of FIG. 22A, electrode array 2203 consists of two sets of four electrodes that each form a circular shape of a certain diameter when deployed out of trocar 2212, and electrode array 2213 consists of two sets of four electrodes that each form a circular shape of a certain diameter when deployed out trocar 2212. In one embodiment, the electrodes of each set are deployed and retracted together through a plunger-style deployment device which is activated by pushing or pushing plunger handle 2207 or 2217 in the appropriate handle assembly.

FIG. 22B is a side view of a dual-trocar ablation device of FIG. 22A. This view shows the two sets 2208 and 2209 of four individual electrodes, which make up electrode set 2213 when it is deployed from trocar 2212. FIG. 22C is a perspective view of a dual-trocar ablation device of FIG. 22A. This view shows the angle of deployment of the electrodes within each electrode set relative to one another, as well as the approximate volume defined by the deployed electrodes.

Figure 22D:
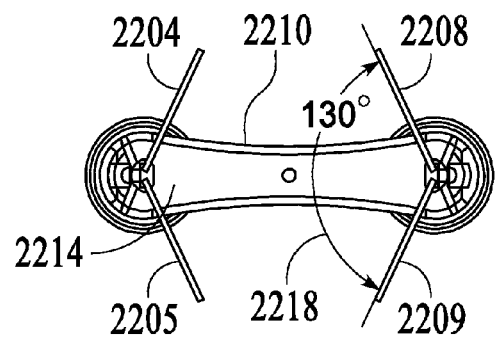
FIG. 22D is an end view of a dual-trocar ablation device, under the embodiment of FIG. 22A.
Figure 22C:
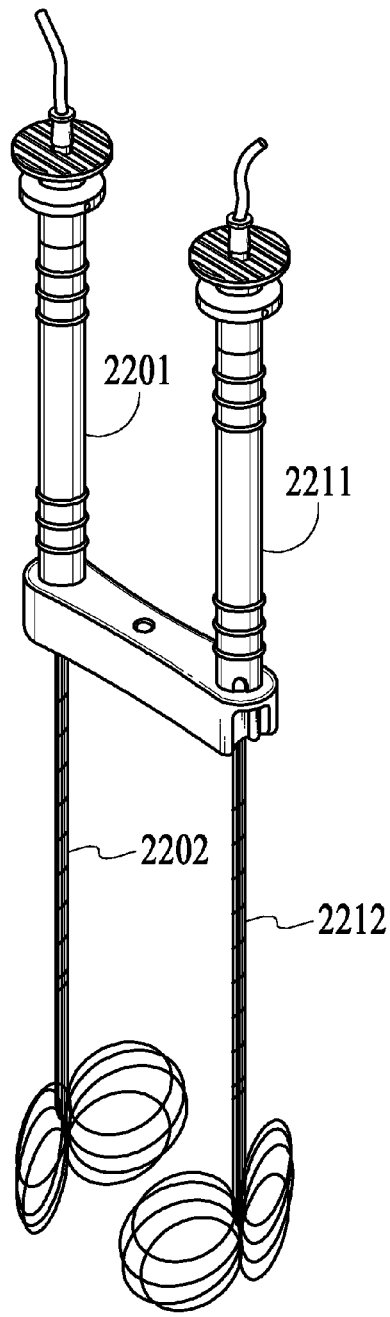
FIG. 22C is a perspective view of a dual-trocar ablation device, under the embodiment of FIG. 22A.
Figure 22E:
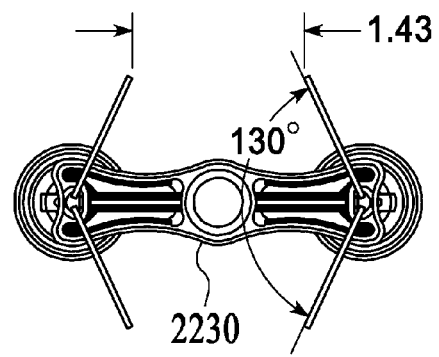
FIG. 22E is an end view of a dual-trocar ablation device of FIG. 22A, with a molded bridge assembly, under an embodiment.

FIG. 22D is an end view of a dual-trocar ablation device of FIG. 22A, and shows the electrodes 2204 and 2205 comprising electrode set 2203 extend from the body of trocar 2202 at an angle 2214 relative to one another as defined by the longitudinal axis of the trocar 2202, and the electrodes 2208 and 2209 comprising electrode set 2213 extend from the body of trocar 2212 at an angle 2218 relative to one another as defined by the longitudinal axis of the trocar 2212. The example device illustrated in FIGS. 22A-D is generally configured to create an ablation area on the order of 7.0 cm in diameter. This area results from a number of factors, such as the angle between electrodes within each electrode, and the distance between the electrode sets. For the embodiment shown in FIG. 22D, the angle between electrodes in each set is illustrated as 130° and the electrode spacing is 1.43", although it should be understood that many other angles and electrode spacings are possible. In one embodiment, the electrode spacing is defined by the width of bridge 2210. FIG. 22E is an end view of a dual-trocar ablation device of FIG. 22A, with a molded bridge assembly, under an embodiment. As shown in FIG. 22E, bridge 2230 includes a molded inner portion that is integrally molded to the handle assemblies 2301 and 2311 to fix the trocars firmly in positions relative to one another.

Figure 23A:
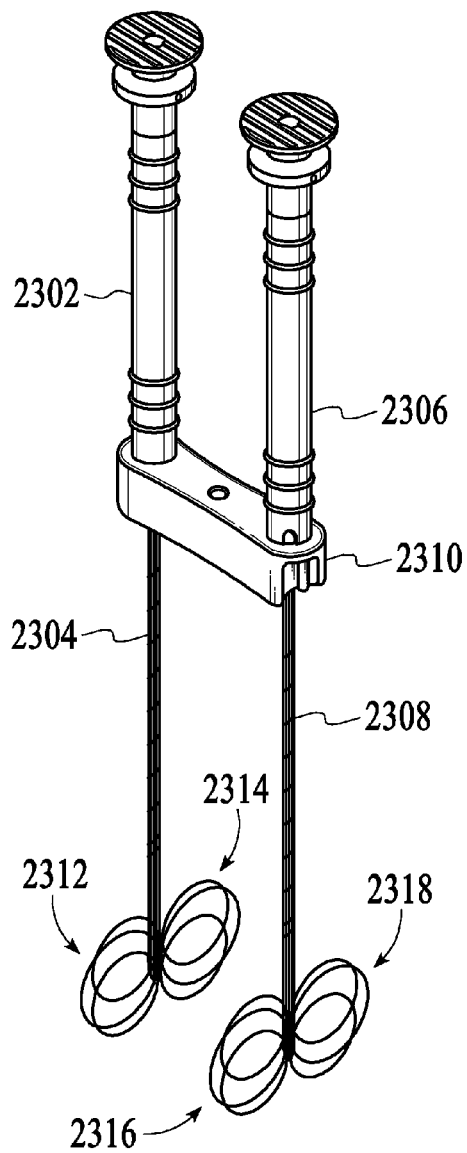
FIG. 23A illustrates a perspective view of a dual-trocar ablation device that uses one or more spiral electrodes in a planar array protruding from the distal end of each trocar.

In one embodiment, the angle between the electrode set deployed from a trocar can be 180°, so that the electrodes for each trocar are arrayed in a single plane relative to the longitudinal axis of the trocar. FIG. 23A illustrates a perspective view of a dual-trocar ablation device that uses one or more spiral electrodes in a planar array protruding from the distal end of each trocar. Ablation device 2300 of FIG. 23A has a first trocar 2304 protruding from a first handle assembly 2302, and a second trocar 2308 protruding from a second handle assembly 2306. The handle assemblies are coupled through bridge 2310, which keeps the trocars 2304 and 2308 at a fixed distance from one another. A first set of spiral electrodes 2312 is deployed from the distal end of trocar 2304 through orifices along one side of the trocar, and a second set of electrodes 2314 is deployed through orifices along the opposite side of the trocar 2304. Likewise, for trocar 2308, a first set of electrodes 2316 protrudes from a set of orifices along one side of the trocar, while a second set of electrodes 2318 protrudes from the opposite side of the trocar 2308. For the embodiment shown in FIG. 23A, three spiral electrodes comprise each set of electrodes 2312-2318, although other numbers of electrodes per set are possible. Upon deployment, each electrode per electrode set prescribes an elliptical shape, such as a full or nearly full circle of a defined radius, depending upon the length of the radius. Many different sizes and shapes for the deployed electrodes are possible, and the embodiment of FIG. 23A can be configured to produce ablation areas of 3.5 cm, 5 cm, and 7 cm depending upon different configuration variations.

Figure 23B:
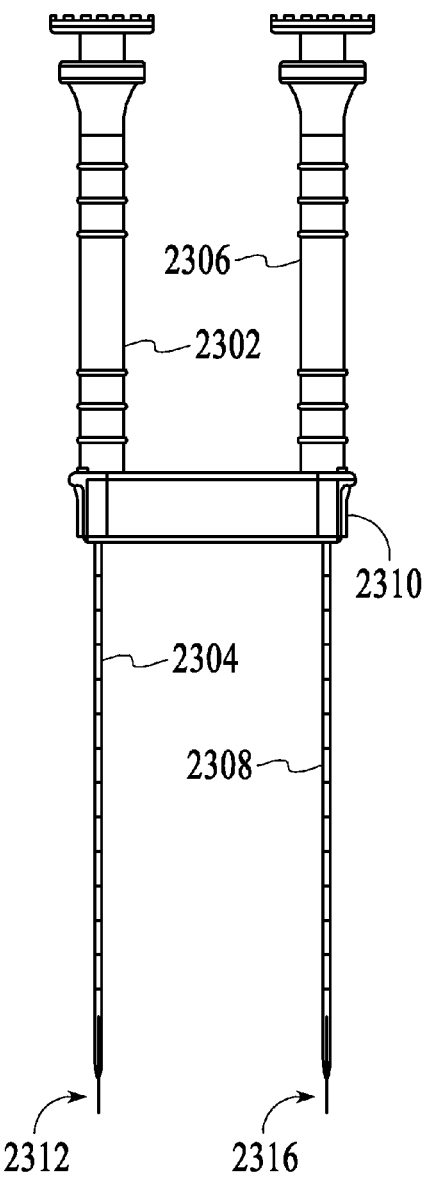
FIG. 23B is a frontal view of the dual-trocar ablation device, under the embodiment of FIG. 23A.
Figure 23C:
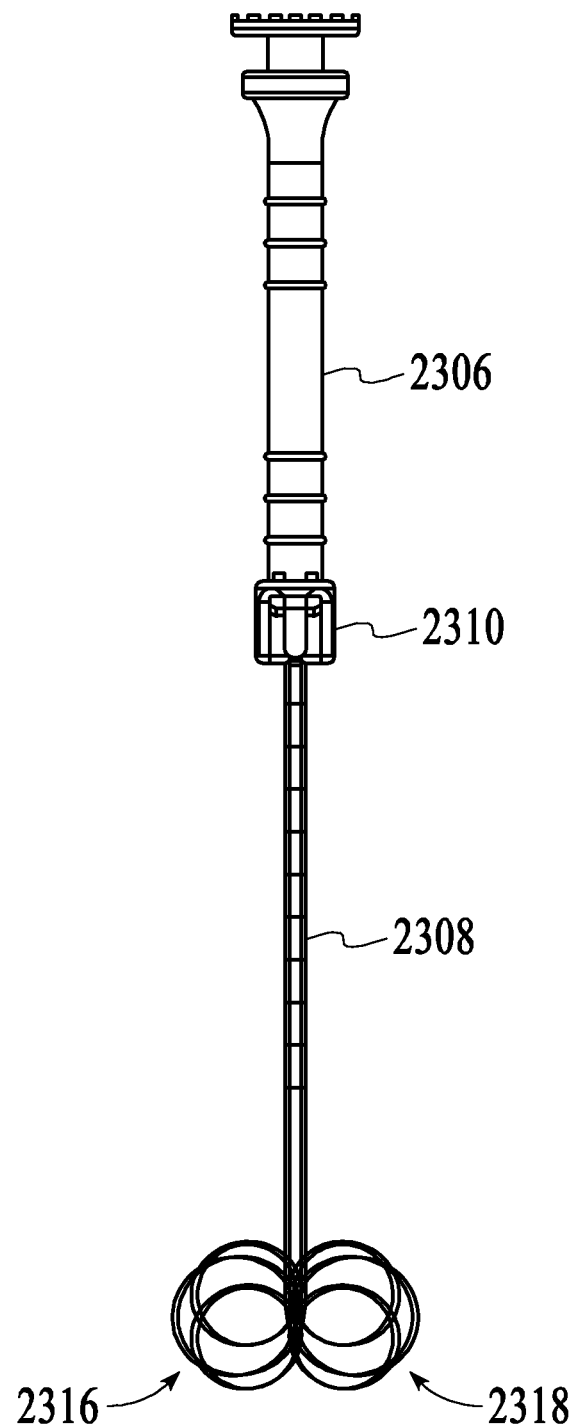
FIG. 23C is a side view of the dual-trocar ablation device, under the embodiment of FIG. 23A.
Figure 23D:
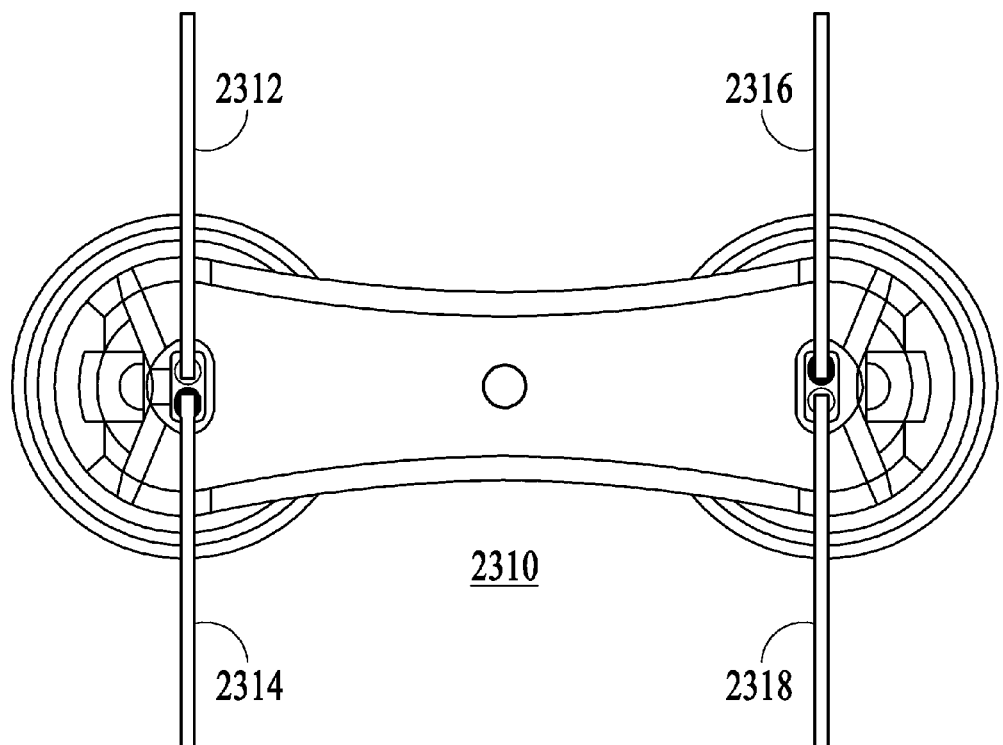
FIG. 23D is an end view of the dual-trocar ablation device, under the embodiment of FIG. 23A.

FIG. 23B is a frontal view of the dual-trocar ablation device of FIG. 23A. This view shows the sets of electrodes "head-on" relative to their respective trocars 2304 and 2308. As can be seen in FIG. 23B, the electrodes are aligned along a plane perpendicular to the plane of the paper. FIG. 23C is a side view of the dual-trocar ablation device of FIG. 23A. This view shows the ablation device of FIG. 23B in a "side-on" perspective. In this view the full range of deployed electrode sets 2316 and 2318 from either side of trocar 2308 can be seen. FIG. 23D is an end view of the dual-trocar ablation device of FIG. 23A. In this view the opposition of each set of electrodes per trocar can clearly be seen. Thus, electrode set 2312 is oriented 180° from electrode set 2314 and electrode set 2316 is oriented 180° from electrode set 2318.

Figure 24B:
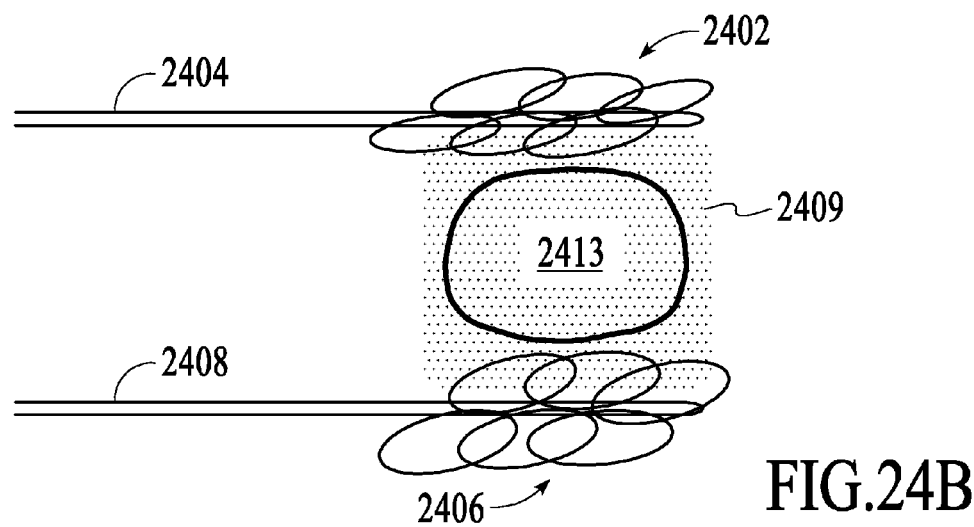
FIG. 24B illustrates the placement of the ablation device of FIG. 24A around an example region of target tissue.
Figure 24A:
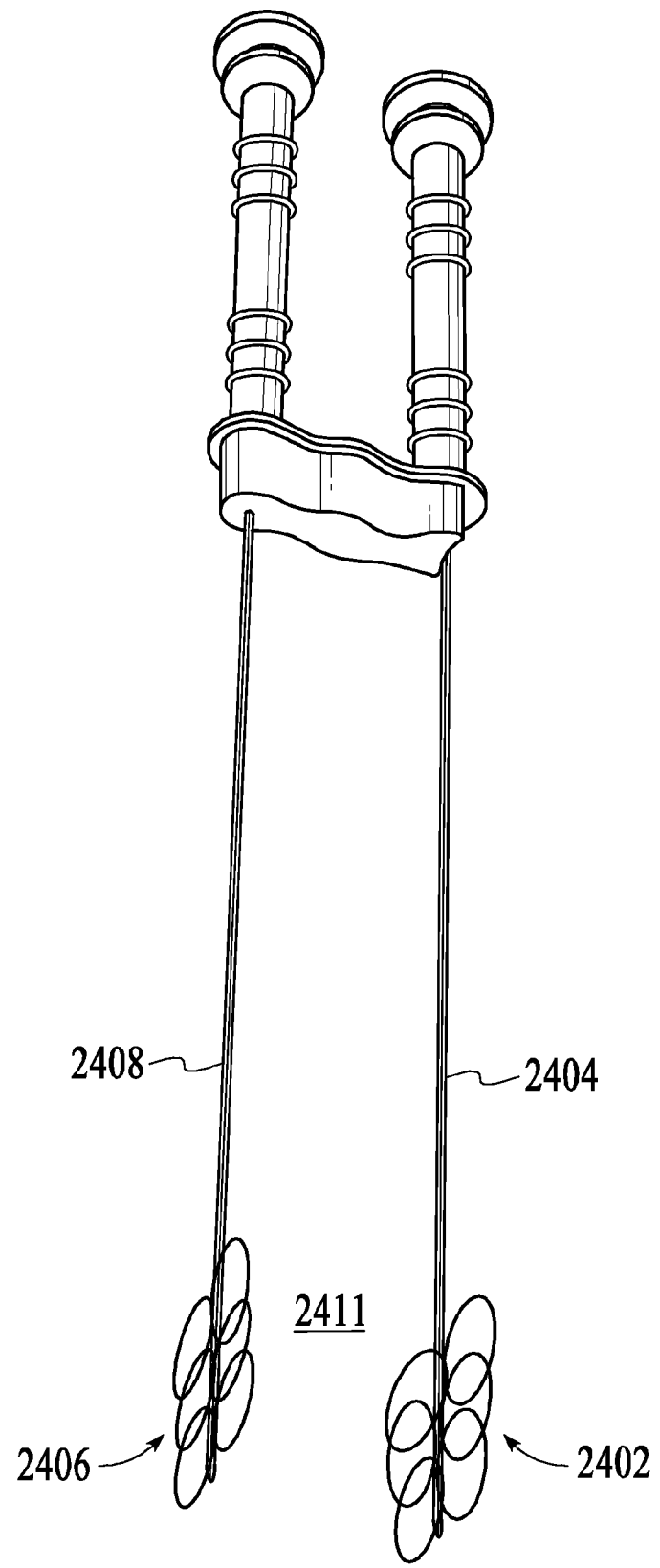
FIG. 24A is a perspective view of a dual-trocar ablation device with planar arrayed electrodes showing an ablation region defined by the spiral electrode sets protruding from the distal end of each trocar, under an embodiment.

The planar orientation of the pairs of electrode sets per trocar for the ablation device illustrated in FIGS. 23A-D provides for efficient energy delivery within a specific target area. FIG. 24A is a perspective view of a dual-trocar ablation device with planar arrayed electrodes showing an ablation region defined by the spiral electrode sets protruding from the distal end of each trocar, under an embodiment. As shown in FIG. 24A, electrode array 2402 protrudes from the distal end of trocar 2404, and electrode array 2406 protrudes from the distal end of trocar 2408. When fully deployed the electrodes arrays 2402 and 2406 define two planes on either side of region 2411. FIG. 24B illustrates the placement of the ablation device of FIG. 24A around an example region of target tissue. As shown in FIG. 24B, trocars 2404 and 2408 are placed such that electrode arrays 2402 and 2406 are positioned on either side of a target tissue area (e.g., a tumor) 2413. Upon the application of energy (e.g., RF energy) from the energy source, the electrode arrays project an energy field 2409 comprehensively within the area defined by the planes of the electrode arrays. In this case the target tissue 2413 is directly exposed to the applied energy.

Because target tissue, such as lesions or tumors are not always perfect spheres, many present ablation devices do not provide full ablation of the entire target area. The arrangement of the electrode arrays of FIG. 24A provides a comprehensive projection of energy within the target area and can accommodate targets of various different shapes and sizes. In one embodiment, the device of FIG. 24A can be configured in numerous bipolar configurations including, but not limited to, a 3 cm device with 15 cm long trocars, a 3 cm device with 25 cm long trocars, a 4 cm device with 15 cm long trocars, a 4 cm device with 25 cm long trocars, a 5 cm device with 15 cm long trocars, and a 5 cm device with 25 cm long trocars. Many other configurations are possible, depending upon the needs and constraints of the operating environment. The device of FIG. 24A can be used in any of percutaneous, laparoscopic, and open medical procedures. The device generally provides a reduced trocar gauge size and provides improved patient safety along with reduced treatment times due to its advantageous electrode configuration. It generally delivers efficient bipolar energy only within the target area, allowing medical professionals to tailor the ablation shape and size to the needs of the patient. It also allows for accurate electrode placement with appropriate margins, while enhancing safety by eliminating the requirement for ground pads and eliminating any need for lesion contact by electrodes.

Figure 25A:
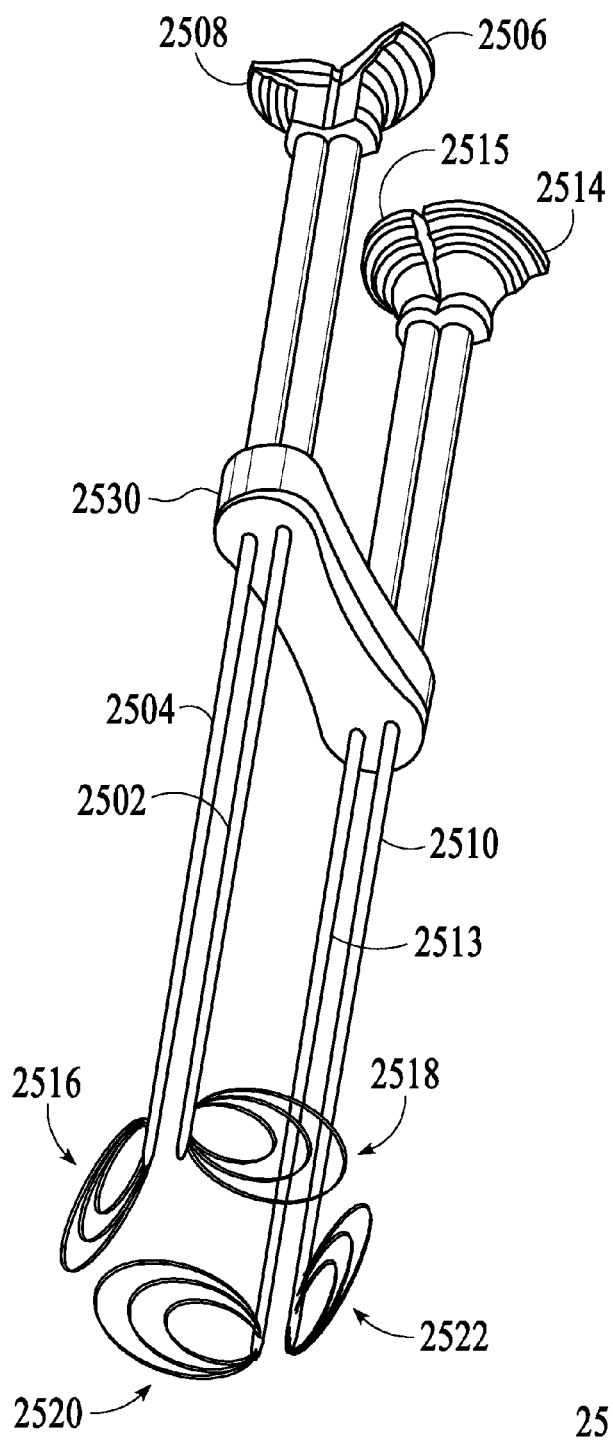
FIG. 25A is a perspective view of a multi-trocar ablation device with four separate trocars and one or more spiral electrodes in an array protruding from the distal end of each trocar, under an embodiment.

The ablation device of FIG. 24A is a dual-trocar device in which two trocars coupled together with a bridge are used to deploy respective electrode arrays. In an alternative embodiment, the ablation device can contain multiple-trocars that each deploy one or more electrode arrays. FIG. 25A illustrates a multi-trocar ablation device with four separate trocars, under an embodiment. In this embodiment, trocar 2510 protrudes from handle assembly 2514 which has a plunger for deploying and retracting electrode array 2522; trocar 2513 protrudes from handle assembly 2516 which has a plunger for deploying and retracting electrode array 2520; trocar 2502 protrudes from handle assembly 2506 which has a plunger for deploying and retracting electrode array 2518; and trocar 2504 protrudes from handle assembly 2508 which has a plunger for deploying and retracting electrode array 2516. For this embodiment, a molded bridge 2530 is formed around the four trocars to keep them in a fixed position relative to one another.

So that the device can be manipulated by a single person, the four trocars and their corresponding handle assemblies are arranged in pairwise, and the handles are shaped and arranged such that each pair of trocars can be manipulated by holding both corresponding handles in one hand. Thus, handles 2506 and 2508 form a single gripable shaft and handles 2514 and 2516 form a second gripable shaft.

Figure 25B:
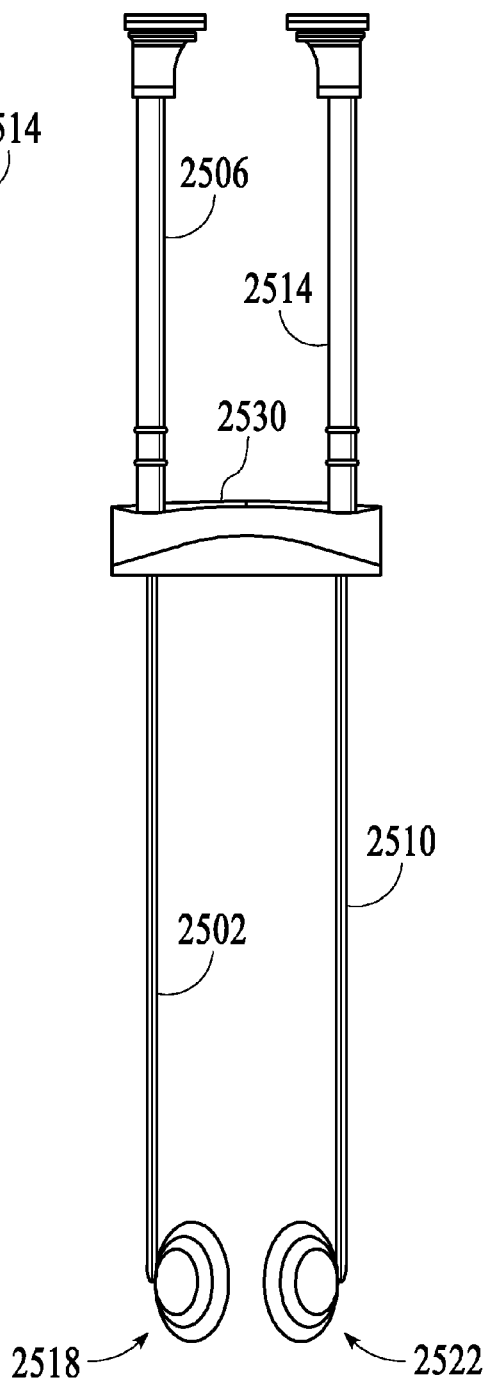
FIG. 25B is a front view of the multi-trocar ablation device, under the embodiment of FIG. 25A.

For the embodiment of FIG. 25A, the electrode array deployed from each trocar consists of a number (e.g., 3) of spiral electrodes arranged in a single plane. The angle between each pair of electrodes in the array of four electrodes can be selected based on the requirements of the application. FIG. 25B is a front view of the multi-trocar ablation device of FIG. 25A. This view shows electrode array 2518 deployed out of trocar 2502 and electrode array 2522 deployed out of trocar 2510. FIG. 25C is a side view of a dual-trocar ablation device of FIG. 25A. This view shows electrode array 2518 deployed out of trocar 2502 and electrode array 2516 deployed out of trocar 2504. FIG. 25D is an end view of a dual-trocar ablation device of FIG. 25A, and shows the angle between electrode array pairs 2516 and 2518, and 2522 and 2526. The orientation of electrode arrays illustrated in FIG. 25D is intended primarily as an example, and various different angles between electrode arrays may be provided.

Figure 26A:
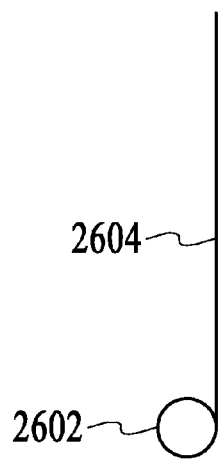
FIG. 26A illustrates a configuration of a spiral electrode array assembly deployed from the distal end of a trocar, under a first embodiment.

The embodiment of FIG. 25A shows that each electrode array consists of a number (e.g., three) of electrodes deployed in a circular shape out the distal end of a trocar. Various different numbers of electrodes, shape of deployed electrode, and size of deployed electrode pattern are possible, depending upon the requirements of the application. FIG. 26A illustrates a configuration of a spiral electrode array assembly deployed from the distal end of a trocar, under a first embodiment. In this embodiment, a single electrode wire 2602 is deployed in a circular shape out the end of trocar 2604, and adopts an elliptical shape (e.g., a circle) upon full deployment.

Figure 26B:
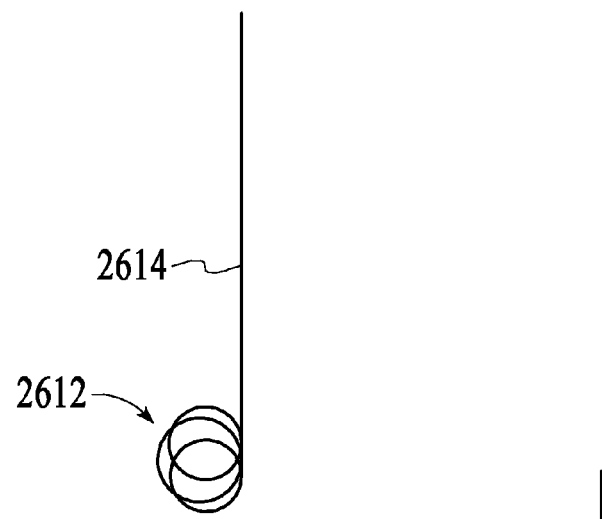
FIG. 26B illustrates a configuration of a spiral electrode array assembly deployed from the distal end of a trocar, under a second embodiment.
Figure 26C:
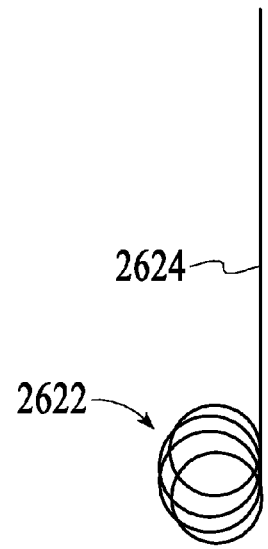
FIG. 26C illustrates a configuration of a spiral electrode array assembly deployed from the distal end of a trocar, under a third embodiment.

FIG. 26B illustrates a configuration of a spiral electrode array assembly deployed from the distal end of a trocar, under a second embodiment. In this embodiment, three electrode wires 2612 are deployed in an elliptical shape out the end of trocar 2614. FIG. 26C illustrates a configuration of a spiral electrode array assembly deployed from the distal end of a trocar, under a third embodiment. In this embodiment, four electrode wires 2622 are deployed in an elliptical shape out the end of trocar 2624.

The electrode configurations of FIGS. 26A-C can be used in any ablation device that features any number of trocars, and each trocar may include more than one electrode array of any of the configurations shown in FIGS. 26A-C. For the multiple electrode wire configurations of FIGS. 26B and 26C, the individual wires making up the electrode array may be deployed out of a single lumen on the distal end of the trocar, or they may be deployed out of a number of orifices along the distal end of the trocar.

Figure 27A:
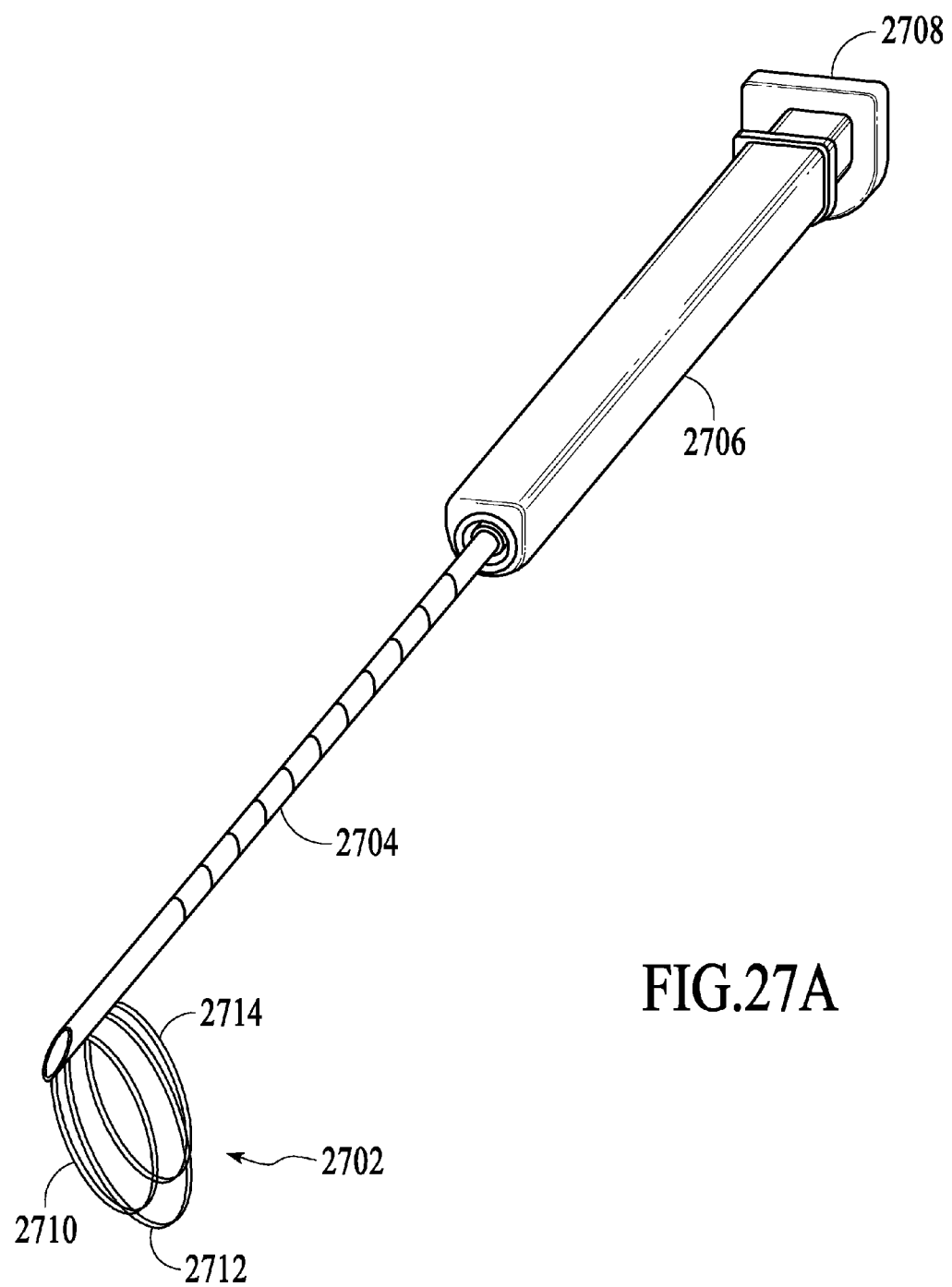
FIG. 27A shows a front perspective view of a single-trocar ablation device that uses one or more spiral electrodes in an array 2702 protruding fully or nearly fully from the distal end of a trocar 2704, under an embodiment.

For any of the multi-trocar implementations illustrated herein, in an alternative embodiment, one or more of the trocars may be deployed independently of the other trocars in a stand alone configuration. FIG. 27A shows a front perspective view of a single-trocar ablation device that uses one or more spiral electrodes in an array 2702 protruding fully or nearly fully from the distal end of a trocar 2704, under an embodiment. Trocar 2704 protrudes from an end of handle assembly 2706, which includes a plunger device 2708 that is used to deploy or retract the individual electrodes 2710, 2712, and 2714 of electrode array 2702. As shown in FIG. 27A, each electrode 2710-2714 deploys in a substantially circular shape from a respective orifice or lumen in the trocar. The diameter of each ellipse or circle defined by an electrode may be the same, or it may be different from one electrode to another.

Figure 27B:
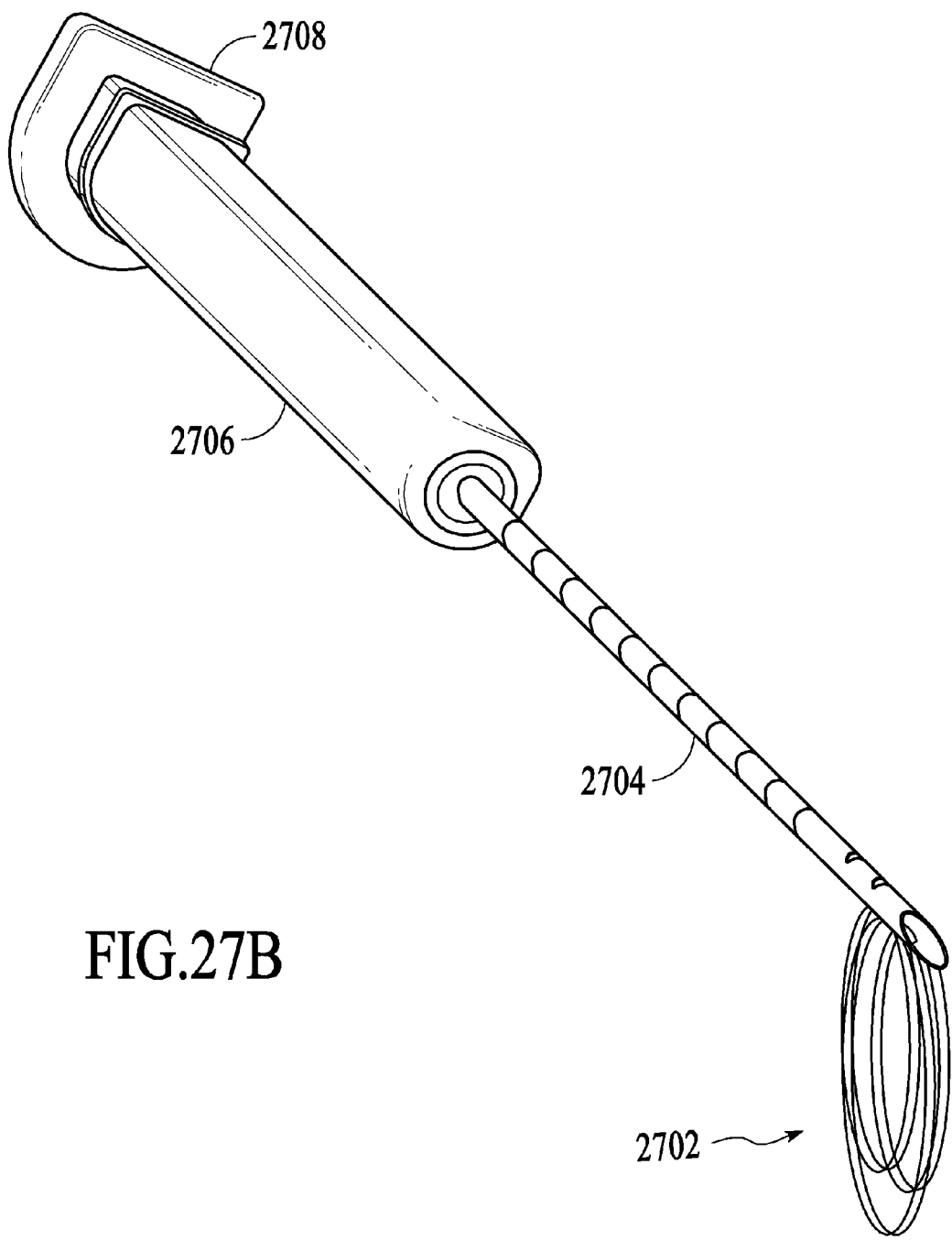
FIG. 27B shows another front perspective view of the single-trocar ablation device, under the embodiment, under the embodiment of FIG. 27A.
Figure 27C:
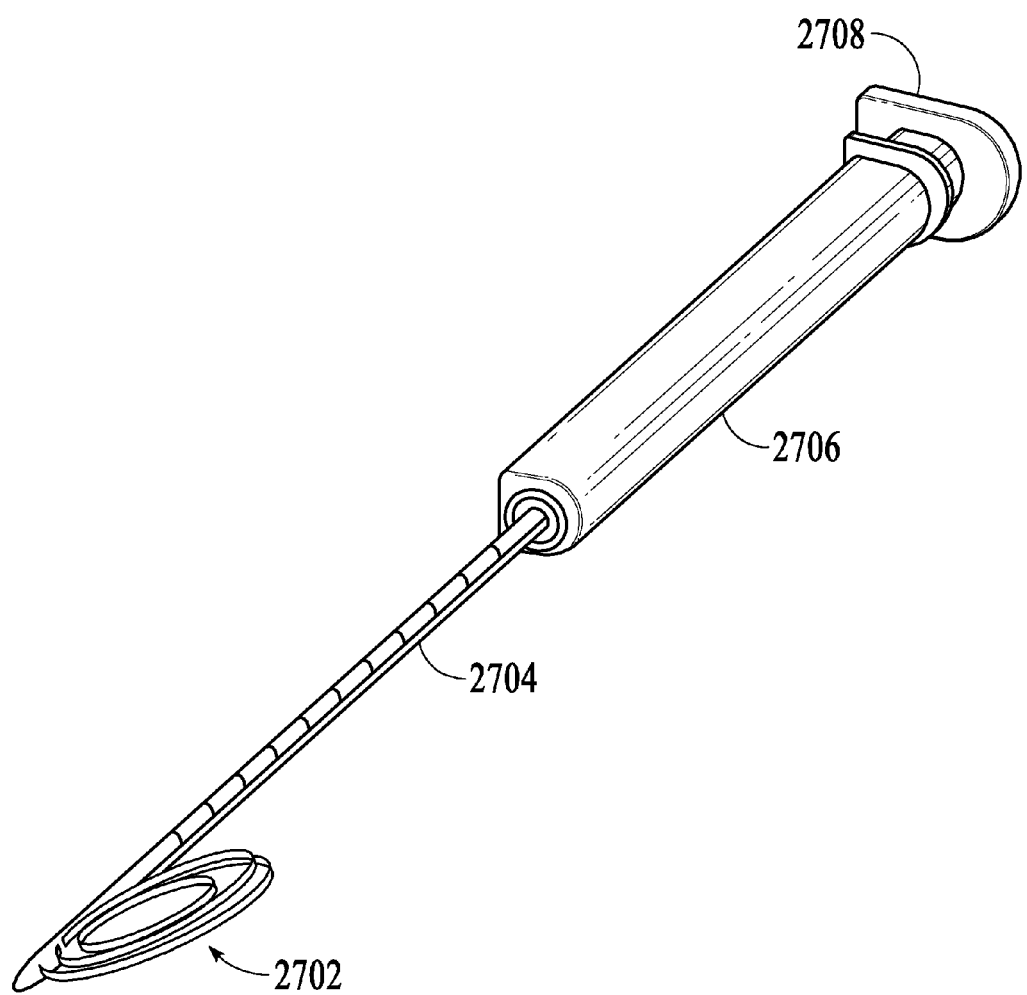
FIG. 27C shows yet another front perspective view of the single-trocar ablation device, under the embodiment of FIG. 27A.
Figure 27D:
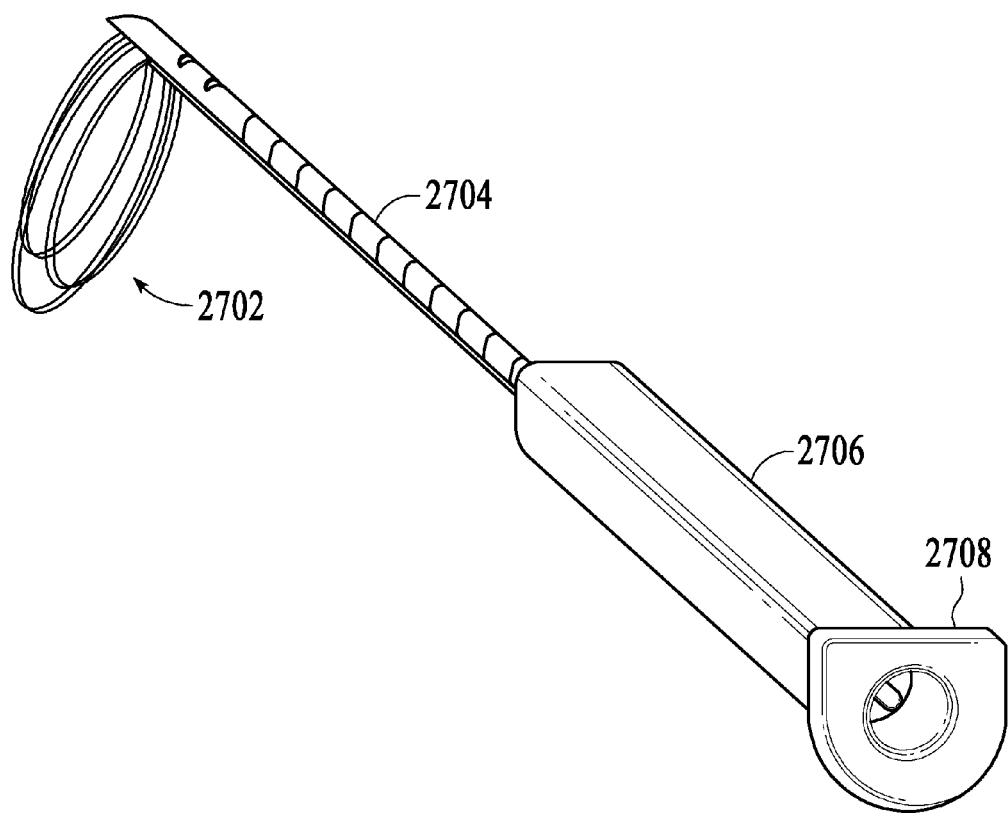
FIG. 27D shows a rear perspective view of the single-trocar ablation device, under the embodiment of FIG. 27A.

FIG. 27B shows another front perspective view of the single-trocar ablation device of FIG. 27A. This view shows in detail the extension of electrode array 2702 from one or more orifices in trocar 2704. FIG. 27C shows yet another front perspective view of the single-trocar ablation device of FIG. 27A. This shows the extension of the electrodes forward and outward as they are deployed out of the trocar. FIG. 27D shows a rear perspective view of the single-trocar ablation device of FIG. 27A. This view shows the single trocar ablation device from the perspective of the user. By gripping handle section 2706 and pulling or pushing on plunger handle 2708, the electrodes 2704 can be extended (deployed) from or retracted into trocar 2704.

Figure 28:
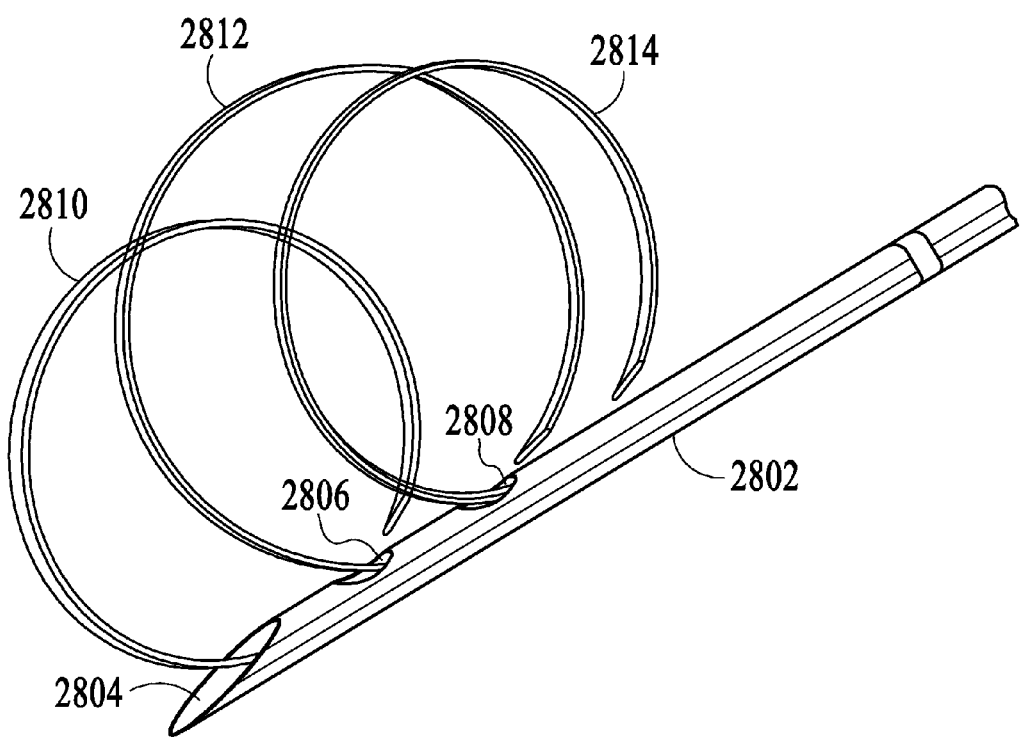
FIG. 28 is a detailed view of the deployment of electrodes out of a trocar, under an embodiment.

FIG. 28 is a detailed view of the deployment of electrodes out of a trocar, under and embodiment. As shown in FIG. 28, trocar 2802 includes a distal lumen 2804, and one or more (in this case, two) orifices 2806 and 2808 along a side of the trocar. Individual electrodes extend out or retract into a respective lumen or orifice, thus electrode 2801 extends from the distal lumen 2810, electrode 2812 extends from orifice 2806, and lumen 2814 extends from orifice 2808. Each electrode comprises a wire that curves into a defined shape when fully extended. For the embodiment of FIG. 28, each electrode spirals into a substantially circular (elliptical) shape. The size of the ellipse or circle, i.e., the tightness of the spiral, created by each electrode depends upon the length of the electrode when extended. The electrodes may be of the same extension length, and therefore define equal size circles, or they may be of different lengths to create different size circles. For example, in one embodiment, the middle electrode 2812 may feature a larger circle size than the outer electrodes 2810 and 2814. The configuration of the tightness of the spirals for the electrodes, and their relative sizes to one another depends upon the requirements and constraints of the operating conditions.

FIG. 28 is intended to be an example of one possible embodiment of electrodes extended from a trocar, and several other configurations are possible. For example, different numbers of lumens and electrodes may be provided (e.g., from two to six), more than one electrode may be extended from each lumen or orifice, and the electrodes may extend to form different shapes, other than circular. The electrodes may extend along a single plane relative to the longitudinal axis of trocar 2802, as shown in FIG. 28, or they may extend along different planes to one another. This can be accomplished by placing the lumens on different sides of the trocar, or by configuring the electrode wire so that it extends along a different trajectory to the other electrodes.

Figure 29A:
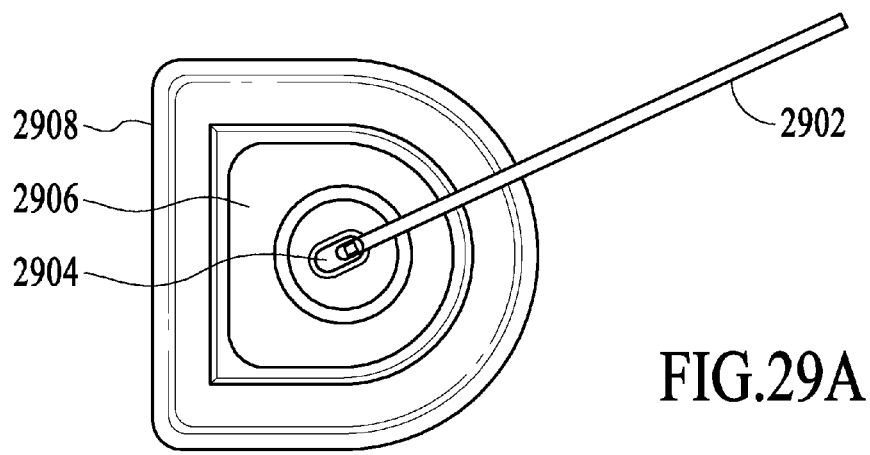
FIG. 29A shows a front view of a single-trocar ablation device that uses one or more spiral electrodes in an array protruding fully or nearly fully from the distal end of the trocar, under an embodiment.
Figure 29B:
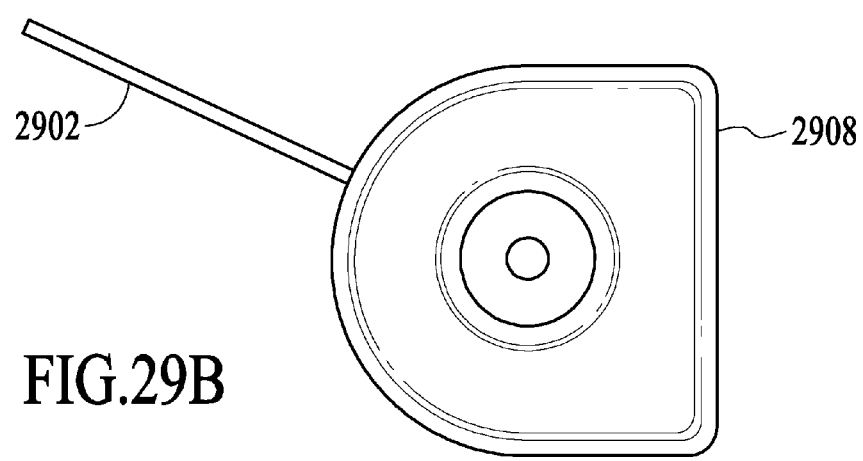
FIG. 29B shows a rear perspective view of the single-trocar ablation device, under the embodiment of FIG. 29A.

For the embodiment shown in FIGS. 27 and 28, the electrodes extend along a single plane relative to the longitudinal axis of trocar. This creates a planar ablation device that produces a relatively uniform and predictable energy radiation pattern in the target area. It also facilitates using several such devices in conjunction with one another to create a comprehensive ablation volume. FIG. 29A shows a front view of a single-trocar ablation device that uses one or more spiral electrodes in an array protruding fully or nearly fully from the distal end of the trocar, under an embodiment. Electrode or electrodes 2902 extend outwardly along a single plane relative to trocar 2904 and the handle assembly 2906. FIG. 29B shows a rear perspective view of the single-trocar ablation device of FIG. 29A. This view shows the device from the perspective of the user, and the upper surface of the deployment plunger 2908.

Figure 30A:
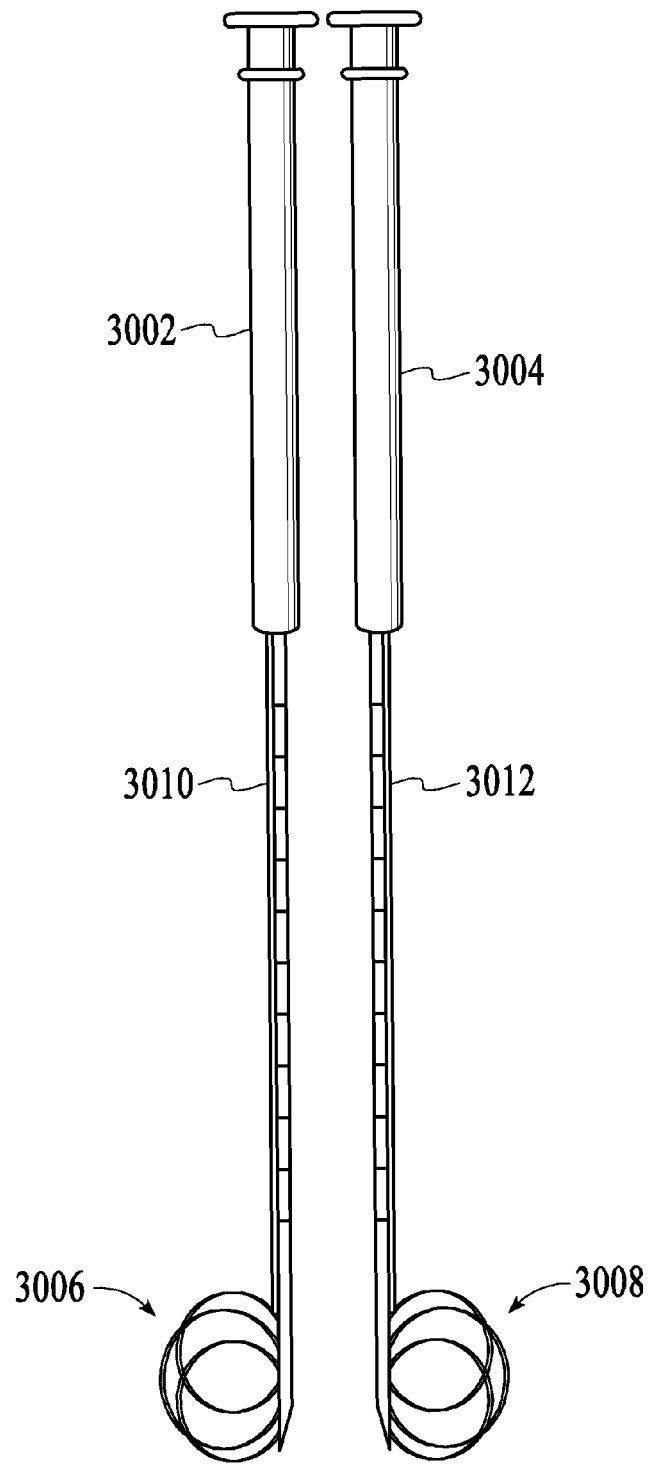
FIG. 30A shows a side view from a first side of a dual-trocar ablation system formed from the simultaneous use of two single-trocar ablation devices, each single-trocar ablation device using one or more spiral electrodes in an array protruding fully or nearly fully from the distal end of the corresponding trocar, under an embodiment.
Figure 30B:
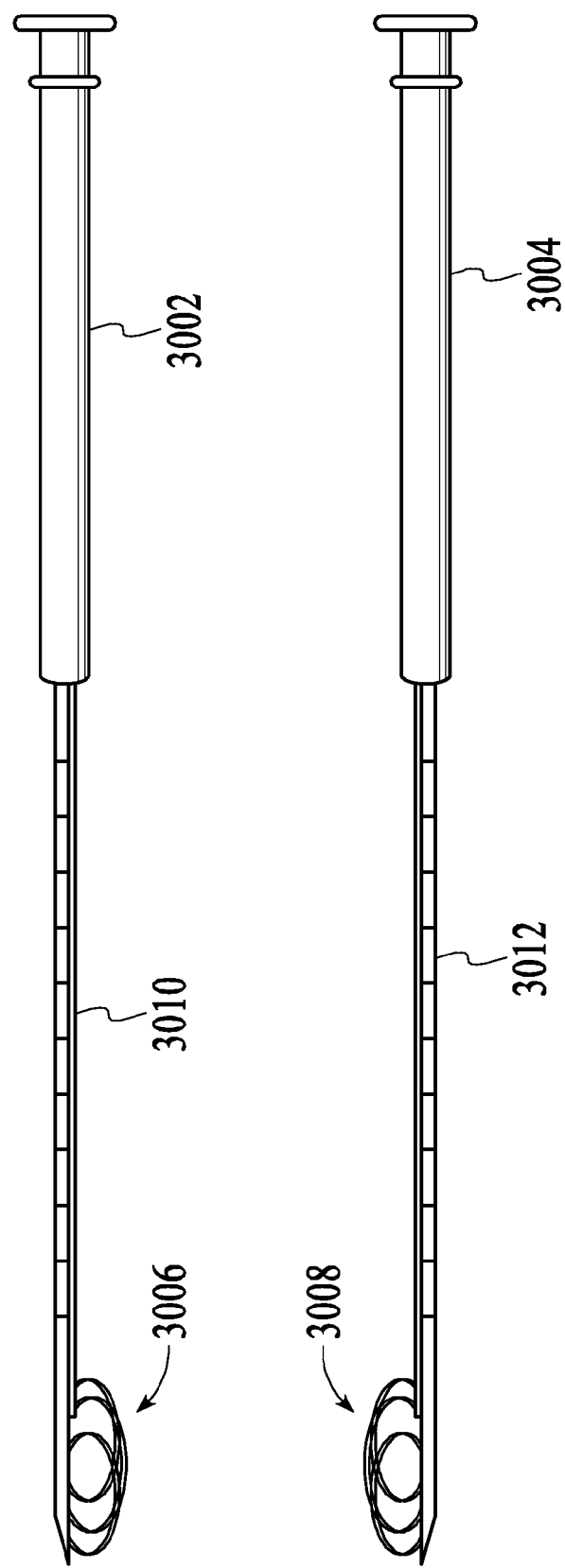
FIG. 30B shows a side view from a second side of a dual-trocar ablation system, under the embodiment of FIG. 30A.

The single planar ablation devices of FIGS. 28 and 29 may be used individually or in conjunction with one or more other similar devices. These devices can be used and manipulated independently of one another, or they may be used in conjunction with one or more other similar devices to create a dual or multi-trocar ablation system. In one embodiment, the two or more trocars may be coupled to each other using a bridge structure, such as bridge 2010 in FIG. 20, or they may be used independently from one another to afford the greatest amount of flexibility with regard to placement within the patient or subject. FIG. 30A shows a side view from a first side of a dual-trocar ablation system formed from the simultaneous use of two single-trocar ablation devices, each single-trocar ablation device using one or more spiral electrodes in an array protruding fully or nearly fully from the distal end of the corresponding trocar, under an embodiment. As shown in FIG. 30A, single-trocar electrode device 3002 is placed in a position substantially parallel to single-trocar device 3004 so that their respective electrode arrays 3006 and 3008 define an ablation area 3001. Through independent movement of either or both of devices 3002 and 3004, the area 3001 may be changed according to the constraints and requirements of the actual application. FIG. 30B shows a side view from a second side of a dual-trocar ablation system of FIG. 30A. This view shows that the electrode arrays 3006 and 3008 are positioned inward at a slight angle relative to one another. The device are held so that the trocars 3010 and 3012 are substantially parallel, but the electrode arrays are tilted inward by twisting the devices in toward each other.

Figure 31B:
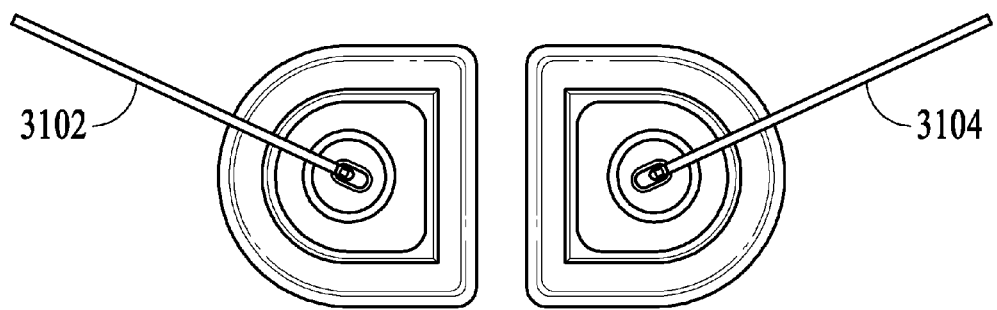
FIG. 31B shows a front view of the dual-trocar ablation system, under the embodiment of FIG. 31A.
Figure 31C:
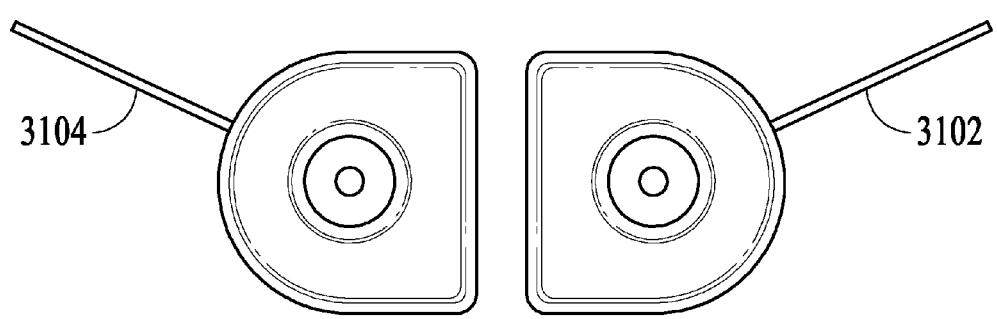
FIG. 31C shows a rear view of a dual-trocar ablation system, under the embodiment of FIG. 31A.

The ablation area 3001 created by the use of two separate single-trocar devices can be varied depending upon the placement of the electrode arrays relative to one another. Many different angles deployment are possible. FIG. 31A shows a front perspective view of a dual-trocar ablation system formed from the simultaneous use of two single-trocar ablation devices, each single-trocar ablation device using one or more spiral electrodes in an array protruding fully or nearly fully from the distal end of the corresponding trocar, under an embodiment. The orientation of a first plane formed by the first single-trocar ablation device electrodes relative to a second plane formed by the second single-trocar ablation device electrodes is such that the first and second planes intersect to collectively form a non-linear ablation surface. For this embodiment, the electrode arrays are deployed to point outward relative to one another. FIG. 31B shows a front view of the dual-trocar ablation system of FIG. 31A, and FIG. 31C shows a rear view of a dual-trocar ablation system of FIG. 31A. These views both show the angle formed by electrode arrays 3102 and 3104 to form a non-linear ablation surface.

Figure 32A:
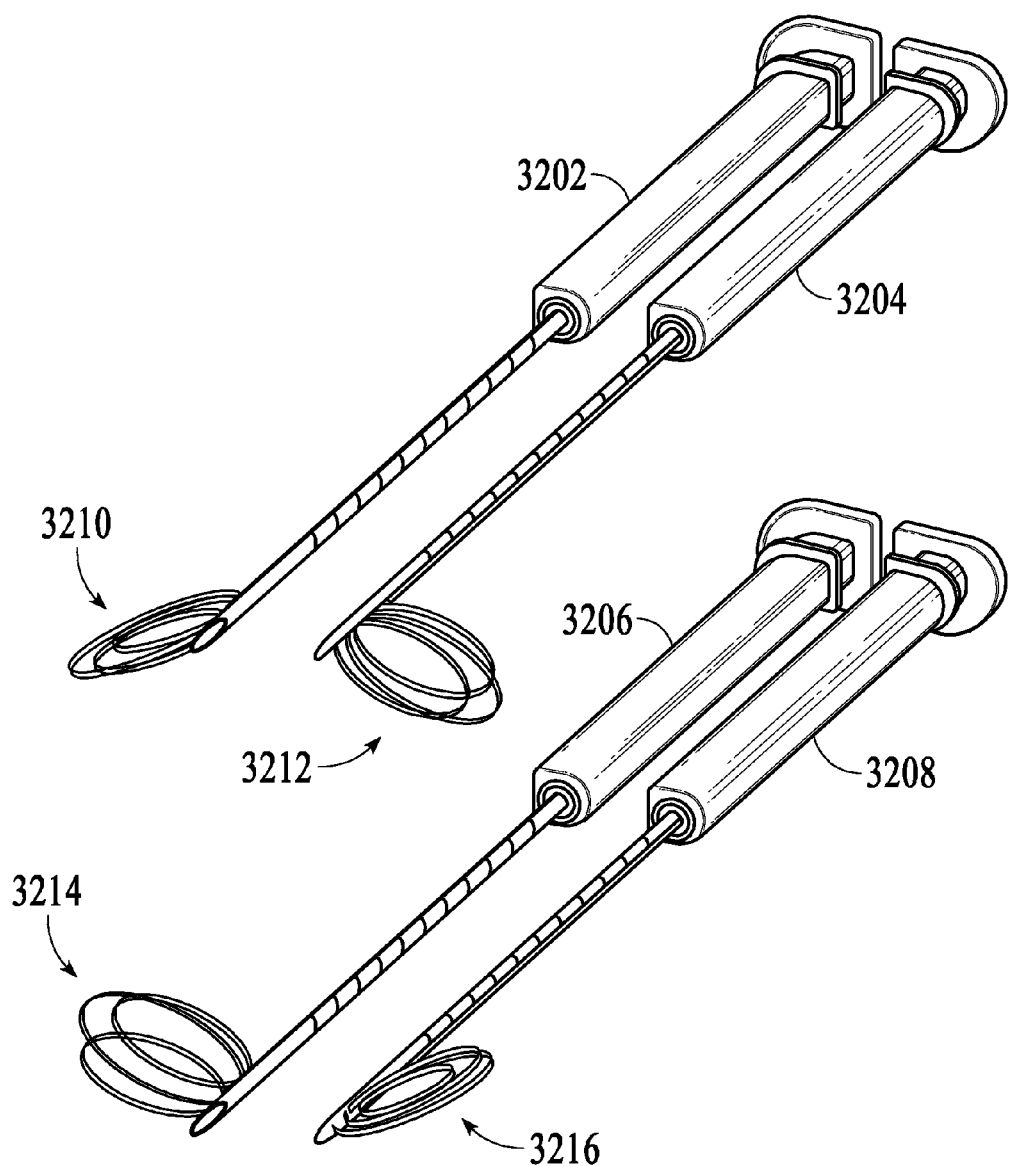
FIG. 32A shows a front perspective view of a quad-trocar ablation system formed from the simultaneous use of four single-trocar ablation devices, each single-trocar ablation device using one or more spiral electrodes in an array protruding fully or nearly fully from the distal end of the corresponding trocar, under an embodiment.

As stated above, more than any practical number of single-trocar ablation devices can be used independently of one another. In certain cases, two or more individual users can deploy their own device or devices in a treatment area provided there is enough room to so operate. FIG. 32A shows a front perspective view of a quad-trocar ablation system formed from the simultaneous use of four single-trocar ablation devices, each single-trocar ablation device using one or more spiral electrodes in an array protruding fully or nearly fully from the distal end of the corresponding trocar, under an embodiment. For this embodiment, four separate trocars 3202, 3204, 3206, and 3208 are positioned so that their respective electrode arrays 3210, 3212, 3214, and 3216 surround the target area in a desired manner. The orientation of a first plane formed by the first single-trocar ablation device electrode array 3210 relative to a second plane formed by the second single-trocar ablation device electrode array 3214 is such that the first and second planes intersect to collectively form a non-linear ablation surface. The orientation of the second plane formed by the second single-trocar ablation device electrode array 3212 relative to a third plane formed by the third single-trocar ablation device electrode array 3216 is such that the second and third planes intersect to collectively form a non-linear ablation surface. The orientation of the third plane formed by the third single-trocar ablation device electrode array 3216 relative to a fourth plane formed by the fourth single-trocar ablation device electrode array 3214 is such that the third and fourth planes intersect to collectively form a non-linear ablation surface. The orientation of the fourth plane formed by the fourth single-trocar ablation device electrode array 3214 relative to the first plane formed by the first single-trocar ablation device electrode array 3210 is such that the fourth and first planes intersect to collectively form a non-linear ablation surface.

Figure 32B:
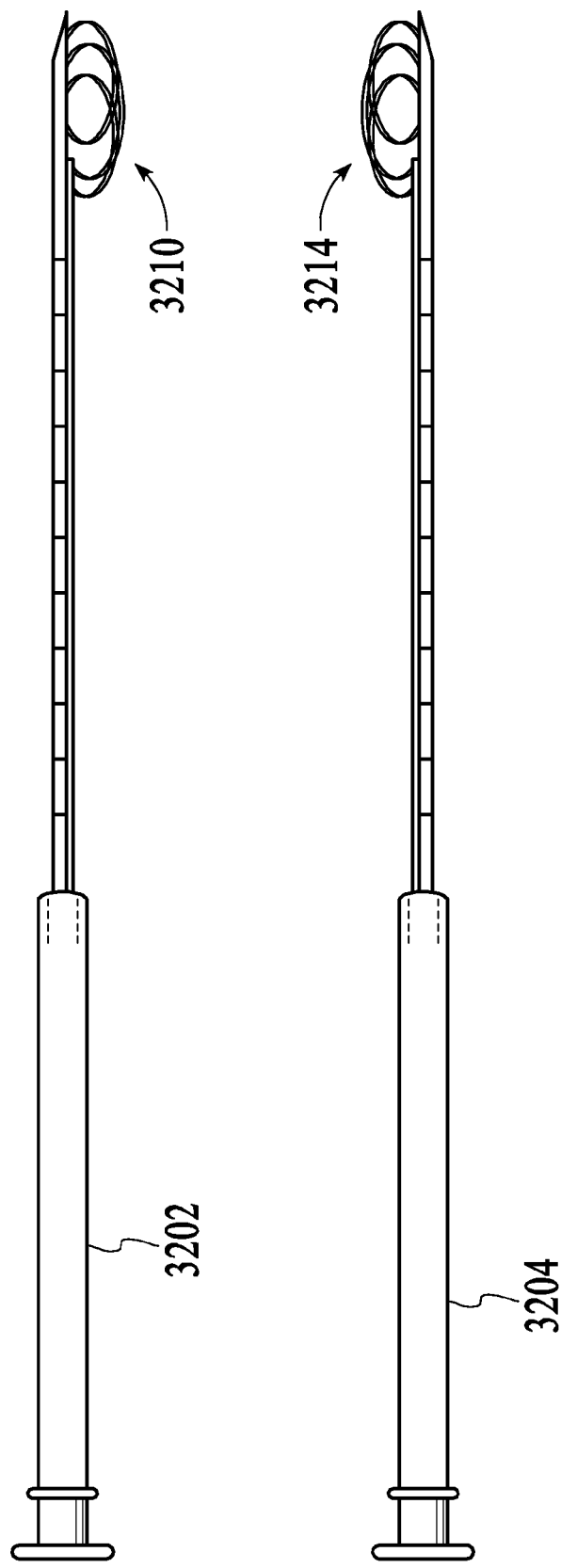
FIG. 32B shows a side view of a quad-trocar ablation system of FIG. 32A formed from the simultaneous use of four single-trocar ablation devices.

FIG. 32B shows a side view of a quad-trocar ablation system of FIG. 32A formed from the simultaneous use of four single-trocar ablation devices. As shown in this Figure, each single-trocar ablation device uses one or more spiral electrodes in an array protruding partially from the distal end of the corresponding trocar. This example embodiment shows a particular amount of extension of the spiral electrodes for each single-trocar ablation device; however, the particular amount of extension shown is provided as an example only as the actual extent to which the spiral electrodes of each single-trocar ablation device are partially extended can vary among each ablation device of the ablation system as appropriate to the ablation procedure in which the ablation system is used as well as the desired ablation volume.

Figure 32C:
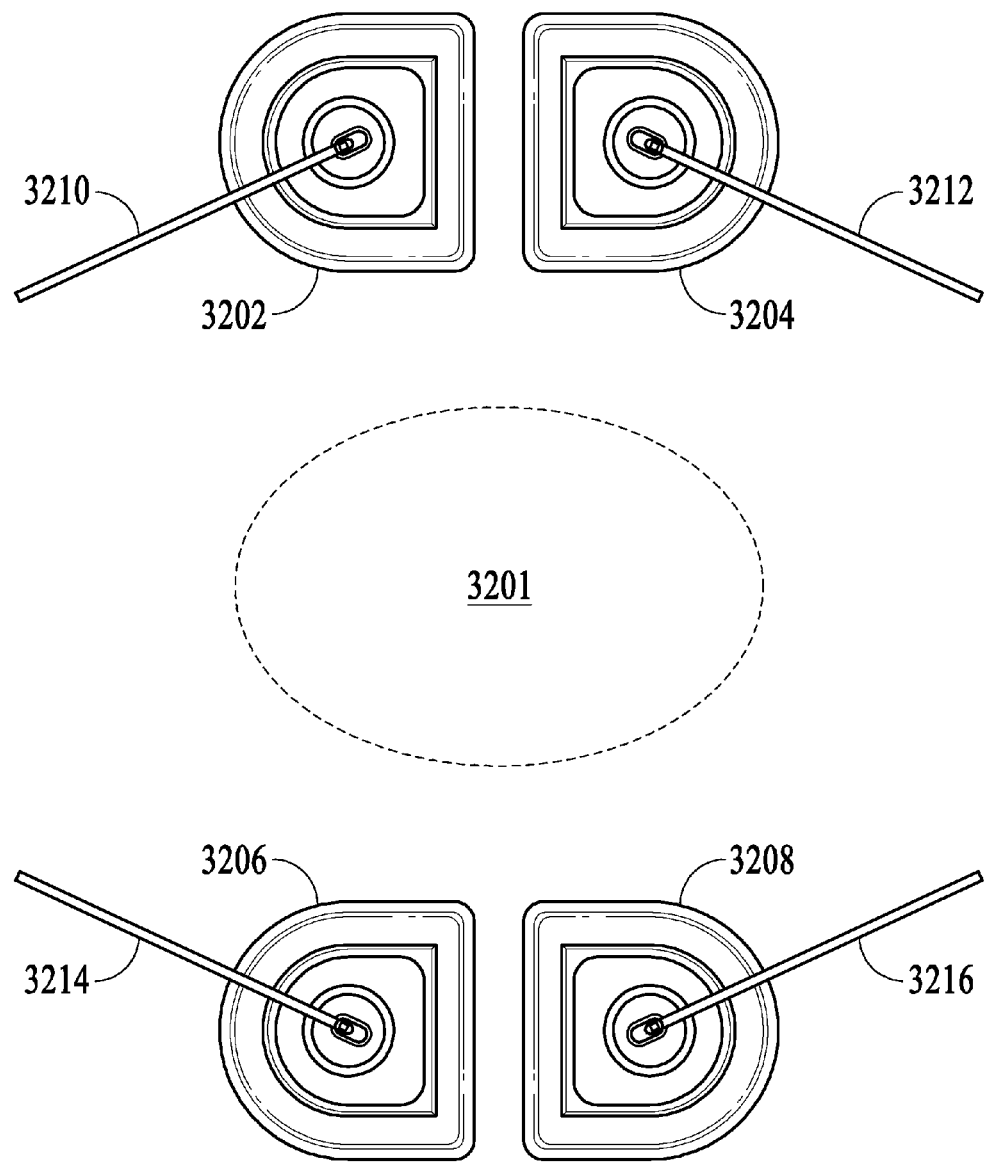
FIG. 32C shows a front view of a quad-trocar ablation system of FIG. 32A formed from the simultaneous use of four single-trocar ablation devices.

FIG. 32C shows a front view of a quad-trocar ablation system of FIG. 32A formed from the simultaneous use of four single-trocar ablation devices. This view shows the relative angle between each pair of electrode arrays 3210, 3212, 3214, and 3216, as they are deployed to encircle the target area 3201.

Figure 32D:
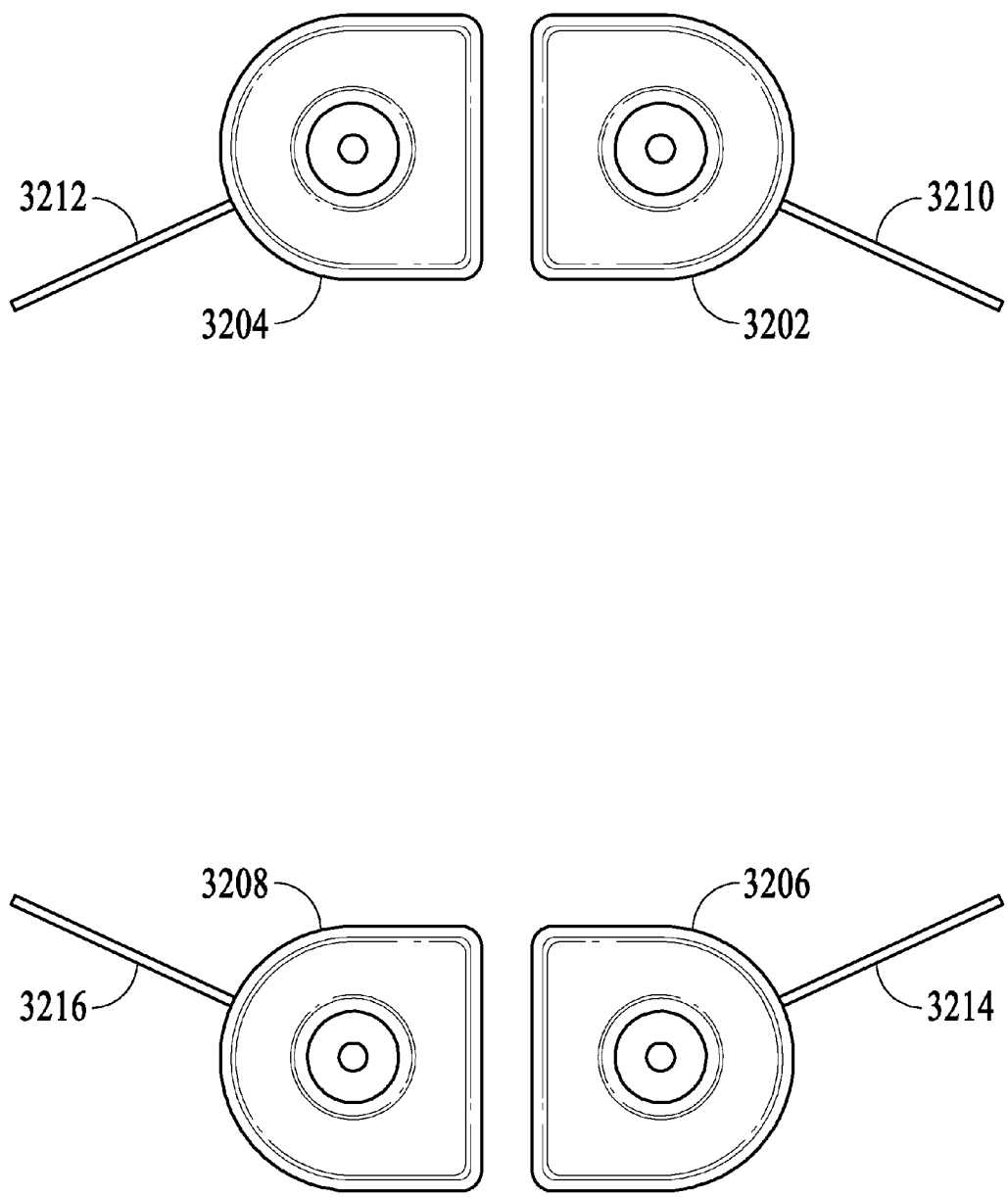
FIG. 32D shows a rear view of a quad-trocar ablation system of FIG. 32A formed from the simultaneous use of four single-trocar ablation devices.

FIG. 32D shows a rear view of a quad-trocar ablation system of FIG. 32A formed from the simultaneous use of four single-trocar ablation devices. This view shows the device from the perspective of the user, and the upper surface of the deployment plungers for each of the devices 3202, 3204, 3206, and 3208. Each of the electrode arrays can be deployed to any extended length through appropriate manipulation of the deployment plungers.

Figure 33:
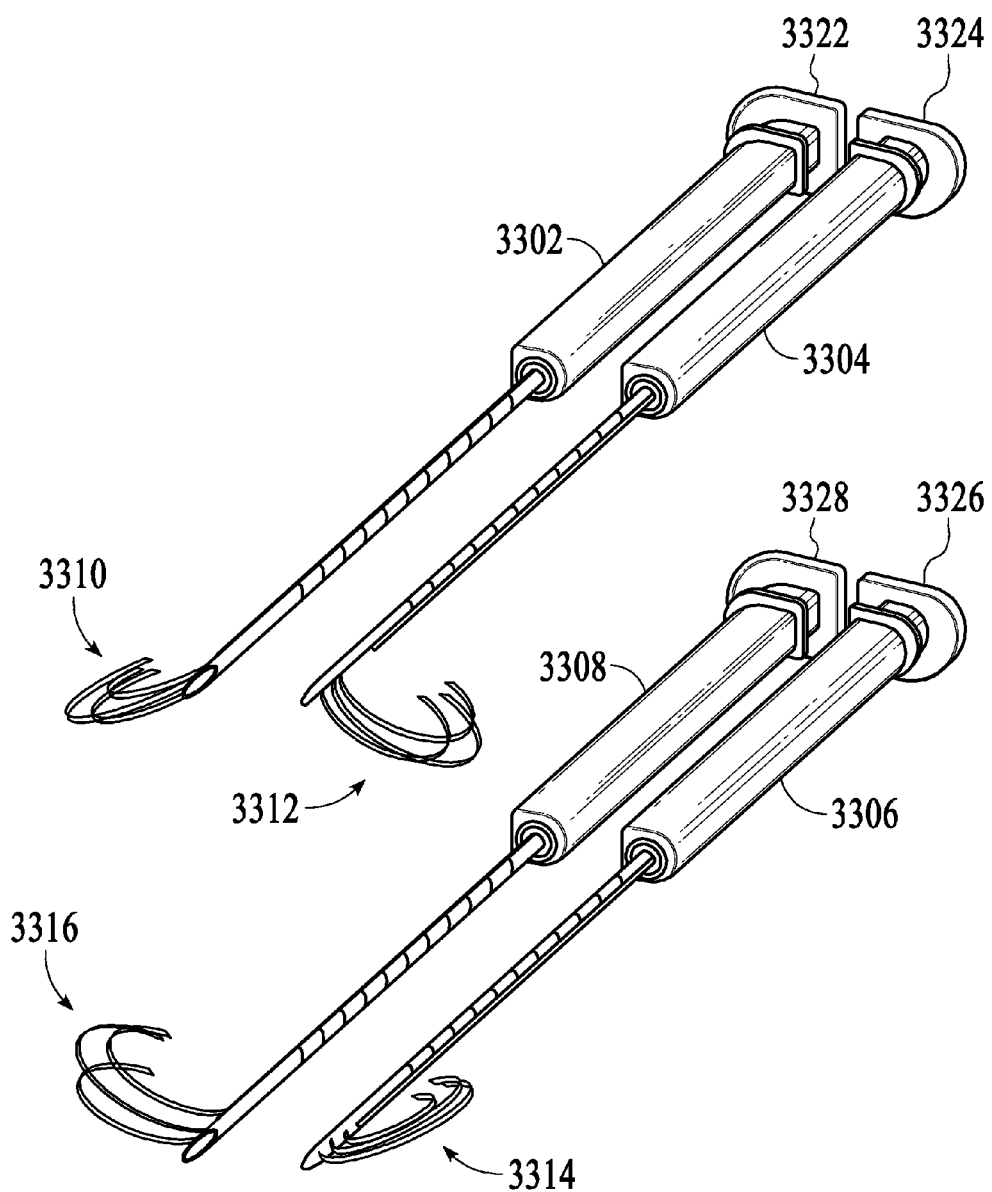
FIG. 33 illustrates a quad-trocar ablation system in which the electrode arrays are deployed from their respective trocars at less than full extension length.

In typical use, all the electrode arrays in a multi-trocar device may be simultaneously deployed to the same length within the target area. Alternatively, one or more of the electrode arrays may be deployed to different lengths to create different size and shape ablation areas. This allows the user to target specific types of non-uniform or hard to access target tissue areas. FIG. 33 illustrates a quad-trocar ablation system in which the electrode arrays are deployed from their respective trocars at less than full extension length, under an embodiment. Each single trocar device 3302, 3304, 3306, and 3308 of the quad-trocar ablation system has a respective electrode array 3310, 3312, 3314, and 3316 extending from the distal end of the trocar. The amount of extension of each electrode array is controlled by the position of the plunger 3322, 3324, 3326, and 3328 at the end of each device. As can be seen in FIG. 33, the electrodes in each array 3310-3316 do not form a complete circle, as is the case for the embodiment illustrated in FIG. 32A. For the example deployment of FIG. 33, the electrode arrays 3310-3316 are shown extended to approximately the same length relative to their trocars. As noted above, some electrode arrays can be extended to different lengths, such as fully extended or retracted, depending upon the application requirements. The size and shape of the ablation area can be effectively fine-tuned by selective extension of the independent electrode arrays. Thus, this example embodiment shows a particular amount of extension of the spiral electrodes for each single-trocar ablation device; however, the particular amount of extension shown is provided as an example only as the actual extent to which the spiral electrodes of each single-trocar ablation device are partially extended can vary among each ablation device of the ablation system as appropriate to the ablation procedure in which the ablation system is used as well as the desired ablation volume.

Figure 34A:
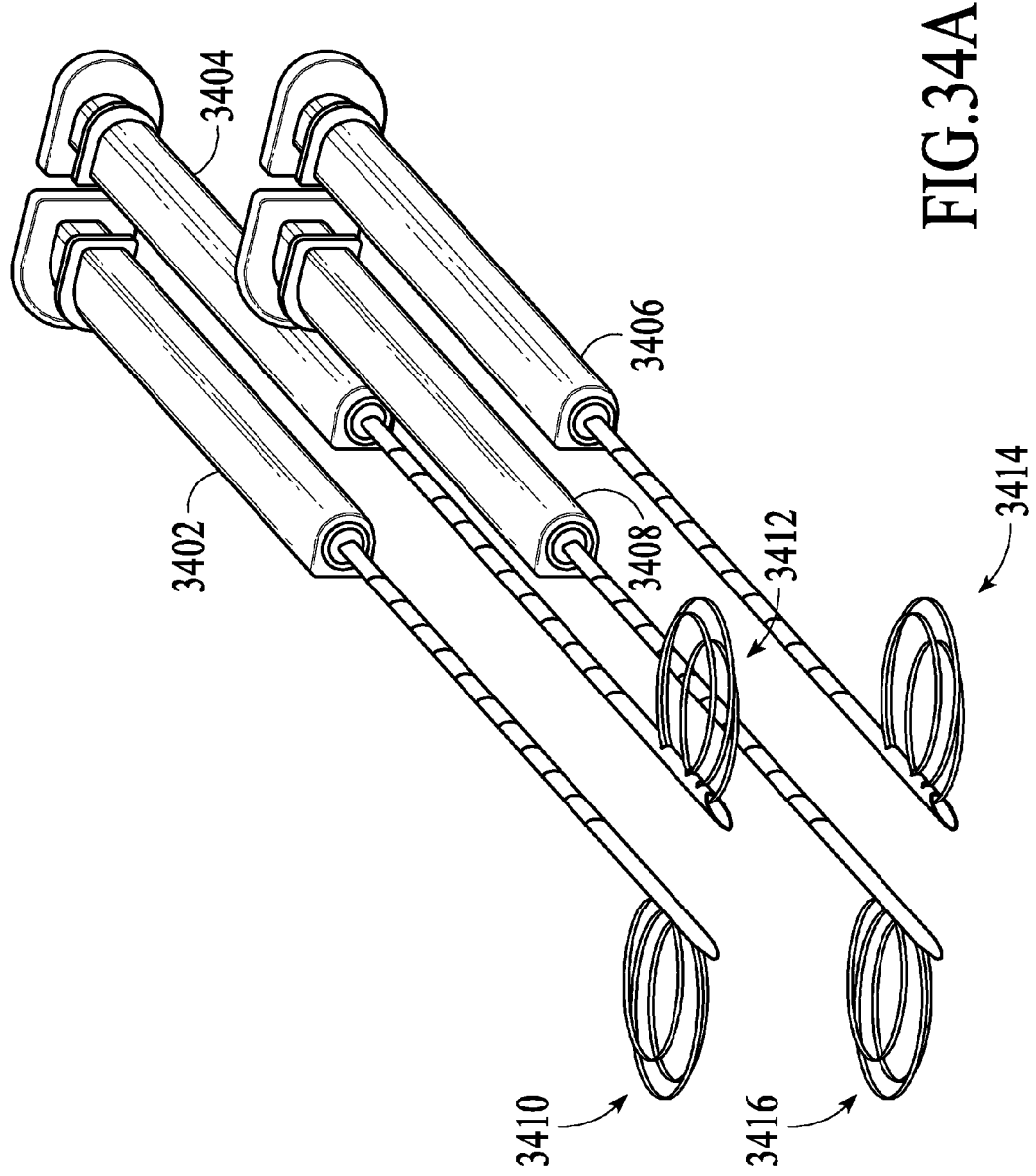
FIG. 34A shows a front perspective view of a quad-trocar ablation system formed from the simultaneous use of four single-trocar ablation devices, each single-trocar ablation device using one or more spiral electrodes in an array protruding fully or nearly fully from the distal end of the corresponding trocar, under an embodiment.

For the embodiment shown in FIGS. 32A-D, the angle created between each pair of electrode arrays is created in part by the angle of extension of each electrode array relative to the longitudinal axis of its respective trocar. This angle can also be defined by the angle in which the device is placed with respect to the target area. In one embodiment, a multi-trocar ablation system employs separate trocars in which the electrode array extends substantially perpendicular from the longitudinal axis of the trocar. FIG. 34A shows a front perspective view of a quad-trocar ablation system formed from the simultaneous use of four single-trocar ablation devices, with each single-trocar ablation device using one or more spiral electrodes in an array protruding fully or nearly fully from the distal end of the corresponding trocar, under an embodiment. The orientation of a first plane formed by the first single-trocar ablation device electrode array 3410 relative to a second plane formed by the second single-trocar ablation device electrode array 3412 is such that the first and second planes intersect to collectively form a first ablation plane. The orientation of the third plane formed by the third single-trocar ablation device electrode array 3414 relative to a fourth plane formed by the fourth single-trocar ablation device electrode array 3416 is such that the third and fourth planes intersect to collectively form a second ablation plane. The orientation of the first ablation plane relative to the second ablation plane is parallel or nearly parallel.

Figure 34B:
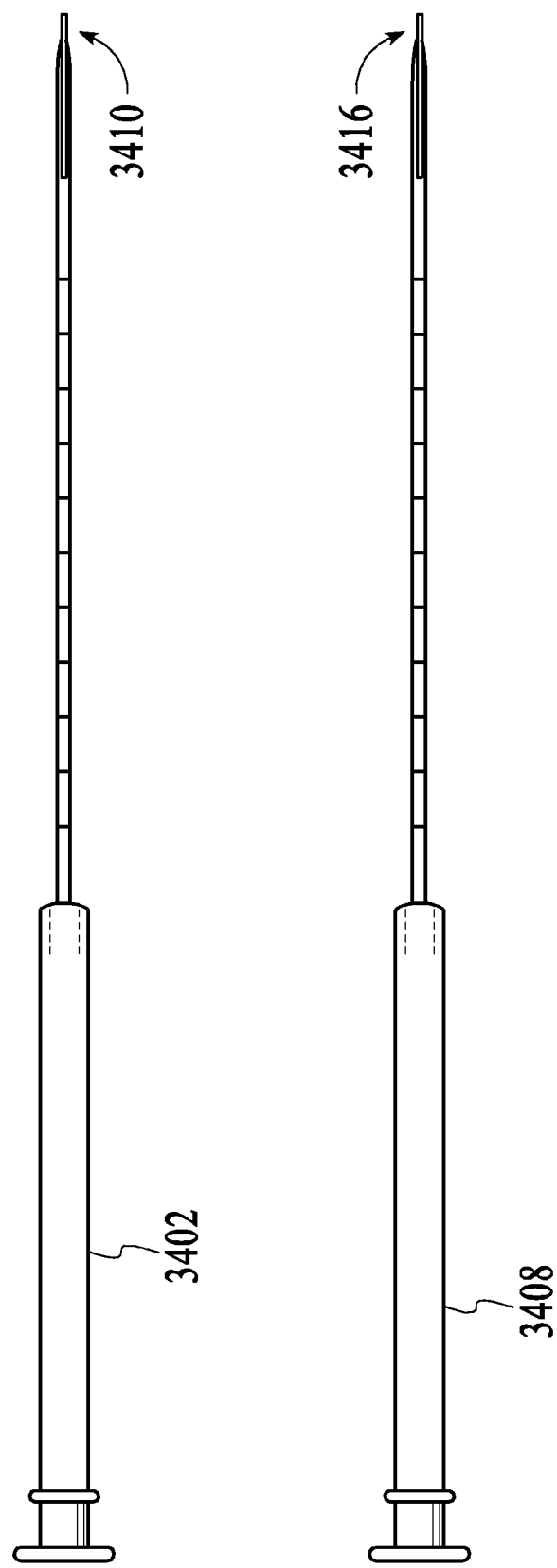
FIG. 34B shows a side view of a quad-trocar ablation system of FIG. 34A formed from the simultaneous use of four single-trocar ablation devices, under an embodiment.

FIG. 34B shows a side view of a quad-trocar ablation system of FIG. 34A formed from the simultaneous use of four single-trocar ablation devices. This view illustrates the substantially parallel disposition of the electrode arrays 3410 and 3416 when the single trocar devices 3402 and 3408 are oriented by the user parallel to one another. This view obscures the second pair of single trocar devices 3404 and 3406, but it is to be understood that the relative orientation of these devices and electrode arrays 3412 and 3414 is identical.

Figure 34C:
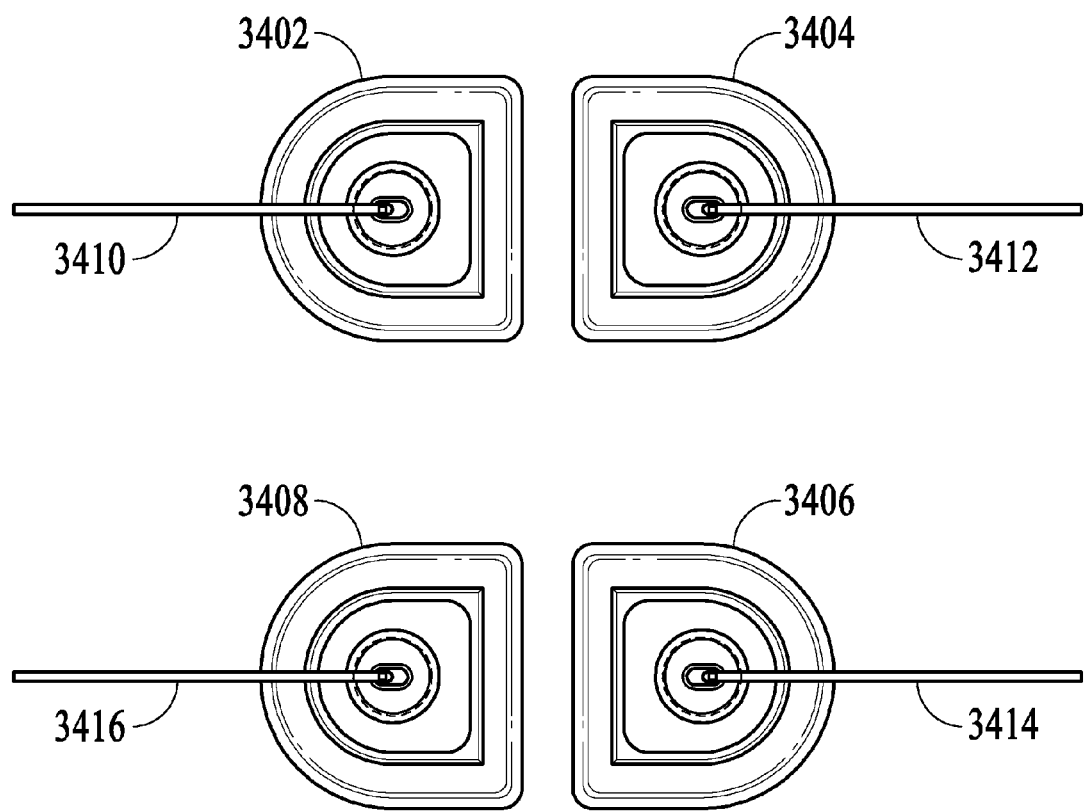
FIG. 34C shows a front view of a quad-trocar ablation system of FIG. 34A formed from the simultaneous use of four single-trocar ablation devices, under an embodiment.

FIG. 34C shows a front view of a quad-trocar ablation system of FIG. 34A formed from the simultaneous use of four single-trocar ablation devices. This view shows the orientation of electrode array pair 3410 and 3412 to form a first ablation plane, and the orientation of electrode array pair 3414 and 3416 to form a second ablation plane. For the embodiment shown, electrode pairs 3410 and 3416 are oriented substantially parallel to one another, and electrode pairs 3412 and 3414 are oriented substantially parallel to one another. This results in the first ablation plane being substantially parallel to the second ablation plane.

Figure 34D:
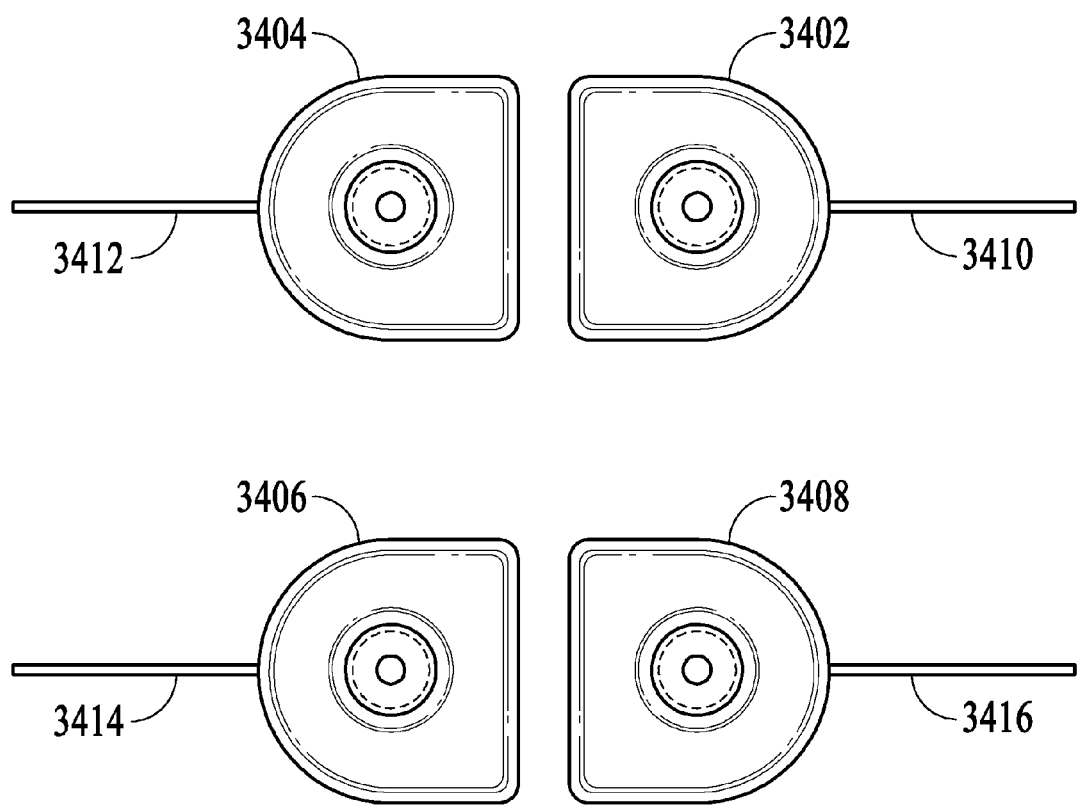
FIG. 34D shows a rear view of a quad-trocar ablation system of FIG. 34A formed from the simultaneous use of four single-trocar ablation devices, under an embodiment.

FIG. 34D shows a rear view of a quad-trocar ablation system of FIG. 34A formed from the simultaneous use of four single-trocar ablation devices. This view shows the device from the perspective of the user, and the upper surface of the deployment plungers for each of the devices 3402, 3404, 3406, and 3408. Each of the electrode arrays can be deployed to any extended length through appropriate manipulation of the deployment plungers. Each of the electrode arrays can be deployed to any extended length through appropriate manipulation of the deployment plungers.

In typical use, all the electrode arrays in a multi-trocar device may be simultaneously deployed to the same length within the target area. Alternatively, one or more of the electrode arrays may be deployed to different lengths to create different size and shape ablation areas. This allows the user to target specific types of non-uniform or hard to access target tissue areas. FIG. 35 illustrates a quad-trocar ablation system in which the electrode arrays are deployed from their respective trocars at less than full extension length, under an embodiment. Each single trocar device 3502, 3504, 3506, and 3508 of the quad-trocar ablation system has a respective electrode array 3510, 3512, 3514, and 3516 extending from the distal end of the trocar. The amount of extension of each electrode array is controlled by the position of the plunger 3522, 3524, 3526, and 3528 at the end of each device. As can be seen in FIG. 35, the electrodes in each array 3510-3516 do not form a complete circle, as is the case for the embodiment illustrated in FIG. 34A. For the example deployment of FIG. 35, the electrode arrays 3510-3516 are shown extended to approximately the same length relative to their trocars. As noted above, some electrode arrays can be extended to different lengths, such as fully extended or retracted, depending upon the application requirements. The size and shape of the ablation area can be effectively fine-tuned by selective extension of the independent electrode arrays. Thus, this example embodiment shows a particular amount of extension of the spiral electrodes for each single-trocar ablation device; however, the particular amount of extension shown is provided as an example only as the actual extent to which the spiral electrodes of each single-trocar ablation device are partially extended can vary among each ablation device of the ablation system as appropriate to the ablation procedure in which the ablation system is used as well as the desired ablation volume.

Figure 36:
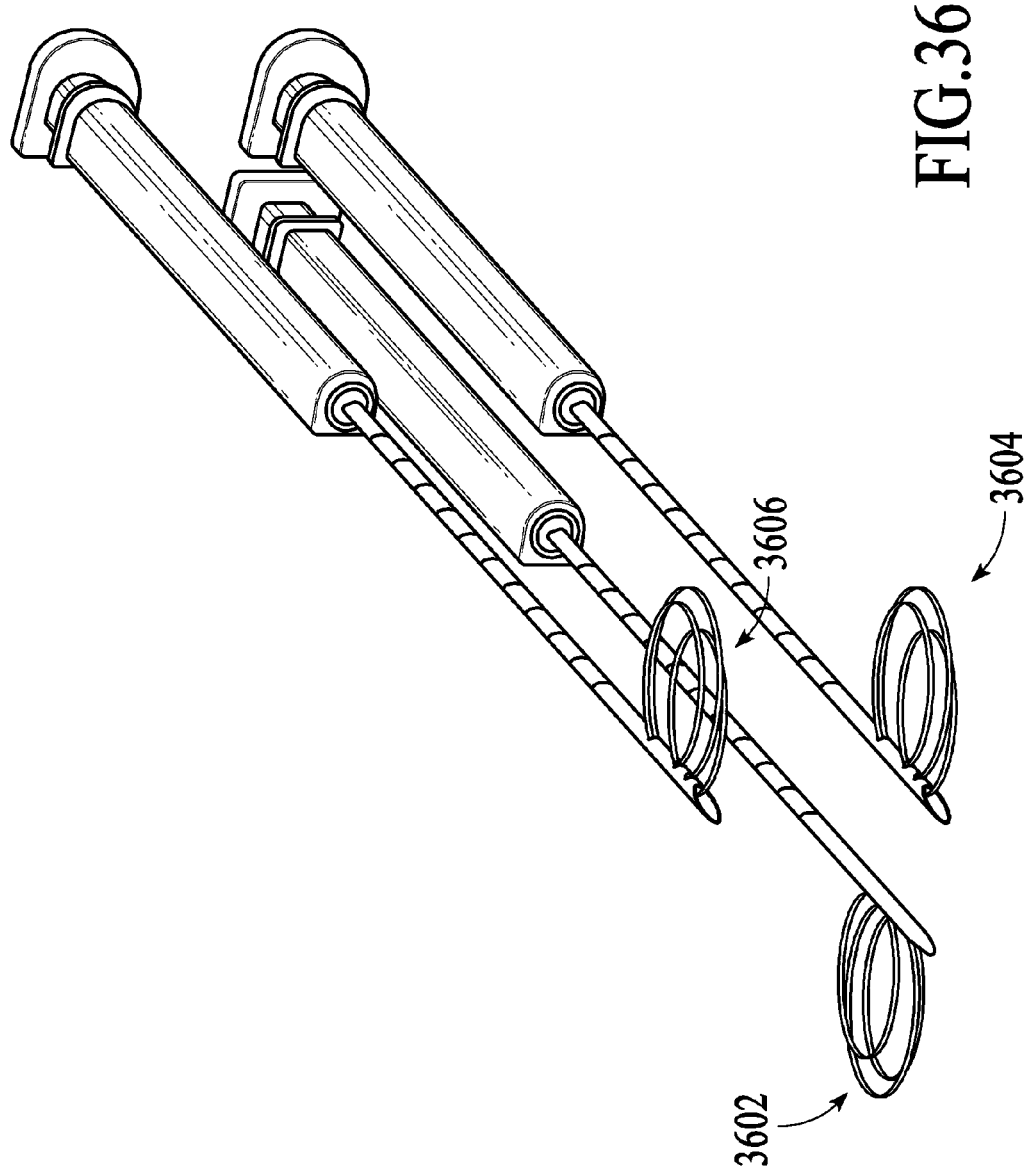
FIG. 36 shows a front perspective view of a tri-trocar ablation system formed from the simultaneous use of three single-trocar ablation devices, each single-trocar ablation device using one or more spiral electrodes in an array protruding fully or nearly fully from the distal end of the corresponding trocar, under an embodiment.

As stated above, a multi-trocar ablation system can be composed of any practical number of single-trocar devices. FIG. 36 shows a front perspective view of a tri-trocar ablation system formed from the simultaneous use of three single-trocar ablation devices, each single-trocar ablation device using one or more spiral electrodes in an array protruding fully or nearly fully from the distal end of the corresponding trocar, under an embodiment. The ablation system of FIG. 36A shows the use of three separate single-trocar devices. The orientation of a first plane formed by the first single-trocar ablation device electrode array 3602 relative to a second plane formed by the second single-trocar ablation device electrode array 3604 is such that the first and second planes intersect to collectively form a first ablation plane. The orientation of the third plane formed by the third single-trocar ablation device electrode array 3606 is such that the orientation of the first ablation plane relative to the third plane is parallel or nearly parallel.

The three single-trocar devices of the tri-trocar ablation device and be manipulated by three separate users, or they can be manipulated by two users, one of whom handles two of the devices simultaneously. These two devices can be utilized separately from one another or they can be coupled to each other through a bridge device, such as bridge 2010. The use of such a bridge, also allows a single user to manipulate all three devices of the tri-trocar ablation system.

Figure 37A:
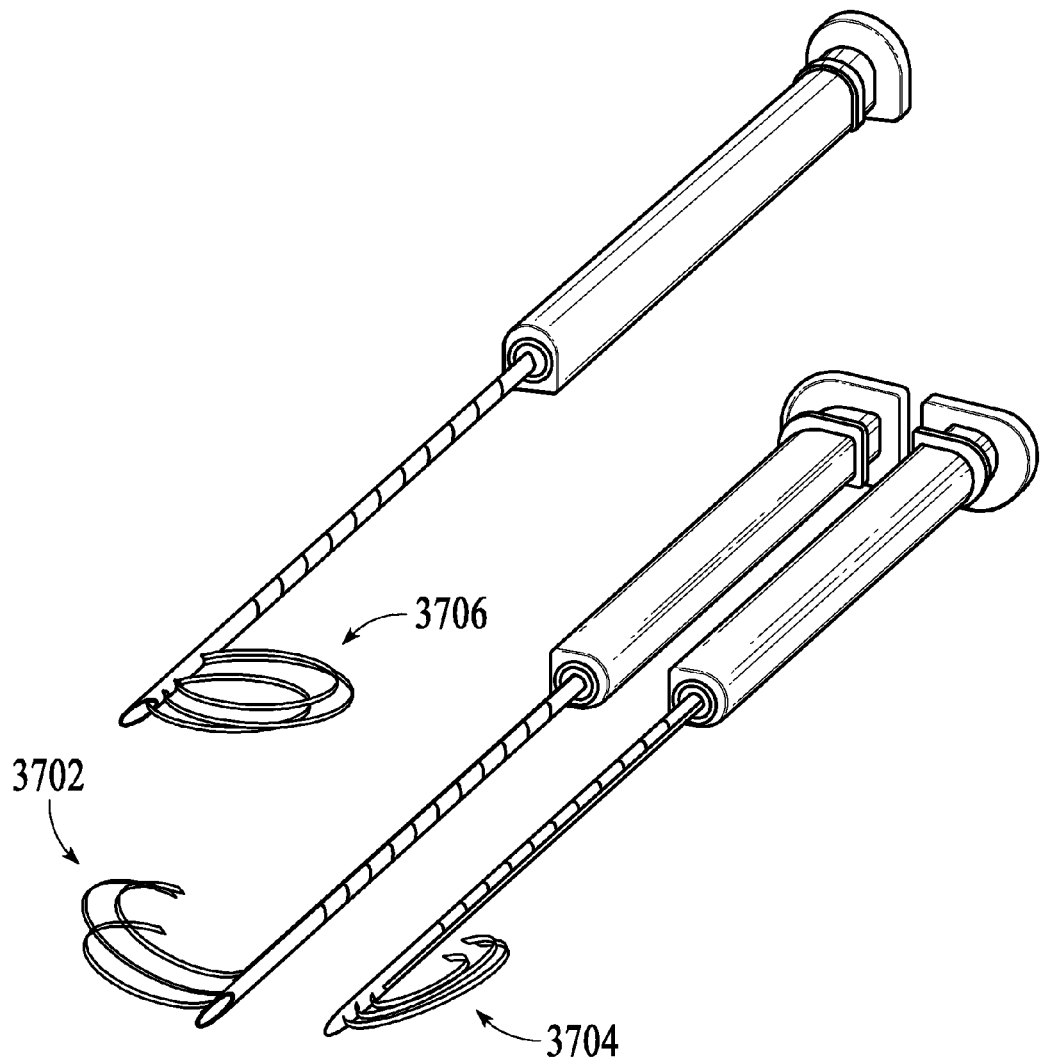
FIG. 37A shows a front perspective view of a tri-trocar ablation system formed from the simultaneous use of three single-trocar ablation devices, under an embodiment

The configuration, orientation, and relative placement of the separate trocar devices can be varied depending upon the requirements and constraints of the application. The electrode arrays can be angled relative to one another, or deployed to various degrees of extension to define and fine tune the ablation area. FIG. 37A shows a front perspective view of a tri-trocar ablation system formed from the simultaneous use of three single-trocar ablation devices, under an embodiment. For the example illustrated in FIG. 37A, one single-trocar ablation device uses one or more spiral electrodes in an array 3706 protruding fully or nearly fully from the distal end of the corresponding trocar, a second single-trocar ablation device uses one or more spiral electrodes in an array 3702 protruding partially from the distal end of the corresponding trocar, and a third single-trocar ablation device uses one or more spiral electrodes in an array 3704 protruding partially from the distal end of the corresponding trocar. This example embodiment shows a particular amount of extension of the spiral electrodes for two of the single-trocar ablation devices; however, the particular amount of extension shown is provided as an example only as the actual extent to which the spiral electrodes of each single-trocar ablation device are partially extended can vary among each ablation device of the ablation system as appropriate to the ablation procedure in which the ablation system is used as well as the desired ablation volume.

Figure 37B:
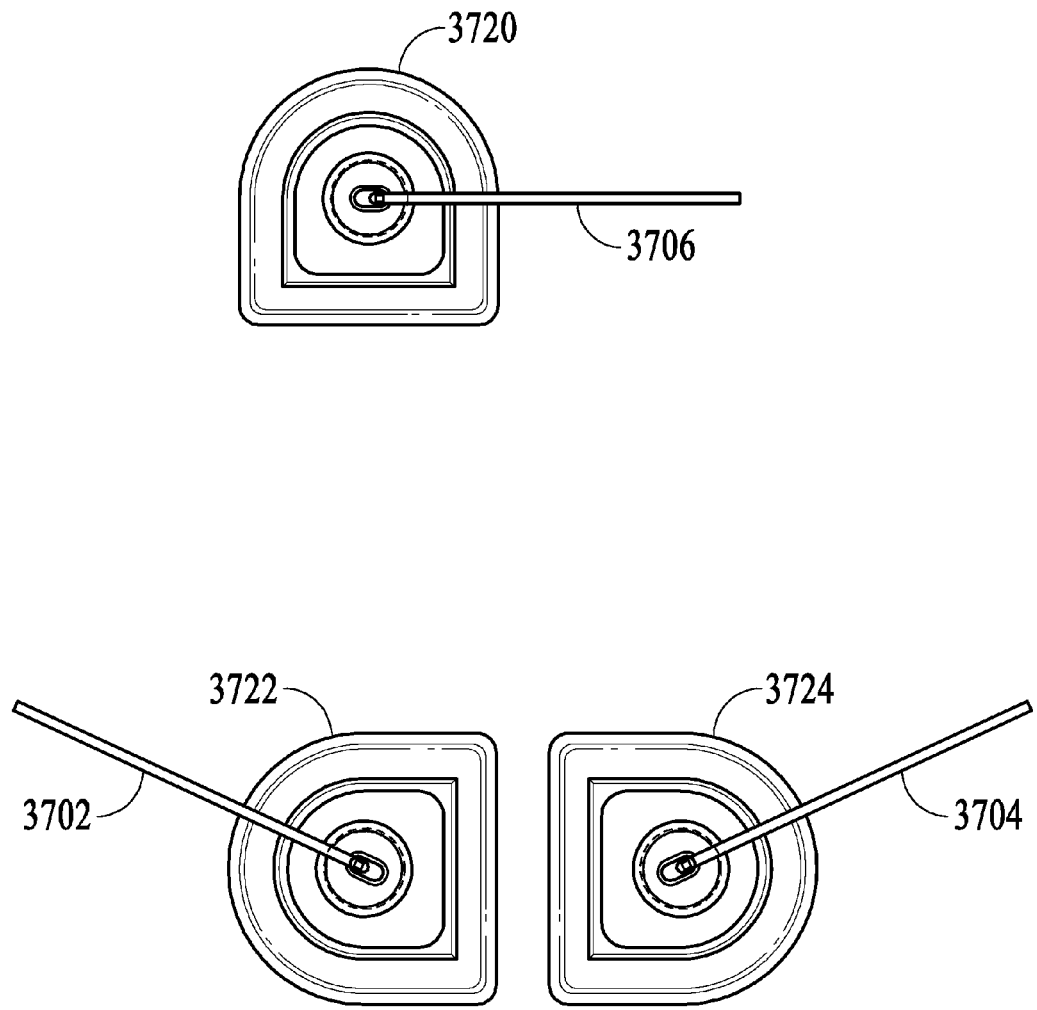
FIG. 37B shows a front view of the tri-trocar ablation system of FIG. 37A, under an embodiment.

For the embodiment of FIG. 37A, the orientation of a first plane formed by the first single-trocar ablation device electrode array 3702 relative to a second plane formed by the second single-trocar ablation device electrode array 3704 is such that the first and second planes intersect to collectively form a non-linear ablation surface. FIG. 37B shows a front view of the tri-trocar ablation system of FIG. 37A, under an embodiment. This view shows the first electrode array 3702 positioned at an angle relative to the second electrode array 3704, thus form a non-linear ablation surface. The third electrode array 3706 is positioned relative to arrays 3702 and 3704 to create the ablation volume of a specific shape and size. FIG. 37C shows a rear view of the tri-trocar ablation system of FIG. 37A. This view shows the system from the perspective of the user. Each of the electrode arrays can be deployed to any extended length through appropriate manipulation of the deployment plungers 3720, 3722, and 3724. For example, one single-trocar ablation device can use one or more spiral electrodes in an array protruding fully or nearly fully from the distal end of the corresponding trocar, and two single-trocar ablation devices can use one or more spiral electrodes in an array protruding partially from the distal end of the corresponding trocar. The particular amount of extension depends upon the specific requirements and constraints of the ablation procedure in which the ablation system is used as well as the desired ablation volume. For the embodiment of FIGS. 37A-C, the orientation of a first plane formed by the first single-trocar ablation device electrodes relative to a second plane formed by the second single-trocar ablation device electrodes is such that the first and second planes intersect to collectively form a non-linear ablation surface.

Figure 38:
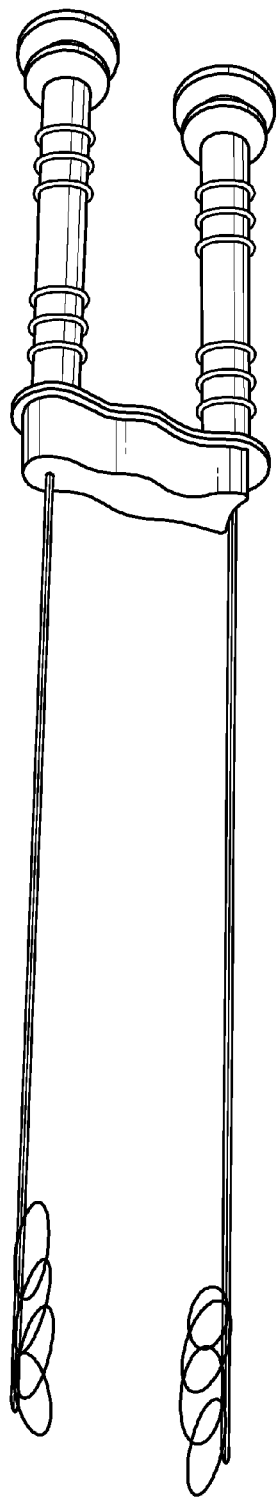
FIG. 38 shows deployment of a multi-trocar ablation system comprising independent single-trocar devices in the region of target tissue, under an embodiment.
Figure 39:
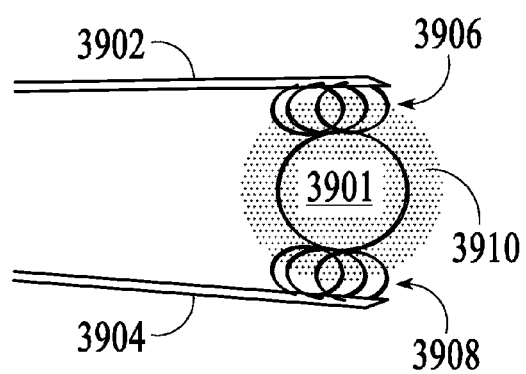
FIG. 39 illustrates an ablation area formed by the multi-trocar ablation system of FIG. 38, under an embodiment.

The use of multiple independent single-trocar devices generally enables accurate electrode placement with in a patient or subject with appropriate safety margins. The size, shape, and volume of the ablation area can be precisely controlled directly by the user through manipulation of the devices. FIG. 38 shows deployment of a multi-trocar ablation system comprising independent single-trocar devices in the region of target tissue, under an embodiment configuration information of a dual-trocar ablation system that uses one or more spiral electrodes in an array protruding fully or nearly fully from the distal end of each trocar, under an embodiment. For the example application of FIG. 39, single-trocar devices 3902 and 3904 are deployed around target tissue 3901. Upon the application of power, an ablation area 3910 in the proximity of electrode arrays 3906 and 3908 is produced. The relative position of the devices 3902 and 3904 can be altered to control the size and shape of ablation area 3910 to ensure that the target tissue 3901 is fully ablated. The use of planar electrodes, such as 3906 and 3908 produces a comprehensive and controllable ablation area that prevents the need for direct contact of the electrodes with the target tissue (e.g., tumor or lesion) 3901.

The planar electrode ablation devices, and multi-trocar ablation systems described herein transmit energy within a clearly visible space for the creation of consistent and predictable ablation volumes. The use of separate single-trocar devices in a multi-trocar system allows one or more users to manipulate a plurality of ablation devices. This provides maximum flexibility with regard to device placement and allows the users to reach target tissue that might otherwise be obstructed by structural anatomic elements (e.g., bones) or critical tissue areas (e.g., blood vessels). It also allows accommodation of irregular (e.g., non-spherical) lesions or other targets.

Depending upon the actual utilization requirements, which clearly can vary from operation to operation, devices of many different configurations can be provided. The Figures provided herein are intended to provide an example of different variations, and it is to be understood that the described embodiments are intended to cover many other possible variations. These variations include differences in device dimensions, such as trocar length, handle length, deployed electrode length, electrode width, bridge width, and so on. FIG. 40 is a table of dimensions corresponding to the tissue ablation system, under various embodiments described herein.

The embodiments shown above (e.g., FIGS. 20-39) show the use of specific numbers of independent or separate single-trocar ablation devices used in combination to form an ablation system. However, alternative embodiments can use any other number of single-trocar ablation devices simultaneously in any number of configurations to form a variety of additional ablation systems for target tissue volumes of different sizes and/or shapes.

The tissue ablation devices of an embodiment include a device comprising a trocar. The device of an embodiment includes a plurality of electrodes positioned in the trocar. Each electrode of an embodiment is a wire electrode. Each electrode of an embodiment is configured to form a planar electrode when moved from a retracted state in the trocar to a deployed state. A configuration of the plurality of electrodes of an embodiment in the deployed state is an organized grouping of planar geometries encompassing a geometrically shaped tissue volume.

The tissue ablation devices of an embodiment include a trocar and a plurality of electrodes positioned in the trocar. Each electrode of the plurality of electrodes is a wire electrode. For example, each electrode can be a flat wire electrode. Each electrode is configured to form a planar electrode when moved from a retracted state in the trocar to a deployed state. A configuration of the plurality of electrodes in the deployed state defines a planar geometry encompassing a desired geometrically shaped tissue volume. The planar geometry of the deployed electrodes maximizes the effective electrode surface area and thereby increases the capacity of a fusible tissue link.

The tissue ablation devices described herein are configured to increase the amount of energy that can be delivered to target tissue. The increase in delivered energy is realized by increasing the capacity of a fusible tissue link by lowering the energy density in the coupled tissue via an increase of the effective surface area of an energy delivery device (the tissue ablation devices), as described in detail below. The amount of time required to create an ablation, the ability to create large ablations, and the ability to overcome the thermal heat-sink created by things such a blood flow in vessels is directly proportional to the level at which energy can be delivered to the tissue. Therefore, use of the tissue ablation devices of an embodiment result in reduced ablation times and provide well-defined ablation volumes.

During ablative procedures, the tissue ablation device of an embodiment, by virtue of the planar electrode array, interfaces with the target tissue so the tissue becomes a part of the thermal and electrical conduction path, and this thermal and electrical conductive tissue path acts as a "fusible tissue link." The fusible tissue link is severed when tissue vaporization or char occurs. The capacity or energy rating of this fusible tissue link is directly proportional to the amount of tissue area electrically coupled to the delivery device. Increasing the amount of tissue area electrically coupled to the device increases the capacity or energy rating of this fusible tissue link.

Delivery of high levels of energy to tissue in order to quickly achieve ablations, large ablations, and ablations near heat-sinks is counter to the fusible tissue link effect of tissue treated by conventional ablation devices. When the amount of energy delivered to the tissue is extremely high, a portion of the tissue will be vaporized leaving behind charred tissue which is a poor electrical and thermal conductor. When a lower, but still excessive amount of energy is delivered to the coupled tissue, the coupled tissue energy density exceeds the tissue's capacity resulting in tissue charring. This charring inhibits the thermal and electrical conduction.

The tissue ablation devices described herein, in contrast to conventional devices, increase the capacity or energy rating of the fusible tissue link by increasing the amount of conductive surface area of the energy delivery device (e.g., a radio frequency antenna, microwave antenna, electroporation, etc.) while maintaining a sufficient but not excessive amount of electrode separation to create a larger effective surface area. The increase in the surface area of the energy delivery device is achieved in an embodiment by increasing the surface area of a single antenna or a series of antennas. If multiple antennas are used they are separated in such a way that their coupling with the tissue, or the effective surface area, does not create an excessive energy density in the coupled tissue, as described herein. This spacing is typically several millimeters as measured between the antenna surfaces, but is not so limited and is dependent on one or more other factors (e.g. size of antenna elements, configuration of antenna elements, type of target tissue, etc.).

The tissue ablation devices described herein are configured to provide a relatively large delivery surface area to be interfaced with biologic tissue in order to maximize the amount of effective surface area while at the same time creating sufficient electrode separation, thereby increasing the amount of energy which can be effectively transferred to the tissue. The device configurations herein therefore reduce the amount of time required to ablate, coagulate, or desiccate the target tissue by providing devices having antenna configurations that provide energy transfer capability that better approximates or nearly approximates the energy transfer capability of the target tissue itself across a larger volume or surface area.

The tissue ablation devices described herein maximize the effective surface area by using a series of rectangular or flat wires in a planar nested configuration. This allows the antennas to occupy a minimum amount of space prior to deployment into the tissue in order to minimize the trauma during delivery of the device to the target area (prior to deployment of the antennas). The nested series of antennas maximizes the amount of effective surface area and thereby increases the amount of energy which can be passed to the tissue to minimize or eliminate prematurely desiccating or charring the tissue adjacent or near the antennas. The series of planer antennas enable the coagulation or ablation of various geometric volumes of tissue including spherical volumes.

The configuration of the tissue ablation devices described herein also minimize the decrease in energy density as the energy passes through the target tissue or in some areas or cases to maintain or increase the energy density as it passes through the target tissue (e.g. energy emitted from an antenna located on the surface of a sphere some or all of which then flows towards a more central location within the sphere where the volume of tissue is reduced thereby creating a relative increase in the energy density). This is in contrast to other systems in which the highest point of energy density is immediately adjacent to an electrode or just beyond the electrode (such as when saline is used in an attempt to create a virtual electrode) and then decreases rapidly as the energy move through an increasing volume of target tissue and away from a source electrode.

Experimental test results were obtained for the tissue ablation devices of an embodiment. With reference to the devices described above (FIGS. 26-36B), the experimental results were obtained using a sample size of six (6) devices for each product configuration (3 cm device, 3.5 cm device, 4 cm device, 5 cm device, 7 cm device). The devices functioned through six cycles each without tissue penetration, temperature or mechanical issues in ex-planted beef liver. For each device, six (6) application cycles were completed, for a total of 36 applications/lesions. This sample size was determined to be sufficient to indicate possible variations and functionality upon repeated device testing and device to device variability. Each test cycle can be considered to be an independent data point with respect to the resultant lesion size developed in ex-planted beef liver tissue.

Clinical results were also obtained in fourteen (14) patients in a prospective study. In this study, patients scheduled for resection of their liver tumors underwent tumor ablation using the devices described herein, followed by the planned resection. Following the liver resection the ablated tissue was bread loafed and the ablation size was noted. The total ablation time was also recorded. Three different size ablations were attempted, including a 3.5 cm diameter, a 5 cm diameter, and a 7 cm diameter ablation. Patient and procedure details for this study included gender, age, tumor type, the use of any inflow venous occlusion, and operative or postoperative complications. There was no significant difference within the demographics between patients.

Results of the experimental tests and clinical study showed that, across the devices, the amount of time required to achieve the target ablation sizes was significantly reduced as compared to conventional radio frequency ablation devices. For example, a three-minute application of power approximately in the range of 60 to 80 watts via the devices described above resulted in an ablation size of approximately 3.6 cm (average value). Furthermore, results showed that, across the devices, a five-minute application of power approximately in the range of 100 to 135 watts resulted in an ablation size of approximately 5.1 cm (average value). Results also showed that, across the devices, a twelve-minute application of power approximately in the range of 135 to 150 watts resulted in an ablation size of approximately 7.0 cm (average value).

The tissue ablation systems described herein are unique in both their speed and ability to use a variety of existing radio frequency ablation generators available in many hospitals around the world as the energy source. For example, the devices described herein can be used with generators such as the Radio Therapeutics Corporation—Boston Scientific Generator (Models RF 2000® or RF 3000®), Celon LabPower (Celon-Olympus, Teltow-Berlin Germany), the Radionics® (Tyco Healthcare) Cool-tip™ RF Generator, and the RITA® System RF Generator (Model 1500 or 1500x) (Rita Medical Systems, Fremont, Calif.). Referring to the results of the experimental tests and clinical study described above, use of different generators as the power source did not have a significant effect on the results. Other than small variations in their operation, there was little difference noted between the different generators.

A specific example of the tissue ablation system described herein includes the InCircle™ Bi-Polar Radio Frequency Ablation Device (InCircle) available from RFA Medical, Inc., Fremont, Calif. The InCircle is a sterile bi-polar tissue ablation device comprising a cable, spacing block, two handles, and a series of deployable electrodes. The electrodes create a spherical ablation of tissue as described herein. The InCircle functions or operates to ablate soft tissue during percutaneous, laparoscopic or intraoperative surgical procedures. The InCircle is provided as an example of the devices described herein and is not intended to limit the devices described herein to the configuration of the InCircle. The following procedures or algorithm(s) are provided as guides or examples only, and treatment parameters may be modified according to user experience and the thermal requirements of individual tissue types.

An operator of the InCircle, when using the device in a medical procedure, begins by determining an appropriate ablation location in the target tissue. The operator, using sterile techniques, removes the InCircle from the package and verifies the free movement of all electrodes and ensures the device has not been damaged. All electrodes are then retracted and the device is placed or configured so that all electrodes are properly positioned for deployment into the target tissue. The operator positions and deploys the electrodes to the desired depth/location within the target tissue using techniques appropriate to the procedure, and verifies the correct electrode positions prior to the application of energy.

The cable of the InCircle is connected to the device and the RF generator using a cable adaptor appropriate to the generator, and the cable connections are checked to ensure they are firmly and properly seated prior to use. The RF generator is setup according to the manufacturer's instructions for the particular generator. Grounding or return pads are not required because the InCircle is a bi-polar device.

As described above, the device of an embodiment can be used with numerous energy generators. Thus, the InCircle operates using any number of generators, for example, the Radio Therapeutics Corporation—Boston Scientific Generator (Models RF 2000® or RF 3000®), the Radionics® (Tyco Healthcare) Cool-tip™ RF Generator, and the RITA® System RF Generator (Model 1500 or 1500x) to name a few.

When using the InCircle with the Radio Therapeutics Corporation—Boston Scientific Generator (Models RF 2000® or RF 3000®), after following the manufacturer's instructions for setup of the generator, the generator timer is set for the ablation size desired (e.g., 3.5 cm ablation size desired, time set to approximately 3 minutes, power set to approximately 60-80 watts; 5 cm ablation size desired, time set to approximately 5 minutes, power set to approximately 100-135 watts; 7 cm ablation size desired, time set to approximately 12 minutes, power set to approximately 140-150 watts). The application of RF energy is started by activating the generator and, based on the ablation size desired, the power is set using the settings described above. At the end of the programmed time, the electrodes are fully retracted and the device is removed. This process can be repeated for additional ablations as desired; the electrodes are cleaned as necessary between deployments by rinsing the electrodes in sterile water or by gently wiping them to remove excess tissue. If desired, the InCircle trocar tracks can be ablated by applying approximately 50 Watts of RF energy while the device is slowly removed from the tissue.

When using the Radionics® (Tyco Healthcare) Cool-tip RF™ Generator, after following the manufacturer's instructions for setup of the generator, the generator control mode is set to manual. The generator timer and power are set for the ablation size desired (e.g., 3.5 cm ablation size desired, time set to approximately 3 minutes, power set to approximately 60-80 watts; 5 cm ablation size desired, time set to approximately 5 minutes, power set to approximately 100-135 watts; 7 cm ablation size desired, time set to approximately 12 minutes, power set to approximately 140-150 watts). The application of RF energy is started by activating the generator. At the end of the programmed time, the electrodes are fully retracted and the device is removed. This process can be repeated for additional ablations as desired; the electrodes are cleaned as necessary between deployments by rinsing the electrodes in sterile water or by gently wiping them to remove excess tissue. If desired, the InCircle trocar tracks can be ablated by applying approximately 50 Watts of RF energy while the device is slowly removed from the tissue.

When using the RITA® System RF Generator (Model 1500 or 1500x), after following the manufacturer's instructions for setup of the generator, the generator control mode is set to "P" for power mode. The generator timer and power are set for the ablation size desired (e.g., 3.5 cm ablation size desired, time set to approximately 3 minutes, power set to approximately 60-80 watts; 5 cm ablation size desired, time set to approximately 5 minutes, power set to approximately 100-135 watts; 7 cm ablation size desired, time set to approximately 12 minutes, power set to approximately 140-150 watts). The application of RF energy is started by activating the generator. At the end of the programmed time, the electrodes are fully retracted and the device is removed. This process can be repeated for additional ablations as desired; the electrodes are cleaned as necessary between deployments by rinsing the electrodes in sterile water or by gently wiping them to remove excess tissue. If desired, the InCircle trocar tracks can be ablated by applying approximately 50 Watts of RF energy while the device is slowly removed from the tissue.

As with any RF medical device, the use of this device results in localized elevated temperatures that can cause thermal injury to the skin. In addition, tissue or organs adjacent to the tissue being ablated may be injured thermally if precautions are not taken as appropriate to the procedure. To minimize the potential for thermal injury to the skin or adjacent tissues, temperature-modifying measures can be initiated at the physician's discretion. These may include applying a sterile ice pack or saline-moistened gauze to cool and/or separate tissues. Patient and procedure selection is the responsibility of the medical professional and the outcome is dependent on many variables, including patient anatomy, pathology, and surgical techniques.

As described above, the tissue ablation system of an embodiment delivers energy to target tissue via the energy conduits or electrodes. The energy includes, for example, radio frequency (RF) energy, but is not so limited. For example, other types of energy can include microwave energy. The energy is delivered via any of a number of techniques. The energy can be applied via pulsed waveforms and/or continuous waveforms, but is not so limited.

In an example procedure that includes use of the tissue ablation system, energy can be applied to energy conduits during deployment of the energy conduits into the target tissue. The energy can be applied automatically or, alternatively, manually as a procedure progresses and as appropriate to the procedure. Also, the energy delivered to the target tissue can be adjusted during the procedure by adjusting any of the power level, the waveforms, and a combination of the power level and the waveform.

In another example procedure that includes use of the tissue ablation system, energy can be applied to energy conduits following deployment of the energy conduits into the target tissue. The energy can be applied automatically or, alternatively, manually as appropriate to the procedure. Also, the energy delivered to the target tissue can be adjusted manually and/or automatically during the procedure by adjusting any of the power level, the waveforms, and a combination of the power level and the waveform.

As described above, the application of power to the target tissue under an embodiment is controlled automatically and/or manually under a number of procedures. A first type of procedure uses a predetermined pattern of energy delivery according to a time schedule. A second type of procedure varies the application of energy to the target tissue volume in accordance with temperature information or feedback parameters of the tissue. A third type of procedure varies the application of energy to the target tissue volume in accordance with impedance information or feedback parameters of the tissue in combination with elapsed time. A fourth type of procedure varies the application of energy to the target tissue volume in accordance with impedance information or feedback parameters of the tissue. A fifth type of procedure varies the application of energy to the target tissue volume in accordance with temperature and impedance information or feedback parameters of the tissue.

It should be noted that patient and procedure selection is the responsibility of the medical professional/user and the outcome is dependent on many variables, including patient anatomy, pathology, and surgical techniques. Use of the tissue ablation device, system and methods described herein for tissue ablation can result in localized elevated temperatures that can cause thermal injury to the skin. In addition, tissue or organs adjacent to the tissue being ablated may be injured thermally. To minimize the potential for thermal injury to the skin or adjacent tissues, temperature-modifying measures can be initiated at the physician's discretion. These may include applying a sterile ice pack or saline-moistened gauze to cool and/or separate tissues, but are not so limited. The purpose of tissue ablation may be to destroy tissue within and around malignant tissue, such as tumors with cancer-causing cells.

Tissue ablation systems of an embodiment described above include a tissue ablation device, comprising: a trocar including a distal end and a lumen extending along a longitudinal axis of the trocar, wherein the trocar includes a plurality of orifices positioned along the longitudinal axis; and an electrode array comprising a plurality of electrodes, wherein the plurality of electrodes is positioned in the lumen in a retracted state, wherein the plurality of electrodes is deployed to a deployed state through a set of orifices of the plurality of orifices, wherein each electrode of the plurality of electrodes has at least one radius of curvature in the deployed state so that the electrode array forms a series of shaped electrodes in the deployed state.

The at least one radius of curvature of an embodiment is proportional to a size of an ablation volume generated with the electrode array in the deployed state.

The at least one radius of curvature of an embodiment is determinative of a shape of an ablation volume generated with the electrode array in the deployed state.

Each electrode of the plurality of electrodes of an embodiment in the deployed state has an effective surface area proportional to the at least one radius of curvature.

The electrode array of an embodiment in the deployed state forms a planar series of shaped electrodes.

The electrode array of an embodiment in the deployed state forms a linear series of shaped electrodes aligned along the longitudinal axis.

A shape of the shaped electrodes of an embodiment is an ellipse.

A shape of the shaped electrodes of an embodiment is a circle.

A shape of the shaped electrodes of an embodiment is a semicircle.

The distal end of the trocar of an embodiment includes a sharp region for piercing tissue.

A distal tip of each electrode of the plurality of electrodes of an embodiment includes a sharp region for penetrating tissue.

Distal tips of each of the plurality of electrodes of an embodiment, when transitioning from the retracted state to the deployed state, transition through approximately all points in a plane at a distance from a fixed center reference point, wherein the distance is the at least one radius of curvature.

Distal tips of each of the plurality of electrodes of an embodiment, when transitioning from the retracted state to the deployed state, transition through a majority of points in a plane at a distance from a fixed center reference point, wherein the distance is the at least one radius of curvature.

Distal tips of each of the plurality of electrodes of an embodiment, when transitioning from the retracted state to the deployed state, transition through approximately all points in a plane such that a sum of distances to a first fixed point and a second fixed point of the points is a constant.

Distal tips of each of the plurality of electrodes of an embodiment, when transitioning from the retracted state to the deployed state, transition through a majority of points in a plane such that a sum of distances to a first fixed point and a second fixed point of the points is a constant.

The plurality of electrodes of an embodiment is deployed to a partially deployed state.

Distal tips of each of the plurality of electrodes of an embodiment, when transitioning from the retracted state to the partially deployed state, transition through a portion of points in a plane at a distance from a fixed center reference point, wherein the distance is the at least one radius of curvature.

Distal tips of each of the plurality of electrodes of an embodiment, when transitioning from the retracted state to the partially deployed state, transition through a portion of points in a plane such that a sum of distances to a first fixed point and a second fixed point of the portion of points is a constant.

The plurality of electrodes of an embodiment includes two electrodes.

A first center of a first shape formed by a first electrode of an embodiment is offset from a second center of a second shape formed by a second electrode.

The first shape of an embodiment is a first ellipse having a first radius of curvature and the second shape is a second ellipse having a second radius of curvature.

The first radius of curvature of an embodiment is different than the second radius of curvature.

The first radius of curvature of an embodiment is approximately equivalent to the second radius of curvature.

The plurality of electrodes of an embodiment includes three electrodes.

A first center of a first shape formed by a first electrode of an embodiment is offset from one or more of a second center of a second shape formed by a second electrode and a third center of a third shape formed by a third electrode.

The first shape of an embodiment is a first ellipse having a first radius of curvature, the second shape is a second ellipse having a second radius of curvature, and the third shape is a third ellipse having a third radius of curvature. The first radius of curvature of an embodiment is different than one or more of the second radius of curvature and the third radius of curvature. The first radius of curvature of an embodiment is approximately equivalent to one or more of the second radius of curvature and the third radius of curvature.

The plurality of electrodes of an embodiment includes four electrodes.

A first center of a first shape formed by a first electrode of an embodiment is offset from one or more of a second center of a second shape formed by a second electrode, a third center of a third shape formed by a third electrode, and a fourth center of a fourth shape formed by a fourth electrode.

The first shape of an embodiment is a first ellipse having a first radius of curvature, the second shape is a second ellipse having a second radius of curvature, the third shape is a third ellipse having a third radius of curvature, and the fourth shape is a fourth ellipse having a fourth radius of curvature.

The first radius of curvature of an embodiment is different than one or more of the second radius of curvature, the third radius of curvature, and the fourth radius of curvature.

The first radius of curvature of an embodiment is approximately equivalent to one or more of the second radius of curvature, the third radius of curvature, and the fourth radius of curvature.

Each electrode of the plurality of electrodes of an embodiment has a first polarity.

A first set of electrodes of the plurality of electrodes of an embodiment has a first polarity and a second set of electrodes of the plurality of electrodes has a second polarity.

The plurality of electrodes of an embodiment is deployed laterally through the plurality of orifices to the deployed state.

The plurality of electrodes of an embodiment comprise flat wire electrodes.

At least one electrode of the plurality of electrodes of an embodiment comprises one or more of a flat wire electrode, a round wire electrode, a flat tube electrode, and a round tube electrode.

Each orifice of the plurality of lateral orifices of an embodiment is longitudinally aligned with each other orifice along the longitudinal axis.

An electrode of the plurality of electrodes of an embodiment includes an electrode lumen.

The device of an embodiment comprises a handle assembly coupled to the trocar and the electrode array.

The electrode array, when positioned in proximity to target tissue, defines an outer surface of an ablation volume.

The device of an embodiment comprises an electromagnetic energy source and at least one cable, the at least one cable coupling the electrode array to the electromagnetic energy source.

The plurality of electrodes of an embodiment comprises a number of electrodes appropriate to create an ablation volume in target tissue without impeding out the electrode array when electromagnetic energy is delivered to the electrode array from the electromagnetic energy source.

The electrode array of an embodiment, when positioned in proximity to the target tissue, defines an outer surface of the ablation volume and at least partially encircles the ablation volume.

When electromagnetic energy is delivered to the electrode array of an embodiment, the electrode array ablates the target tissue starting from the outer surface and progressing toward an inner portion of the target tissue.

The device of an embodiment comprises at least one additional lumen extending along the longitudinal axis.

Tissue ablation systems of an embodiment described above include a tissue ablation device, comprising: a trocar including a distal end, a lumen extending along a longitudinal axis of the trocar, and a plurality of orifices positioned along the longitudinal axis; and an electrode array comprising a plurality of electrodes, wherein the plurality of electrodes is positioned in the lumen in a retracted state, wherein the plurality of electrodes is deployed to a deployed state through a set of the plurality of orifices, wherein each electrode of the plurality of electrodes has at least one radius of curvature in the deployed state so that the electrode array forms a series of shaped electrodes in the deployed state.

Tissue ablation systems of an embodiment described above includes a tissue ablation device, comprising: a trocar including a distal end and a lumen extending along a longitudinal axis of the trocar, wherein the distal end includes a sharp region for piercing tissue, wherein the trocar includes a plurality of orifices positioned along the longitudinal axis; an electrode array comprising a plurality of electrodes, wherein the plurality of electrodes have a retracted state and a deployed state, wherein each electrode of the plurality of electrodes is contained in the lumen in the retracted state, wherein one or more electrode is deployed through an orifice of the plurality of orifices, wherein each electrode has a radius of curvature in the deployed state, wherein the electrode array forms a planar series of elliptical electrodes in the deployed state.

Tissue ablation systems of an embodiment described above includes a tissue ablation device, comprising: a trocar including a distal end and a lumen extending along a longitudinal axis of the trocar, wherein the trocar includes a plurality of orifices aligned along the longitudinal axis; an electrode array comprising a plurality of electrodes, wherein the plurality of electrodes are deployed from the lumen via the plurality of orifices, wherein each electrode of the plurality of electrodes has at least one radius of curvature in a deployed state, wherein the electrode array in the deployed state forms a series of elliptical electrodes aligned along the longitudinal axis.

Tissue ablation systems of an embodiment described above includes a system, comprising: an ablation device comprising a trocar and an electrode array, wherein the trocar includes a distal end and a lumen extending along a longitudinal axis of the trocar, wherein the trocar includes a plurality of orifices positioned along the longitudinal axis, wherein the electrode array comprises a plurality of electrodes, wherein the plurality of electrodes is positioned in the lumen in a retracted state, wherein the plurality of electrodes is deployed to a deployed state through a set of the plurality of orifices, wherein each electrode of the plurality of electrodes has at least one radius of curvature in the deployed state so that the electrode array forms a series of shaped electrodes in the deployed state; an electromagnetic energy source; and at least one cable coupling the ablation device to the electromagnetic energy source.

Tissue ablation systems of an embodiment described above include a tissue ablation device, comprising: a trocar including a distal end, a lumen extending along a longitudinal axis of the trocar, and a plurality of orifice sets in communication with the lumen; and an electrode array comprising a plurality of electrode sets, wherein electrode sets of the plurality of electrode sets include a plurality of electrodes, wherein the plurality of electrode sets is deployed to a deployed state through the plurality of orifice sets, wherein electrodes of the plurality of electrodes have at least one radius of curvature in the deployed state so that the electrode array in the deployed state forms at least one set of shaped electrodes.

Tissue ablation systems of an embodiment described above include a tissue ablation device, comprising: a trocar including a distal end and a lumen extending along a longitudinal axis of the trocar, wherein the trocar includes a plurality of orifice sets in communication with the lumen, wherein each orifice set of the plurality of orifice sets includes a plurality of orifices positioned along the longitudinal axis; and an electrode array comprising a plurality of electrode sets, wherein each electrode set of the plurality of electrode sets includes a plurality of electrodes, wherein the plurality of electrode sets is deployed to a deployed state through the plurality of orifice sets, wherein each electrode of the plurality of electrodes has at least one radius of curvature in the deployed state so that the electrode array forms at least one set of shaped electrodes in the deployed state.

Tissue ablation systems of an embodiment described above include a tissue ablation device, comprising: a trocar including a distal end, a lumen extending along a longitudinal axis of the trocar, and a plurality of orifice sets positioned along the longitudinal axis, wherein the distal end includes a sharp region for piercing tissue; an electrode array comprising a plurality of electrode sets, wherein electrode sets of the plurality of electrode sets include a plurality of electrodes, wherein the plurality of electrodes in a retracted state is contained in the lumen and deployed to a deployed state through the plurality of orifice sets, wherein electrodes of the plurality of electrodes have at least one radius of curvature in the deployed state, wherein the electrode array forms at least one set of planar elliptical electrodes in the deployed state.

Tissue ablation systems of an embodiment described above include a tissue ablation device, comprising: a trocar including a distal end and a lumen extending along a longitudinal axis of the trocar, wherein the trocar includes a plurality of orifices aligned along the longitudinal axis; an electrode array comprising a plurality of electrode sets having a plurality of electrodes, wherein the plurality of electrodes are deployed from the lumen via the plurality of orifices, wherein electrodes of the plurality of electrodes has at least one radius of curvature in a deployed state, wherein the electrode array in the deployed state forms a plurality of sets of elliptical electrodes aligned along the longitudinal axis.

Tissue ablation systems of an embodiment described above include a tissue ablation system, comprising: an ablation device comprising a trocar and an electrode array, wherein the trocar includes a distal end, a lumen extending along a longitudinal axis, and a plurality of orifice sets in communication with the lumen, wherein the electrode array comprises a plurality of electrode sets, wherein electrode sets each include a plurality of electrodes, wherein the plurality of electrode sets is deployed to a deployed state through the plurality of orifice sets, wherein electrodes of the plurality of electrodes have at least one radius of curvature in the deployed state so that the electrode array in the deployed state forms at least one set of shaped electrodes; an electromagnetic energy source; and at least one cable coupling the ablation device to the electromagnetic energy source.

Tissue ablation systems of an embodiment described above include a tissue ablation system comprising: a plurality of ablation devices that each includes a trocar and an electrode array, wherein the trocar includes a plurality of orifices, wherein the electrode array comprises a plurality of electrodes, wherein the plurality of electrodes is deployed to a deployed state through the plurality of orifices, wherein each electrode of the plurality of electrodes has at least one radius of curvature in the deployed state so that the electrode array forms a linear series of shaped electrodes in the deployed state; and a bridge comprising a plurality of receptacles that receive the plurality of ablation devices, wherein the bridge holds an ablation device in a fixed position relative to at least one other ablation device of the plurality of ablation devices.

Tissue ablation systems of an embodiment described above include a tissue ablation system comprising: a plurality of ablation devices that each includes a trocar and an electrode array, wherein the trocar includes a plurality of orifices, wherein the electrode array comprises a plurality of electrodes, wherein the plurality of electrodes is deployed to a deployed state through the plurality of orifices, wherein each electrode of the plurality of electrodes has at least one radius of curvature in the deployed state so that the electrode array forms a linear series of shaped electrodes in the deployed state; a bridge comprising a plurality of receptacles that receive the plurality of ablation devices, wherein the bridge holds an ablation device in a fixed position relative to at least one other ablation device of the plurality of ablation devices; an electromagnetic energy source; and at least one cable coupling the plurality of ablation devices to the electromagnetic energy source.

Tissue ablation systems of an embodiment described above include a tissue ablation system comprising a plurality of ablation devices that each includes a trocar and an electrode array, wherein the trocar includes a plurality of orifices, wherein the electrode array comprises a plurality of electrodes, wherein the plurality of electrodes is deployed to a deployed state through the plurality of orifices, wherein each electrode of the plurality of electrodes has at least one radius of curvature in the deployed state so that the electrode array forms a linear series of shaped electrodes in the deployed state.

The system of an embodiment comprises a bridge comprising a plurality of receptacles that receive the plurality of ablation devices, wherein the bridge holds an ablation device in a fixed position relative to at least one other ablation device of the plurality of ablation devices.

Tissue ablation systems of an embodiment described above include a tissue ablation system comprising: a plurality of ablation devices that each includes a trocar and an electrode array, wherein the trocar includes a plurality of orifice sets, wherein the electrode array comprises a plurality of electrode sets, wherein electrode sets of the plurality of electrode sets include a plurality of electrodes, wherein the plurality of electrode sets is deployed to a deployed state through the plurality of orifice sets, wherein electrodes of the plurality of electrodes have at least one radius of curvature in the deployed state so that the electrode array in the deployed state forms at least one set of shaped electrodes; and a bridge comprising a plurality of receptacles that receive the plurality of ablation devices, wherein the bridge holds an ablation device in a fixed position relative to at least one other ablation device of the plurality of ablation devices.

Tissue ablation systems of an embodiment described above include a tissue ablation system comprising a plurality of ablation devices that each includes a trocar and an electrode array, wherein the trocar includes a plurality of orifice sets, wherein the electrode array comprises a plurality of electrode sets, wherein electrode sets of the plurality of electrode sets include a plurality of electrodes, wherein the plurality of electrode sets is deployed to a deployed state through the plurality of orifice sets, wherein electrodes of the plurality of electrodes have at least one radius of curvature in the deployed state so that the electrode array in the deployed state forms at least one set of shaped electrodes.

The tissue ablation device of an embodiment comprises a bridge comprising a plurality of receptacles that receive the plurality of ablation devices, wherein the bridge holds an ablation device in a fixed position relative to at least one other ablation device of the plurality of ablation devices.

The tissue ablation system of an embodiment includes a tissue ablation device, comprising an energy source. The device of an embodiment includes an introducer coupled to the energy source and having a body, a proximal end, and a distal end. The device of an embodiment includes an electrode array coupled to the introducer and comprising one or more electrodes. Each electrode of the one or more electrodes of an embodiment is configured to extend from the body of the introducer when moved from a retracted state to a deployed state. Each electrode of the one or more electrodes of an embodiment is configured to at least partially encircle a portion of an intended ablation that will at least partially encompass a target tissue when extended in the deployed state. Each electrode of the one or more electrodes of an embodiment is configured to form a shaped ablation pattern in a tissue volume surrounding the target tissue when energized by the energy source.

The electrodes of an embodiment extend longitudinally from the distal end of the body of the introducer.

The electrodes of an embodiment extend laterally from the body of the introducer.

The ablation pattern of an embodiment comprises one of a generally spherical pattern, an elongated spherical pattern, and a closed compound curve pattern.

The electrodes of an embodiment comprise curved metal strips. The electrode array of an embodiment comprises two or more curved metal strips arranged in an alternating polarity series that includes at least one bipolar electrode of a first polarity in series with at least one bipolar electrode of a second polarity.

The electrodes of an embodiment comprise one of flat wire electrodes, round wire electrodes, flat tube electrodes, and round tube electrodes.

The electrodes of an embodiment are bipolar electrodes. One or more of the electrodes of an embodiment include at least one internal lumen.

The tissue ablation device of an embodiment comprises an advancement device coupled to the body of the introducer to control the configuration of the electrodes. The electrodes of an embodiment are placed in the retracted state using the advancement device prior to placement of the device in the tissue volume. The electrodes of an embodiment are placed in the deployed state using the advancement device.

The energy source of an embodiment generates an energy comprising one of radio frequency and microwave energy.

The tissue ablation system of an embodiment includes a tissue ablation device comprising an array of bipolar electrodes configured to be coupled to an energy source. The array of an embodiment is configured to at least partially encircle a portion of an intended ablation that will at least partially encompass a target tissue and create an ablation pattern around a tissue volume including the target tissue. The array of an embodiment is configured to ablate the target tissue from an outside surface of the target tissue to an inner portion of the target tissue when the electrodes are energized by the energy source.

The ablation pattern of an embodiment comprises one of a generally spherical pattern, an elongated spherical pattern, and a closed compound curve pattern.

The energy source of an embodiment is coupled to the array produces energy of alternating polarity.

The bipolar electrodes of an embodiment comprise spiral metal strips. The electrode array of an embodiment comprises two or more spiral metal strips arranged in an alternating polarity series that includes at least one bipolar electrode of a first polarity in series with at least one bipolar electrode of a second polarity.

The bipolar electrodes of an embodiment comprise straight metal strips. The electrode array of an embodiment comprises two or more straight metal strips arranged in an alternating polarity series that includes at least one bipolar electrode of a first polarity in series with at least one bipolar electrode of a second polarity.

The bipolar electrodes of an embodiment comprise a first electrode section of coupled to a second electrode section through an electrically insulative physical couple. The first electrode section of an embodiment is energized to a first polarity and the second electrode section is energized to an opposite polarity upon application of energy from the energy source.

The tissue ablation device of an embodiment includes a penetrating electrode configured to penetrate a surface of the target tissue upon advancement from the array.

The array of an embodiment is comprised or two or more array portions contained within two or more introducers. Each introducer of an embodiment is configured to deploy the array in an extended position upon activation by a user and retract the array to a retracted position upon retraction by the user.

The two or more introducers of an embodiment are coupled to a single handle and activation mechanism. The activation mechanism of an embodiment is configured to allow the user to deploy or retract the array.

The two or more introducers of an embodiment are each coupled to a respective handle and activation mechanism. Each activation mechanism of an embodiment is configured to allow the user to deploy or retract a corresponding array portion through the introducer coupled to the handle.

The tissue ablation system of an embodiment includes a method of ablating tissue comprising placing a first electrode array around a first portion of a target tissue. The method of an embodiment comprises placing a second electrode array around a second portion of the target tissue. The method of an embodiment comprises energizing the first electrode array and the second electrode array to form an ablation pattern around a tissue volume including the target tissue. The method of an embodiment comprises applying sufficient energy to the first and second electrode arrays to ablate the target tissue from an outer surface to an inner portion of the target tissue.

The ablation pattern of the method of an embodiment comprises one of a generally spherical pattern, an elongated spherical pattern, and a closed compound curve pattern.

The first array of the method of an embodiment comprises one or more individual electrodes that are deployed along a first plane of the device. The second array of the method of an embodiment comprises one or more individual electrodes that are deployed along a second plane of the device.

The first array and second array of the method of an embodiment are contained in a single introducer device. The first array and second array of the method of an embodiment are deployed through an activation device coupled to a handle coupled to the introducer device.

The first array of the method of an embodiment is contained in a first introducer device. The second array of the method of an embodiment is contained in a second introducer device. The first electrode array of the method of an embodiment is deployed through an activation device in the first introducer device. The second electrode array of the method of an embodiment is deployed through an activation device in the second introducer device. A user under the method of an embodiment places the first electrode array relative to the second electrode array using the activation device of the first introducer and the activation device of the second introducer.

Energizing the first array and the second array under the method of an embodiment comprises applying radio frequency energy through the first array and the second array.

The method of an embodiment comprises applying alternating polarity to the electrodes comprising the first electrode array and the second electrode array.

The tissue ablation system of an embodiment includes a device for creating ablations in tissue comprising a trocar assembly. The device of an embodiment includes a handle assembly with an activation device integral therewith and coupled to the trocar assembly. The device of an embodiment includes a planar electrode assembly coupled to the trocar assembly. The planar electrode assembly of an embodiment is configured to be coupled to an energy source. The planar electrode assembly of an embodiment is configured to be extendable to a deployed position from a retracted position within the trocar assembly upon activation of the activation device. The planar electrode assembly of an embodiment comprises one or more individual electrodes that together circumscribe a relatively spherical ablation pattern in the tissue upon application of energy from the energy source.

The trocar assembly of an embodiment comprises two or more introducer elements each coupled to a respective handle assembly and integral activation device. A first portion of the planar electrode assembly of an embodiment is housed within a first introducer element and a second portion of the planar electrode assembly is housed within a second introducer element.

The device of an embodiment includes a guide element configured to hold a first introducer element relative to a second introducer element of the two or more introducer elements relative to one another to facilitate orientation of the first portion of the planar electrode assembly relative to the second planar electrode assembly.

The planar electrode assembly of an embodiment comprises two or more spiral electrodes extending from the trocar assembly. Each spiral electrode of an embodiment is energized to a pre-determined polarity upon application of energy from the energy source.

The planar electrode assembly of an embodiment comprises two or more straight electrodes extending from the trocar assembly. Each straight electrode of an embodiment is energized to a pre-determined polarity upon application of energy from the energy source.

The planar electrode assembly of an embodiment comprises two or more electrodes extending from the trocar assembly. Each electrode of an embodiment includes a first portion energized to a first pre-determined polarity upon application of energy from the energy source. Each electrode of an embodiment includes a second portion energized to a second pre-determined polarity upon application of energy from the energy source.

The relatively spherical ablation pattern of an embodiment comprises an elongated spherical ablation pattern.

The energy source of an embodiment is configured to generate energy of alternating polarity to the planar electrode assembly.

The energy source of an embodiment produces radio frequency energy.

The tissue ablation devices and methods described herein include a tissue ablation device, comprising an energy source; an introducer coupled to the energy source and having a body, a proximal end, and a distal end; and an electrode array coupled to the introducer and comprising a plurality of electrodes, each electrode of the plurality of electrodes configured to extend from the body of the introducer when moved from a retracted state to a deployed state, and configured to at least partially encircle an intended ablation that will at least partially encompass a target tissue when extended in the deployed state and to form a relatively spherical shaped ablation pattern in a tissue volume surrounding the target tissue when energized by the energy source.

A tissue ablation device of embodiments include electrodes that extend longitudinally from the distal end of the body of the introducer or laterally from the body of the introducer.

The energy source of an embodiment includes a radio frequency (RF) generator.

The tissue ablation devices and methods described herein include an array of bipolar electrodes configured to be coupled to an energy source, wherein the array is configured to encircle at least a portion of a target tissue and create a relatively spherical ablation pattern around a tissue volume including the target tissue, and ablate the target tissue from an outside surface of the target tissue to an inner portion of the target tissue when the electrodes are energized by the energy source.

The system of an embodiment further comprises a controller coupled among the RF generator and the bipolar electrodes to provide automatic control of energy delivery to each of the bipolar electrodes.

The bipolar electrodes in an embodiment comprise spiral metal strips, and the electrode array comprises two or more spiral metal strips arranged in an alternating polarity series that includes at least one bipolar electrode of a first polarity in series with at least one bipolar electrode of a second polarity.

The tissue ablation device of an embodiment comprises two or more introducers coupled to a single handle and activation mechanism that allows a user to deploy or retract the electrode array.

The tissue ablation device of an alternative embodiment comprises two or more introducers coupled to respective handles and activation mechanisms that allows a user to deploy or retract a respective portion of the electrode array coupled to each introducer.

Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list and any combination of the items in the list.

The above description of illustrated embodiments of the tissue ablation devices and methods is not intended to be exhaustive or to limit the systems and methods to the precise form disclosed. While specific embodiments of, and examples for, the tissue ablation devices and methods are described herein for illustrative purposes, various equivalent modifications are possible within the scope of the systems and methods, as those skilled in the relevant art will recognize. The teachings of the tissue ablation devices and methods provided herein can be applied to other medical systems, not only for the medical systems described above.

The elements and acts of the various embodiments described above can be combined to provide further embodiments. These and other changes can be made to the tissue ablation devices and methods in light of the above detailed description. As an example, following are one or more examples of additional embodiments of the tissue ablation devices, each of which may be used alone or in combination with other embodiments described herein.

The tissue ablation devices and methods further include allowing the device intended to create an ablation in tissue to surround, encompass, or otherwise create a three dimensional perimeter around a volume of tissue, such as a tumor, without penetrating or going through the such volume.

The tissue ablation devices and methods further include the ability and method in either a mono-polar or bi-polar configuration for a device to switch between various electrodes thereby creating different groups of active electrodes and creating different paths of current flow after the application of energy to the target tissue.

The tissue ablation devices and methods further include the ability and method in either a mono-polar or bi-polar configuration for a device to switch between various electrodes thereby creating different groups of active electrodes and creating different paths of current flow after the application of energy to the target tissue, and/or to continue to switch in any combination and for any number of times.

The tissue ablation devices and methods further include the ability and method in either a mono-polar or bi-polar configuration for a device to switch between various electrodes thereby creating different groups of active electrodes and creating different paths of current flow after the application of energy to the target tissue, and/or to continue to switch in any combination and for any number of times, and/or the ability to switch on the fly with or without the reduction of applied power.

The tissue ablation devices and methods further include the ability and method in either a mono-polar or bi-polar configuration for a device to switch between various electrodes thereby creating different groups of active electrodes and creating different paths of current flow after the application of energy to the target tissue, and/or to continue to switch in any combination and for any number of times, and/or the ability to switch on the fly with or without the reduction of applied power, and/or to alter the applied energy prior to switching.

The tissue ablation devices and methods further include the ability and method in either a mono-polar or bi-polar configuration for a device to switch between various electrodes thereby creating different groups of active electrodes and creating different paths of current flow after the application of energy to the target tissue, and/or to continue to switch in any combination and for any number of times, and/or the ability to switch on the fly with or without the reduction of applied power, and/or to alter the applied energy prior to switching, and/or to switch based on fixed or changing tissue characteristics including, but not limited to, tissue temperature, impedance, rate of change of temperature, rate of change of impedance, and the like.

The tissue ablation devices and methods further include using electrode coatings or other means to locally lower the impedance around them without significantly reducing the impedance a large (several electrode diameters or width) distance away from the electrode; e.g., application of energy in such a way and for the purpose of releasing conductive interstitial cellular fluid or a coating of salt crystals on the electrodes.

The tissue ablation devices and methods further include applying energy followed by a reduction or dwell time followed by the application or reapplication of energy to aid in the application of higher amounts of energy. This may be performed using various wave forms for example saw-tooth, square wave, and the like including, but not limited to, the controlling the delivery of energy to a level at or near zero (0).

The tissue ablation devices and methods further include applying energy followed by a reduction or dwell time followed by the application or reapplication of energy to aid in the application of higher amounts of energy. This may be performed using various wave forms for example saw-tooth, square wave, and the like including, but not limited to, the controlling the delivery of energy to a level at or near zero (0), and/or where the energy delivered is reduced or eliminated with/at approximately the same time the energy is increased between other electrodes or electrode pairs or some of the current and some other electrodes within the device.

The tissue ablation devices and methods further include applying energy followed by a reduction or dwell time followed by the application or reapplication of energy to aid in the application of higher amounts of energy. This may be performed using various wave forms for example saw-tooth, square wave, and the like including, but not limited to, the controlling the delivery of energy to a level at or near zero (0), and/or where the energy delivered is reduced or eliminated with/at approximately the same time the energy is increased between other electrodes or electrode pairs or some of the current and some other electrodes within the device, for any combinations, durations, fixed or varying power levels, and for any duration or number of cycles.

The tissue ablation devices and methods further include the use of high energy levels that are otherwise unsustainable due to the increase in tissue impedance or tissue char followed by a reduction in delivered energy that includes a reduction or dwell time followed by the application or reapplication of energy to aid in the application of higher amounts of energy. This may be performed using various wave forms for example saw-tooth, square wave, and the like including, but not limited to, the controlling the delivery of energy to a level at or near zero (0).

The tissue ablation devices and methods further include the ability to change the deployment shape of the electrodes to, for example, be able to alter the diameter of the deployed electrodes resulting in various sizes of ablative tissue (e.g., 3 cm diameter, 5 cm diameter, 7.5 cm diameter, and 15 cm diameter) by means of elements that are pulled ("pull wires"), pushed ("push wires"), differential heating and subsequent expansion of off-axis elements to name a few.

The tissue ablation devices and methods further include the ability to partially deploy the electrodes for the creation of smaller ablations resulting in various sizes of ablative tissue (e.g., 3 cm diameter by partially deploying a 5 cm diameter or 7 cm diameter device.

The tissue ablation devices and methods further include allowing the device intended to create an ablation in tissue to surround, encompass, or otherwise create a three dimensional perimeter around a volume of tissue, such as a tumor, without penetrating or going through the such volume, where the electrode configuration creates a nominal predefined shape when used a predefined way.

The elements and acts of the various embodiments described above can be combined to provide further embodiments. These and other changes can be made to the thermal ablation methods and devices in light of the above detailed description.

What is claimed is:

1. A tissue ablation device, comprising:
    a trocar including a distal end and a lumen extending along a longitudinal axis of the trocar, wherein the trocar includes a plurality of orifices positioned along the longitudinal axis; and
    an electrode array comprising a plurality of electrodes, wherein the plurality of electrodes is positioned in the lumen in a retracted state, wherein the plurality of electrodes is deployed to a deployed state through a set of orifices of the plurality of orifices, wherein each electrode of the plurality of electrodes has a substantially circular shape in the deployed state so that the electrode array forms a linear series of substantially circular electrodes in the deployed state, wherein a planar area formed internal to each deployed electrode overlaps the planar area formed internal to at least one other electrode of the plurality of electrodes.

2. The device of claim 1, wherein at least one radius of curvature of each electrode is proportional to a size of an ablation volume generated with the electrode array in the deployed state.

3. The device of claim 1, wherein at least one radius of curvature of each electrode is determinative of a shape of an ablation volume generated with the electrode array in the deployed state.

4. The device of claim 1, wherein each electrode of the plurality of electrodes in the deployed state has an effective surface area proportional to the at least one radius of curvature.

5. The device of claim 1, wherein the electrode array in the deployed state forms a planar series of shaped electrodes.

6. The device of claim 1, wherein the electrode array in the deployed state forms a linear series of shaped electrodes aligned along the longitudinal axis.

7. The device of claim 1, wherein a shape of the shaped electrodes is an ellipse.

8. The device of claim 1, wherein a shape of the shaped electrodes is a circle.

9. The device of claim 1, wherein a shape of the shaped electrodes is a semicircle.

10. The device of claim 1, wherein the distal end of the trocar includes a sharp region for piercing tissue.

11. The device of claim 1, wherein a distal tip of each electrode of the plurality of electrodes includes a sharp region for penetrating tissue.

12. The device of claim 1, wherein distal tips of each of the plurality of electrodes, when transitioning from the retracted state to the deployed state, transition through approximately all points in a plane at a distance from a fixed center reference point, wherein the distance is the at least one radius of curvature.

13. The device of claim 1, wherein distal tips of each of the plurality of electrodes, when transitioning from the retracted state to the deployed state, transition through a majority of points in a plane at a distance from a fixed center reference point, wherein the distance is the at least one radius of curvature.

14. The device of claim 1, wherein distal tips of each of the plurality of electrodes, when transitioning from the retracted state to the deployed state, transition through approximately all points in a plane such that a sum of distances to a first fixed point and a second fixed point of the points is a constant.

15. The device of claim 1, wherein distal tips of each of the plurality of electrodes, when transitioning from the retracted state to the deployed state, transition through a majority of points in a plane such that a sum of distances to a first fixed point and a second fixed point of the points is a constant.

16. The device of claim 1, wherein the plurality of electrodes is deployed to a partially deployed state.

17. The device of claim 16, wherein distal tips of each of the plurality of electrodes, when transitioning from the retracted state to the partially deployed state, transition through a portion of points in a plane at a distance from a fixed center reference point, wherein the distance is the at least one radius of curvature.

18. The device of claim 16, wherein distal tips of each of the plurality of electrodes, when transitioning from the retracted state to the partially deployed state, transition through a portion of points in a plane such that a sum of distances to a first fixed point and a second fixed point of the portion of points is a constant.

19. The device of claim 1, wherein the plurality of electrodes includes two electrodes.

20. The device of claim 19, wherein a first center of a first shape formed by a first electrode is offset from a second center of a second shape formed by a second electrode.

21. The device of claim 20, wherein the first shape is a first ellipse having a first radius of curvature and the second shape is a second ellipse having a second radius of curvature.

22. The device of claim 21, wherein the first radius of curvature is different than the second radius of curvature.

23. The device of claim 21, wherein the first radius of curvature is approximately equivalent to the second radius of curvature.

24. The device of claim 1, wherein the plurality of electrodes includes three electrodes.

25. The device of claim 24, wherein a first center of a first shape formed by a first electrode is offset from one or more of a second center of a second shape formed by a second electrode and a third center of a third shape formed by a third electrode.

26. The device of claim 25, wherein the first shape is a first ellipse having a first radius of curvature, the second shape is a second ellipse having a second radius of curvature, and the third shape is a third ellipse having a third radius of curvature.

27. The device of claim 26, wherein the first radius of curvature is different than one or more of the second radius of curvature and the third radius of curvature.

28. The device of claim 26, wherein the first radius of curvature is approximately equivalent to one or more of the second radius of curvature and the third radius of curvature.

29. The device of claim 1, wherein the plurality of electrodes includes four electrodes.

30. The device of claim 29, wherein a first center of a first shape formed by a first electrode is offset from one or more of a second center of a second shape formed by a second electrode, a third center of a third shape formed by a third electrode, and a fourth center of a fourth shape formed by a fourth electrode.

31. The device of claim 30, wherein the first shape is a first ellipse having a first radius of curvature, the second shape is a second ellipse having a second radius of curvature, the third shape is a third ellipse having a third radius of curvature, and the fourth shape is a fourth ellipse having a fourth radius of curvature.

32. The device of claim 31, wherein the first radius of curvature is different than one or more of the second radius of curvature, the third radius of curvature, and the fourth radius of curvature.

33. The device of claim 31, wherein the first radius of curvature is approximately equivalent to one or more of the second radius of curvature, the third radius of curvature, and the fourth radius of curvature.

34. The device of claim 1, wherein each electrode of the plurality of electrodes has a first polarity.

35. The device of claim 1, wherein a first set of electrodes of the plurality of electrodes has a first polarity and a second set of electrodes of the plurality of electrodes has a second polarity.

36. The device of claim 1, wherein the plurality of electrodes is deployed laterally through the plurality of orifices to the deployed state.

37. The device of claim 1, wherein the plurality of electrodes comprise flat wire electrodes.

38. The device of claim 1, wherein at least one electrode of the plurality of electrodes comprises one or more of a flat wire electrode, a round wire electrode, a flat tube electrode, and a round tube electrode.

39. The device of claim 1, wherein each orifice of the plurality of lateral orifices is longitudinally aligned with each other orifice along the longitudinal axis.

40. The device of claim 1, wherein an electrode of the plurality of electrodes includes an electrode lumen.

41. The device of claim 1, comprising a handle assembly coupled to the trocar and the electrode array.

42. The device of claim 1, wherein the electrode array, when positioned in proximity to target tissue, defines an outer surface of an ablation volume.

43. The device of claim 1, wherein the plurality of electrodes comprises a number of electrodes appropriate to create an ablation volume in target tissue without impeding out the electrode array when electromagnetic energy is delivered to the electrode.

44. The device of claim 43, wherein the electrode array, when positioned in proximity to the target tissue, defines an outer surface of the ablation volume and at least partially encircles the ablation volume.

45. The device of claim 43, wherein, when electromagnetic energy is delivered to the electrode array, the electrode array ablates the target tissue starting from the outer surface and progressing toward an inner portion of the target tissue.

46. The device of claim 1, comprising at least one additional lumen extending along the longitudinal axis.

47. A tissue ablation device, comprising:
- a trocar including a distal end, a lumen extending along a longitudinal axis of the trocar, and a plurality of orifices positioned along the longitudinal axis; and
- an electrode array comprising a plurality of electrodes, wherein the plurality of electrodes is positioned in the lumen in a retracted state, wherein the plurality of electrodes is deployed to a deployed state through a set of the plurality of orifices, wherein each electrode of the plurality of electrodes has a substantially circular shape in the deployed state so that the electrode array forms a linear series of substantially circular electrodes in the deployed state, wherein a planar area formed internal to each deployed electrode overlaps the planar area formed internal to at least one other electrode of the plurality of electrodes.

48. A tissue ablation device, comprising:
- a trocar including a distal end and a lumen extending along a longitudinal axis of the trocar, wherein the distal end includes a sharp region for piercing tissue, wherein the trocar includes a plurality of orifices positioned along the longitudinal axis;
- an electrode array comprising a plurality of electrodes, wherein the plurality of electrodes has a retracted state and a deployed state, wherein each electrode of the plurality of electrodes is contained in the lumen in the retracted state, wherein one or more electrode is deployed through an orifice of the plurality of orifices, wherein each electrode has a substantially elliptical shape in the deployed state, wherein the electrode array forms a linear series of elliptical electrodes in the deployed state, wherein a planar area formed internal to each deployed electrode overlaps the planar area formed internal to at least one other electrode of the plurality of electrodes.

49. A tissue ablation device, comprising:
- a trocar including a distal end and a lumen extending along a longitudinal axis of the trocar, wherein the trocar includes a plurality of orifices aligned along the longitudinal axis;
- an electrode array comprising a plurality of electrodes, wherein the plurality of electrodes are deployed from the lumen via the plurality of orifices, wherein each electrode of the plurality of electrodes has a substantially elliptical shape in a deployed state, wherein the electrode array in the deployed state forms a linear series of substantially elliptical electrodes aligned along the longitudinal axis, wherein a planar area formed internal to each deployed electrode overlaps the planar area formed internal to at least one other electrode of the plurality of electrodes.

* * * * *